(12) United States Patent
Lee et al.

(10) Patent No.: US 6,696,260 B1
(45) Date of Patent: Feb. 24, 2004

(54) METHODS TO IDENTIFY GROWTH DIFFERENTIATION FACTOR (GDF) BINDING PROTEINS

(75) Inventors: Se-Jin Lee, Baltimore, MD (US); Alexandra McPherron, Baltimore, MD (US)

(73) Assignee: The Johns Hopkins University School of Medicine, Baltimore, MD (US)

(*) Notice: Subject to any disclaimer, the term of this patent is extended or adjusted under 35 U.S.C. 154(b) by 0 days.

(21) Appl. No.: 09/485,046

(22) PCT Filed: Aug. 1, 1997

(86) PCT No.: PCT/US98/15598

§ 371 (c)(1),
(2), (4) Date: May 5, 2000

(87) PCT Pub. No.: WO99/06559

PCT Pub. Date: Feb. 11, 1999

Related U.S. Application Data

(60) Provisional application No. 60/054,461, filed on Aug. 1, 1997.

(51) Int. Cl.[7] ..................... G01N 33/567; G01N 33/53; C12P 21/06; C12N 15/74; C12N 5/02
(52) U.S. Cl. ..................... 435/7.21; 435/7.1; 435/69.1; 435/320.1; 435/325; 530/350
(58) Field of Search ................... 435/7.1, 7.21, 435/69.1, 320.1, 325; 530/350

(56) References Cited

U.S. PATENT DOCUMENTS

| | | |
|---|---|---|
| 5,734,039 A | 3/1998 | Calabretta et al. |
| 5,827,733 A | 10/1998 | Lee et al. |
| 5,885,794 A | 3/1999 | Mathews et al. |
| 5,994,618 A | 11/1999 | Lee et al. |
| 6,004,937 A | 12/1999 | Wood et al. |

FOREIGN PATENT DOCUMENTS

| | | |
|---|---|---|
| WO | WO 98/33887 | 5/1998 |
| WO | WO99/06559 | 2/1999 |
| WO | WO99/56768 | 11/1999 |

OTHER PUBLICATIONS

Nishitoh et al., J. Biol. Chem. 1996, vol. 271, pp. 21345–21352.*
Hannon et al. J. Cell Biol. 1996, vol. 132, pp. 1151–1159.*
Massague, J. Ann. Rev. Biochem. 1998, vol. 67, pp. 753–791.*
Sutrave et al., "The induction of skeletal muscle hypertrophy by a *ski* transgene is promoter–dependent," *Gene*, vol. 241, pp. 107–116 (2000).
Yamamoto et al., "Smad1 and Smad5 Act Downstream of Intracellular Signalings of BMP–2 That Inhibits Myogenic Differentiation and Induces Osteoblast Differentiation in C2C12 Myoblast," *Biochemical and Biophysical Research Communications*, vol. 238, pp. 574–580 (1997).
McPherron and Lee et al., "Double muscling in cattle due to mutations in the myostatin gene," *Proc. Natl. Acad. Sci USA*, vol. 94, pp. 12457–12461, Nov. 1997.
Gamer et al., "A Novel BMP Expressed in Developing Mouse Limb, Spinal Cord, and Tail Bud Is a Potent Mesoderm Inducer in *Xenopus* Embryos," *Development Biology*, vol. 298, pp. 222–232 (1999).
Berk et al., "Mice Lacking the *ski* Proto–Oncogene Have Defects in Neurulation, Craniofacial Patterning, and Skeletal Muscle Development," *Genes & Development* 11:2029–2039 (1997).
Böttinger et al., "The Recombinant Proregion of Transforming Growth Factor β1 (Latency–Associated Peptide) Inhibits Active Transforming Growth Factor β1 in Transgenic Mice," *Proc. Natl. Acad. Sci* 93:5877–5882 (1996).
Gamer et al., "A Novel BMP Expressed in Developing Mouse Limb, Spinal Cord, and Tail Bud Is A Potent Mesoderm Inducer in *Xenopus* Embryos," *Developmental Biology* 208: 222–232 (1999).
Gentry and Nash, "The Pro Domain of Pre–Pro–Transforming Growth Factor β1 When Independently Expressed is a Functional Binding Protein for the Mature Growth Factor," *Biochemistry* 29:6851–6857 (1990).
Gonzalez–Cadavid et al., "Organization of the Luman Myostatin Gene and Expression in Healthy Men and HIV–Infected Men with Muscle Wasting," *Proc.Natl.Acad.Sci.* 95:14938–14943 (1998).
Lee and McPherron, "Myostatin and the Control of Skeletal Muscle Mass," *Curr. Opin. Genet. Dev.* 9:604–607 (1999).
Luo et al., "The Ski Oncoprotein Interacts with the Smad Proteins to Repress TGFβ Signaling," *Genes & Dev.* 13:2196–2206 (1999).
McPherron et al., "Regulation of Anterior/Posterior Patterning of the Axial Skeleton by Growth/Differentiation Factor 11," *Nature Genetics* 22:260–264 (1999).
Miyazono et al., "Latent High Molecular Weight Complex of Transforming Growth Factor β1," *J. Bio. Chem.* 263 (13):6407–6415 (1988).
Munger et al., "Latent Transforming Growth Factor–β: Structural Features and Mechanisms of Activation," *Kidney Intl.* 51:1376–1382 (1997).
Nakamura et al., "Activin–Binding Protein from Rat Ovary is Follistatin," *Science* 247:836–838 (1990).

(List continued on next page.)

Primary Examiner—Yvonne Eyler
Assistant Examiner—Janet L. Andres
(74) Attorney, Agent, or Firm—Gray Cary Ware & Freidenrich, LLP; Lisa A. Haile; Richard J. Imbra

(57) ABSTRACT

The present invention provides receptors for the growth differentiation factor (GDF) family of growth factors and methods of identifying such receptors. Also included are methods of identifying antibodies which bind to the receptors, peptide fragments of the receptor which inhibit GDF binding, GDF receptor-binding agents capable of blocking GDF binding to the receptor. The receptors of the invention allow the identification of antagonists or agonists useful for agricultural and human therapeutic purposes.

26 Claims, 28 Drawing Sheets

OTHER PUBLICATIONS

Oh and Li, "The Signaling Pathway Mediated by the Type IIB Activin Receptor Controls Axial Patterning and Lateral Asymmetry in the Mouse," *Genes & Dev.* 11:1812–1826 (1997).

Sutrave et al., "Ski can Cause Selective Growth of Skeletal Muscle in Transgenic Mice," *Genes & Dev.* 4:1462–1472 (1990).

Wall et al., "Transgenic Dairy Cattle: Genetic Engineering on a Large Scale," *J. Dairy Sci.*, vol. 80, pp. 2213–2224 (1997).

Moreadith and Radford, "Gene targeting in embryonic stem cells: the new physiology and metabolism," *J. Mol. Med.*, vol. 75, pp. 208–216 (1997).

Linda Mullins and John Mullins, "Transgenesis in the Rat and Larger Mammals," *J. Clin. Invest.*, vol. 97, No. 7, pp. 1557–1560, Apr. 1996.

Ebert et al., "A Moloney MLV–Rat Somatotropin Fusion Gene Produces Biologically Active Somatotropin in a Transgenic Pig," *Mol. Endo.*, vol. 2, No. 3, pp. 277–283 (1988).

Hammer et al., "Genetic Engineering of Mammalian Embryos," *J. Anim. Sci.,* vol. 63, pp. 269–278, Jul. 1986.

* cited by examiner

```
  1 GTCTCTCGGACGGTACATGCACTAATATTTCACTTGGCATTACTCAAAAGCAAAAAGAAG  60
 61 AAATAAGAACAAGGGAAAAAAAAAGATTGTGCTGATTTTTAAAATGATGCAAAAACTGCA 120
                                                    M  M  Q  K  L  Q
121 AATGTATGTTTATATTTACCTGTTCATGCTGATTGCTGCTGGCCCAGTGGATCTAAATGA 180
     M  Y  V  Y  I  Y  L  F  M  L  I  A  A  G  P  V  D  L  N  E
181 GGGCAGTGAGAGAGAAGAAAATGTGGAAAAAGAGGGGCTGTGTAATGCATGTGCGTGGAG 240
     G  S  E  R  E  E  N  V  E  K  E  G  L  C  N  A  C  A  W  R
241 ACAAAACACGAGGTACTCCAGAATAGAAGCCATAAAAATTCAAATCCTCAGTAAGCTGCG 300
     Q  N  T  R  Y  S  R  I  E  A  I  K  I  Q  I  L  S  K  L  R
301 CCTGGAAACAGCTCCTAACATCAGCAAAGATGCTATAAGACAACTTCTGCCAAGAGCGCC 360
     L  E  T  A  P  N  I  S  K  D  A  I  R  Q  L  L  P  R  A  P
361 TCCACTCCGGGAACTGATCGATCAGTACGACGTCCAGAGGGATGACAGCAGTGATGGCTC 420
     P  L  R  E  L  I  D  Q  Y  D  V  Q  R  D  D  S  S  D  G  S
421 TTTGGAAGATGACGATTATCACGCTACCACGGAAACAATCATTACCATGCCTACAGAGTC 480
     L  E  D  D  D  Y  H  A  T  T  E  T  I  I  T  M  P  T  E  S
481 TGACTTTCTAATGCAAGCGGATGGCAAGCCCAAATGTTGCTTTTTTAAATTTAGCTCTAA 540
     D  F  L  M  Q  A  D  G  K  P  K  C  C  F  F  K  F  S  S  K
541 AATACAGTACAACAAAGTAGTAAAAGCCCAACTGTGGATATATCTCAGACCCGTCAAGAC 600
     I  Q  Y  N  K  V  V  K  A  Q  L  W  I  Y  L  R  P  V  K  T
601 TCCTACAACAGTGTTTGTGCAAATCCTGAGACTCATCAAACCCATGAAAGACGGTACAAG 660
     P  T  T  V  F  V  Q  I  L  R  L  I  K  P  M  K  D  G  T  R
661 GTATACTGGAATCCGATCTCTGAAACTTGACATGAGCCCAGGCACTGGTATTTGGCAGAG 720
     Y  T  G  I  R  S  L  K  L  D  M  S  P  G  T  G  I  W  Q  S
721 TATTGATGTGAAGACAGTGTTGCAAAATTGGCTCAAACAGCCTGAATCCAACTTAGGCAT 780
     I  D  V  K  T  V  L  Q  N  W  L  K  Q  P  E  S  N  L  G  I
781 TGAAATCAAAGCTTTGGATGAGAATGGCCATGATCTTGCTGTAACCTTCCCAGGACCAGG 840
     E  I  K  A  L  D  E  N  G  H  D  L  A  V  T  F  P  G  P  G
841 AGAAGATGGGCTGAATCCCTTTTTAGAAGTCAAGGTGACAGACACACCCAAGAGGTCCCG 900
     E  D  G  L  N  P  F  L  E  V  K  V  T  D  T  P  K  R  S  R
901 GAGAGACTTTGGGCTTGACTGCGATGAGCACTCCACGGAATCCCGGTGCTGCCGCTACCC 960
     R  D  F  G  L  D  C  D  E  H  S  T  E  S  R  C  C  R  Y  P
961 CCTCACGGTCGATTTTGAAGCCTTTGGATGGGACTGGATTATCGCACCCAAAAGATATAA 1020
     L  T  V  D  F  E  A  F  G  W  D  W  I  I  A  P  K  R  Y  K
1021 GGCCAATTACTGCTCAGGAGAGTGTGAATTTGTGTTTTTACAAAAATATCCGCATACTCA 1080
      A  N  Y  C  S  G  E  C  E  F  V  F  L  Q  K  Y  P  H  T  H
1081 TCTTGTGCACCAAGCAAACCCCAGAGGCTCAGCAGGCCCTTGCTGCACTCCGACAAAAAT 1140
      L  V  H  Q  A  N  P  R  G  S  A  G  P  C  C  T  P  T  K  M
1141 GTCTCCCATTAATATGCTATATTTTAATGGCAAAGAACAAATAATATATGGGAAAATTCC 1200
      S  P  I  N  M  L  Y  F  N  G  K  E  Q  I  I  Y  G  K  I  P
1201 AGCCATGGTAGTAGACCGCTGTGGGTGCTCATGAGCTTTGCATTAGGTTAGAAACTTCCC 1260
      A  M  V  V  D  R  C  G  C  S  *
```

Fig. 1A

```
1261 AAGTCATGGAAGGTCTTCCCCTCAATTTCGAAACTGTGAATTCAAGCACCACAGGCTGTA 1320
1321 GGCCTTGAGTATGCTCTAGTAACGTAAGCACAAGCTACAGTGTATGAACTAAAAGAGAGA 1380
1381 ATAGATGCAATGGTTGGCATTCAACCACCAAAATAAACCATACTATAGGATGTTGTATGA 1440
1441 TTTCCAGAGTTTTTGAAATAGATGGAGATCAAATTACATTTATGTCCATATATGTATATT 1500
1501 ACAACTACAATCTAGGCAAGGAAGTGAGAGCACATCTTGTGGTCTGCTGAGTTAGGAGGG 1560
1561 TATGATTAAAAGGTAAAGTCTTATTTCCTAACAGTTTCACTTAATATTTACAGAAGAATC 1620
1621 TATATGTAGCCTTTGTAAAGTGTAGGATTGTTATCATTTAAAAACATCATGTACACTTAT 1680
1681 ATTTGTATTGTATACTTGGTAAGATAAAATTCCACAAAGTAGGAATGGGGCCTCACATAC 1740
1741 ACATTGCCATTCCTATTATAATTGGACAATCCACCACGGTGCTAATGCAGTGCTGAATGG 1800
1801 CTCCTACTGGACCTCTCGATAGAACACTCTACAAAGTACGAGTCTCTCTCTCCCTTCCAG 1860
1861 GTGCATCTCCACACACACAGCACTAAGTGTTCAATGCATTTTCTTTAAGGAAAGAAGAAT 1920
1921 CTTTTTTTCTAGAGGTCAACTTTCAGTCAACTCTAGCACAGCGGGAGTGACTGCTGCATC 1980
1981 TTAAAAGGCAGCCAAACAGTATTCATTTTTTAATCTAAATTTCAAAATCACTGTCTGCCT 2040
2041 TTATCACATGGCAATTTTGTGGTAAAATAATGGAAATGACTGGTTCTATCAATATTGTAT 2100
2101 AAAAGACTCTGAAACAATTACATTTATATAATATGTATACAATATTGTTTTGTAAATAAG 2160
2161 TGTCTCCTTTTATATTTACTTTGGTATATTTTTACACTAATGAAATTTCAAATCATTAAA 2220
2221 GTACAAAGACATGTCATGTATCACAAAAAAGGTGACTGCTTCTATTTCAGAGTGAATTAG 2280
2281 CAGATTCAATAGTGGTCTTAAAACTCTGTATGTTAAGATTAGAAGGTTATATTACAATCA 2340
2341 ATTTATGTATTTTTACATTATCAACTTATGGTTTCATGGTGGCTGTATCTATGAATGTG 2400
2401 GCTCCCAGTCAAATTTCAATGCCCCACCATTTTAAAAATTACAAGCATTACTAAACATAC 2460
2461 CAACATGTATCTAAAGAAATACAAATATGGTATCTCAATAACAGCTACTTTTTTATTTTA 2520
2521 TAATTTGACAATGAATACATTTCTTTTATTTACTTCAGTTTTATAAATTGGAACTTTGTT 2580
2581 TATCAAATGTATTGTACTCATAGCTAAATGAAATTATTTCTTACATAAAAATGTGTAGAA 2640
2641 ACTATAAATTAAAGTGTTTTCACATTTTTGAAAGGC 2676
```

Fig. 1B

```
   1 AAGAAAAGTAAAAGGAAGAAACAAGAACAAGAAAAAAGATTATATTGATTTTAAAATCAT   60
                                                                 M
  61 GCAAAAACTGCAACTCTGTGTTTATATTTACCTGTTTATGCTGATTGTTGCTGGTCCAGT  120
     Q   K   L   Q   L   C   V   Y   I   Y   L   F   M   L   I   V   A   G   P   V
 121 GGATCTAAATGAGAACAGTGAGCAAAAAGAAAATGTGGAAAAAGAGGGGCTGTGTAATGC  180
     D   L   N   E   N   S   E   Q   K   E   N   V   E   K   E   G   L   C   N   A
 181 ATGTACTTGGAGACAAAACACTAAATCTTCAAGAATAGAAGCCATTAAGATACAAATCCT  240
     C   T   W   R   Q   N   T   K   S   S   R   I   E   A   I   K   I   Q   I   L
 241 CAGTAAACTTCGTCTGGAAACAGCTCCTAACATCAGCAAAGATGTTATAAGACAACTTTT  300
     S   K   L   R   L   E   T   A   P  [N   I   S]  K   D   V   I   R   Q   L   L
 301 ACCCAAAGCTCCTCCACTCCGGGAACTGATTGATCAGTATGATGTCCAGAGGGATGACAG  360
     P   K   A   P   P   L   R   E   L   I   D   Q   Y   D   V   Q   R   D   D   S
 361 CAGCGATGGCTCTTTGGAAGATGACGATTATCACGCTACAACGGAAACAATCATTACCAT  420
     S   D   G   S   L   E   D   D   D   Y   H   A   T   T   E   T   I   I   T   M
 421 GCCTACAGAGTCTGATTTTCTAATGCAAGTGGATGGAAAACCCAAATGTTGCTTCTTTAA  480
     P   T   E   S   D   F   L   M   Q   V   D   G   K   P   K   C   C   F   F   K
 481 ATTTAGCTCTAAAATACAATACAATAAAGTAGTAAAGGCCCAACTATGGATATATTTGAG  540
     F   S   S   K   I   Q   Y   N   K   V   V   K   A   Q   L   W   I   Y   L   R
 541 ACCCGTCGAGACTCCTACAACAGTGTTTGTGCAAATCCTGAGACTCATCAAACCTATGAA  600
     P   V   E   T   P   T   T   V   F   V   Q   I   L   R   L   I   K   P   M   K
 601 AGACGGTACAAGGTATACTGGAATCCGATCTCTGAAACTTGACATGAACCCAGGCACTGG  660
     D   G   T   R   Y   T   G   I   R   S   L   K   L   D   M   N   P   G   T   G
 661 TATTTGGCAGAGCATTGATGTGAAGACAGTGTTGCAAAATTGGCTCAAACAACCTGAATC  720
     I   W   Q   S   I   D   V   K   T   V   L   Q   N   W   L   K   Q   P   E   S
 721 CAACTTAGGCATTGAAATAAAAGCTTTAGATGAGAATGGTCATGATCTTGCTGTAACCTT  780
     N   L   G   I   E   I   K   A   L   D   E   N   G   H   D   L   A   V   T   F
 781 CCCAGGACCAGGAGAAGATGGGCTGAATCCGTTTTTAGAGGTCAAGGTAACAGACACACC  840
     P   G   P   G   E   D   G   L   N   P   F   L   E   V   K   V   T   D   T   P
 841 AAAAAGATCCAGAAGGGATTTTGGTCTTGACTGTGATGAGCACTCAACAGAATACGATG  900
     K  [R   S   R   R]  D   F   G   L   D   C   D   E   H   S   T   E   S   R   C
 901 CTGTCGTTACCCTCTAACTGTGGATTTTGAAGCTTTTGGATGGGATTGGATTATCGCTCC  960
     C   R   Y   P   L   T   V   D   F   E   A   F   G   W   D   W   I   I   A   P
 961 TAAAAGATATAAGGCCAATTACTGCTCTGGAGAGTGTGAATTTGTATTTTTACAAAAATA 1020
     K   R   Y   K   A   N   Y   C   S   G   E   C   E   F   V   F   L   Q   K   Y
1021 TCCTCATACTCATCTGGTACACCAAGCAAACCCCAGAGGTTCAGCAGGCCCTTGCTGTAC 1080
     P   H   T   H   L   V   H   Q   A   N   P   R   G   S   A   G   P   C   C   T
1081 TCCCACAAAGATGTCTCCAATTAATATGCTATATTTTAATGGCAAAGAACAAATAATATA 1140
     P   T   K   M   S   P   I   N   M   L   Y   F   N   G   K   E   Q   I   I   Y
1141 TGGGAAAATTCCAGCGATGGTAGTAGACCGCTGTGGGTGCTCATGAGATTTATATTAAGC 1200
     G   K   I   P   A   M   V   V   D   R   C   G   C   S   *
```

Fig. 1C

```
1201 GTTCATAACTTCCTAAAACATGGAAGGTTTTCCCCTCAACAATTTTGAAGCTGTGAAATT 1260
1261 AAGTACCACAGGCTATAGGCCTAGAGTATGCTACAGTCACTTAAGCATAAGCTACAGTAT 1320
1321 GTAAACTAAAAGGGGGAATATATGCAATGGTTGGCATTTAACCATCCAAACAAATCATAC 1380
1381 AAGAAAGTTTTATGATTTCCAGAGTTTTTGAGCTAGAAGGAGATCAAATTACATTTATGT 1440
1441 TCCTATATATTACAACATCGGCGAGGAAATGAAAGCGATTCTCCTTGAGTTCTGATGAAT 1500
1501 TAAAGGAGTATGCTTTAAAGTCTATTTCTTTAAAGTTTTGTTTAATATTTACAGAAAAAT 1560
1561 CCACATACAGTATTGGTAAAATGCAGGATTGTTATATACCATCATTCGAATCATCCTTAA 1620
1621 ACACTTGAATTTATATTGTATGGTAGTATACTTGGTAAGATAAAATTCCACAAAAATAGG 1680
1681 GATGGTGCAGCATATGCAATTTCCATTCCTATTATAATTGACACAGTACATTAACAATCC 1740
1741 ATGCCAACGGTGCTAATACGATAGGCTGAATGTCTGAGGCTACCAGGTTTATCACATAAA 1800
1801 AAACATTCAGTAAAATAGTAAGTTTCTCTTTTCTTCAGGTGCATTTTCCTACACCTCCAA 1860
1861 ATGAGGAATGGATTTTCTTTAATGTAAGAAGAATCATTTTTCTAGAGGTTGGCTTTCAAT 1920
1921 TCTGTAGCATACTTGGAGAAACTGCATTATCTTAAAAGGCAGTCAAATGGTGTTTGTTTT 1980
1981 TATCAAAATGTCAAAATAACATACTTGGAGAAGTATGTAATTTTGTCTTTGGAAAATTAC 2040
2041 AACACTGCCTTTGCAACACTGCAGTTTTTATGGTAAAATAATAGAAATGATCGACTCTAT 2100
2101 CAATATTGTATAAAAAGACTGAAACAATGCATTTATATAATATGTATACAATATTGTTTT 2160
2161 GTAAATAAGTGTCTCCTTTTTTATTTACTTTGGTATATTTTTACACTAAGGACATTTCAA 2220
2221 ATTAAGTACTAAGGCACAAAGACATGTCATGCATCACAGAAAAGCAACTACTTATATTTC 2280
2281 AGAGCAAATTAGCAGATTAAATAGTGGTCTTAAAACTCCATATGTTAATGATTAGATGGT 2340
2341 TATATTACAATCATTTTATATTTTTTACATGATTAACATTCACTTATGGATTCATGATG 2400
2401 GCTGTATAAAGTGAATTTGAAATTTCAATGGTTTACTGTCATTGTGTTTAAATCTCAACG 2460
2461 TTCCATTATTTTAATACTTGCAAAAACATTACTAAGTATACCAAAATAATTGACTCTATT 2520
2521 ATCTGAAATGAAGAATAAACTGATGCTATCTCAACAATAACTGTTACTTTTATTTTATAA 2580
2581 TTTGATAATGAATATATTTCTGCATTTATTTACTTCTGTTTTGTAAATTGGGATTTTGTT 2640
2641 AATCAAATTTATTGTACTATGACTAAATGAAATTATTTCTTACATCTAATTTGTAGAAAC 2700
2701 AGTATAAGTTATATTAAAGTGTTTTCACATTTTTTTGAAAGAC    2743
```

Fig. 1D

```
1/1                                         31/11
ATG CAA AAA CTG CAA CTC TGT GTT TAT ATT TAC CTG TTT ATG CTG ATT GTT GCT GGT CCA
 M   Q   K   L   Q   L   C   V   Y   I   Y   L   F   M   L   I   V   A   G   P
61/21                                       91/31
GTG GAT CTA AAT GAG AAC AGT GAG CAA AAA GAA AAT GTG GAA AAA GAG GGG CTG TGT AAT
 V   D   L   N   E   N   S   E   Q   K   E   N   V   E   K   E   G   L   C   N
121/41                                      151/51
GCA TGT ACT TGG AGA CAA AAC ACT AAA TCT TCA AGA ATA GAA GCC ATT AAA ATA CAA ATC
 A   C   T   W   R   Q   N   T   K   S   S   R   I   E   A   I   K   I   Q   I
181/61                                      211/71
CTC AGT AAA CTT CGT CTG GAA ACA GCT CCT AAC ATC AGC AAA GAT GCT ATA AGA CAA CTT
 L   S   K   L   R   L   E   T   A   P   N   I   S   K   D   A   I   R   Q   L
241/81                                      271/91
TTA CCC AAA GCT CCT CCA CTC CGG GAA CTG ATT GAT CAG TAT GAT GTC CAG AGG GAT GAC
 L   P   K   A   P   P   L   R   E   L   I   D   Q   Y   D   V   Q   R   D   D
301/101                                     331/111
AGC AGC GAT GGC TCT TTG GAA GAT GAC GAT TAT CAC GCT ACA ACG GAA ACA ATC ATT ACC
 S   S   D   G   S   L   E   D   D   D   Y   H   A   T   T   E   T   I   I   T
361/121                                     391/131
ATG CCT ACA GAG TCT GAT TTT TTA ATG CAA GTG GAT GGA AAA CCC AAA TGT TGC TTC TTT
 M   P   T   E   S   D   F   L   M   Q   V   D   G   K   P   K   C   C   F   F
421/141                                     451/151
AAA TTT AGC TCT AAA ATA CAA TAC AAT AAA GTG GTA AAG GCC CAA CTA TGG ATA TAT TTG
 K   F   S   S   K   I   Q   Y   N   K   V   V   K   A   Q   L   W   I   Y   L
481/161                                     511/171
AGA CCC GTC GAG ACT CCT ACA ACA GTG TTT GTG CAA ATC CTG AGA CTC ATC AAA CCT ATG
 R   P   V   E   T   P   T   T   V   F   V   Q   I   L   R   L   I   K   P   M
541/181                                     571/191
AAA GAC GGT ACA AGG TAT ACT GGA ATC CGA TCT CTG AAA CTT GAC ATG AAC CCA GGC ACT
 K   D   G   T   R   Y   T   G   I   R   S   L   K   L   D   M   N   P   G   T
601/201                                     631/211
GGT ATT TGG CAG AGC ATT GAT GTG AAG ACA GTG TTG CAA AAT TGG CTC AAA CAA CCT GAA
 G   I   W   Q   S   I   D   V   K   T   V   L   Q   N   W   L   K   Q   P   E
661/221                                     691/231
TCC AAC TTA GGC ATT GAA ATA AAA GCT TTA GAT GAG AAT GGT CAT GAT CTT GCT GTA ACC
 S   N   L   G   I   E   I   K   A   L   D   E   N   G   H   D   L   A   V   T
721/241                                     751/251
TTC CCA GGA CCA GGA GAA GAT GGG CTG AAT CCC TTT TTA GAG GTC AAG GTA ACA GAC ACA
 F   P   G   P   G   E   D   G   L   N   P   F   L   E   V   K   V   T   D   T
781/261                                     811/271
CCA AAA AGA TCC AGA AGG GAT TTT GGT CTT GAC TGT GAT GAG CAC TCA ACA GAA TCG CGA
 P   K   R   S   R   R   D   F   G   L   D   C   D   E   H   S   T   E   S   R
841/281                                     871/291
TGC TGT CGT TAC CCT CTA ACT GTG GAT TTT GAA GCT CTT GGA TGG GAT TGG ATT ATC GCT
 C   C   R   Y   P   L   T   V   D   F   E   A   L   G   W   D   W   I   I   A
901/301                                     931/311
CCT AAA AGA TAT AAG GCC AAT TAC TGC TCT GGA GAG TGT GAA TTT GTA TTT TTA CAA AAA
 P   K   R   Y   K   A   N   Y   C   S   G   E   C   E   F   V   F   L   Q   K
961/321                                     991/331
TAT CCT CAT ACT CAT CTG GTA CAC CAA GCA AAC CCC AGA GGT TCA GCA GGC CCT TGC TGT
 Y   P   H   T   H   L   V   H   Q   A   N   P   R   G   S   A   G   P   C   C
1021/341                                    1051/351
ACT CCC ACA AAG ATG TCT CCA ATT AAT ATG CTA TAT TTT AAT GGC AAA GAA CAA ATA ATA
 T   P   T   K   M   S   P   I   N   M   L   Y   F   N   G   K   E   Q   I   I
1081/361                                    1111/371
TAT GGG AAA ATT CCA GCC ATG GTA GTA GAC CGC TGC GGG TGC TCA TGA
 Y   G   K   I   P   A   M   V   V   D   R   C   G   C   S   *
```

Baboon GDF-8

Fig. 2A

```
1/1                                       31/11
ATG CAA AAA CTG CAA ATC TCT GTT TAT ATT   TAC CTA TTT ATG CTG ATT GTT GCT GGC CCA
 M   Q   K   L   Q   I   S   V   Y   I     Y   L   F   M   L   I   V   A   G   P
61/21                                     91/31
GTG GAT CTG AAT GAG AAC AGC GAG CAG AAG   GAA AAT GTG GAA AAA GAG GGG CTG TGT AAT
 V   D   L   N   E   N   S   E   Q   K     E   N   V   E   K   E   G   L   C   N
121/41                                    151/51
GCA TGT TTG TGG AGG GAA AAC ACT ACA TCC   TCA AGA CTA GAA GCC ATA AAA ATC CAA ATC
 A   C   L   W   R   E   N   T   T   S     S   R   L   E   A   I   K   I   Q   I
181/61                                    211/71
CTC AGT AAA CTT CGC CTG GAA ACA GCT CCT   AAC ATC AGC AAA GAT GCT ATC AGA CAA CTT
 L   S   K   L   R   L   E   T   A   P     N   I   S   K   D   A   I   R   Q   L
241/81                                    271/91
TTG CCC AAG GCT CCT CCA CTC CTG GAA CTG   ATT GAT CAG TTC GAT GTC CAG AGA GAT GCC
 L   P   K   A   P   P   L   L   E   L     I   D   Q   F   D   V   Q   R   D   A
301/101                                   331/111
AGC AGT GAC GGC TCC TTG GAA GAC GAT GAC   TAC CAC GCC AGG ACG GAA ACG GTC ATT ACC
 S   S   D   G   S   L   E   D   D   D     Y   H   A   R   T   E   T   V   I   T
361/121                                   391/131
ATG CCC ACG GAG TCT GAT CTT CTA ACG CAA   GTG GAA GGA AAA CCC AAA TGT TGC TTC TTT
 M   P   T   E   S   D   L   L   T   Q     V   E   G   K   P   K   C   C   F   F
421/141                                   451/151
AAA TTT AGC TCT AAG ATA CAA TAC AAT AAA   CTA GTA AAG GCC CAA CTG TGG ATA TAT CTG
 K   F   S   S   K   I   Q   Y   N   K     L   V   K   A   Q   L   W   I   Y   L
481/161                                   511/171
AGG CCT GTC AAG ACT CCT GCG ACA GTG TTT   GTG CAA ATC CTG AGA CTC ATC AAA CCC ATG
 R   P   V   K   T   P   A   T   V   F     V   Q   I   L   R   L   I   K   P   M
541/181                                   571/191
AAA GAC GGT ACA AGG TAT ACT GGA ATC CGA   TCT CTG AAA CTT GAC ATG AAC CCA GGC ACT
 K   D   G   T   R   Y   T   G   I   R     S   L   K   L   D   M   N   P   G   T
601/201                                   631/211
GGT ATT TGG CAG AGC ATT GAT GTG AAG ACA   GTG TTG CAG AAC TGG CTC AAA CAA CCT GAA
 G   I   W   Q   S   I   D   V   K   T     V   L   Q   N   W   L   K   Q   P   E
661/221                                   691/231
TCC AAC TTA GGC ATT GAA ATC AAA GCT TTA   GAT GAG AAT GGC CAT GAT CTT GCT GTA ACC
 S   N   L   G   I   E   I   K   A   L     D   E   N   G   H   D   L   A   V   T
721/241                                   751/251
TTC CCA GAA CCA GGA GAA GAT GGA CTG ACT   CCT TTT TTA GAA GTC AAG GTA ACA GAC ACA
 F   P   E   P   G   E   D   G   L   T     P   F   L   E   V   K   V   T   D   T
781/261                                   811/271
CCA AAA AGA TCT AGG AGA GAT TTT GGG CTT   GAT TGT GAT GAA CAC TCC ACA GAA TCT CGA
 P   K   R   S   R   R   D   F   G   L     D   C   D   E   H   S   T   E   S   R
841/281                                   871/291
TGC TGT CGT TAC CCT CTA ACT GTG GAT TTT   GAA GCT TTT GGA TGG GAT TGG ATT ATT GCA
 C   C   R   Y   P   L   T   V   D   F     E   A   F   G   W   D   W   I   I   A
901/301                                   931/311
CCT AAA AGA TAT AAG GCC AAT TAC TGC TCT   GGA GAA TGT GAA TTT GTA TTT TTG CAA AAG
 P   K   R   Y   K   A   N   Y   C   S     G   E   C   E   F   V   F   L   Q   K
961/321                                   991/331
TAT CCT CAT ACC CAT CTT GTG CAC CAA GCA   AAC CCC AGA GGT CA GCC GGC CCC TGC TGT
 Y   P   H   T   H   L   V   H   Q   A     N   P   R   G   S   A   G   P   C   C
1021/341                                  1051/351
ACT CCT ACA AAG ATG TCT CCA ATT AAT ATG   CTA TAT TTT AAT GGC AAA GGA CAA ATA ATA
 T   P   T   K   M   S   P   I   N   M     L   Y   F   N   G   K   G   Q   I   I
1081/361                                  1111/371
TAC GGG AAG ATT CCA GCC ATG GTA GTA GAT   CGC TGT GGG TGT TCA TGA
 Y   G   K   I   P   A   M   V   V   D     R   C   G   C   S   *
```

Bovine GDF-8

Fig. 2B

```
1/1                                             31/11
ATG CAA AAG CTA GCA GTC TAT GTT TAT ATT TAC CTG TTC ATG CAG ATC GCG GTT GAT CCG
 M   Q   K   L   A   V   Y   V   Y   I   Y   L   F   M   Q   I   A   V   D   P
61/21                                           91/31
GTG GCT CTG GAT GGC AGT AGT CAG CCC ACA GAG AAC GCT GAA AAA GAC GGA CTG TGC AAT
 V   A   L   D   G   S   S   Q   P   T   E   N   A   E   K   D   G   L   C   N
121/41                                          151/51
GCT TGT ACG TGG AGA CAG AAT ACA AAA TCC TCC AGA ATA GAA GCC ATA AAA ATT CAA ATC
 A   C   T   W   R   Q   N   T   K   S   S   R   I   E   A   I   K   I   Q   I
181/61                                          211/71
CTC AGC AAA CTG CGC CTG GAA CAA GCA CCT AAC ATT AGC AGG GAC GTT ATT AAG CAG CTT
 L   S   K   L   R   L   E   Q   A   P   N   I   S   R   D   V   I   K   Q   L
241/81                                          271/91
TTA CCC AAA GCT CCT CCA CTG CAG GAA CTG ATT GAT CAG TAT GAT GTC CAG AGG GAC GAC
 L   P   K   A   P   P   L   Q   E   L   I   D   Q   Y   D   V   Q   R   D   D
301/101                                         331/111
AGT AGC GAT GGC TCT TTG GAA GAC GAT GAC TAT CAT GCC ACA ACC GAG ACG ATT ATC ACA
 S   S   D   G   S   L   E   D   D   D   Y   H   A   T   T   E   T   I   I   T
361/121                                         391/131
ATG CCT ACG GAG TCT GAT TTT CTT GTA CAA ATG GAG GGA AAA CCA AAA TGT TGC TTC TTT
 M   P   T   E   S   D   F   L   V   Q   M   E   G   K   P   K   C   C   F   F
421/141                                         451/151
AAG TTT AGC TCT AAA ATA CAA TAT AAC AAA GTA GTA AAG GCA CAA TTA TGG ATA TAC TTG
 K   F   S   S   K   I   Q   Y   N   K   V   V   K   A   Q   L   W   I   Y   L
481/161                                         511/171
AGG CAA GTC CAA AAA CCT ACA ACG GTG TTT GTG CAG ATC CTG AGA CTC ATT AAG CCC ATG
 R   Q   V   Q   K   P   T   T   V   F   V   Q   I   L   R   L   I   K   P   M
541/181                                         571/191
AAA GAC GGT ACA AGA TAT ACT GGA ATT CGA TCT TTG AAA CTT GAC ATG AAC CCA GGC ACT
 K   D   G   T   R   Y   T   G   I   R   S   L   K   L   D   M   N   P   G   T
601/201                                         631/211
GGT ATC TGG CAG AGT ATT GAT GTG AAG ACA GTG CTG CAA AAT TGG CTC AAA CAG CCT GAA
 G   I   W   Q   S   I   D   V   K   T   V   L   Q   N   W   L   K   Q   P   E
661/221                                         691/231
TCC AAT TTA GGC ATC GAA ATA AAA GCT TTT GAT GAG ACT GGA CGA GAT CTT GCT GTC ACA
 S   N   L   G   I   E   I   K   A   F   D   E   T   G   R   D   L   A   V   T
721/241                                         751/251
TTC CCA GGA CCG GGT GAA GAT GGA TTG AAC CCA TTT TTA GAG GTC AGA GTT ACA GAC ACA
 F   P   G   P   G   E   D   G   L   N   P   F   L   E   V   R   V   T   D   T
781/261                                         811/271
CCG AAA CGG TCC CGC AGA GAT TTT GCC CTT GAC TGT GAT GAG CAC TCA ACG GAA TCC CGA
 P   K   R   S   R   R   D   F   G   L   D   C   D   E   H   S   T   E   S   R
841/281                                         871/291
TGT TGT CGC TAC CCG CTG ACA GTG GAT TTC GAA GCT TTT GGA TGG GAC TGG ATT ATA GCA
 C   C   R   Y   P   L   T   V   D   F   E   A   F   G   W   D   W   I   I   A
901/301                                         931/311
CCT AAA AGA TAC AAA GCC AAT TAC TGC TCC GGA GAA TGC GAA TTT GTG TTT CTA CAG AAA
 P   K   R   Y   K   A   N   Y   C   S   G   E   C   E   F   V   F   L   Q   K
961/321                                         991/331
TAC CCG CAC ACT CAC CTG GTA CAC CAA GCA AAT CCC AGA GGC TCA GCA GGC CCT TGC TGC
 Y   P   H   T   H   L   V   H   Q   A   N   P   R   G   S   A   G   P   C   C
1021/341                                        1051/351
ACA CCC ACC AAG ATG TCC CCT ATA AAC ATG CTG TAT TTC AAT GGA AAA GAA CAA ATA ATA
 T   P   T   K   M   S   P   I   N   M   L   Y   F   N   G   K   E   Q   I   I
1081/361                                        1111/371
TAT GGA AAG ATA CCA GCC ATG GTT GTA GAT CGT TGC GGG TGC TCA TGA
 Y   G   K   I   P   A   M   V   V   D   R   C   G   C   S   *
```

Chicken GDF-8

Fig. 2C

```
1/1                                       31/11
ATG ATT CAA AAA CCG CAA ATG TAT GTT TAT ATT TAC CTG TTT GTG CTG ATT GCT GCT GGC
 M   I   Q   K   P   Q   M   Y   V   Y   I   Y   L   F   V   L   I   A   A   G
61/21                                     91/31
CCA GTG GAT CTA AAT GAG GAC AGT GAG AGA GAG GCG AAT GTG GAA AAA GAG GGG CTG TGT
 P   V   D   L   N   E   D   S   E   R   E   A   N   V   E   K   E   G   L   C
121/41                                    151/51
AAT GCG TGT GCG TGG AGA CAA AAC ACA AGG TAC TCC AGA ATA GAA GCC ATA AAA ATT CAA
 N   A   C   A   W   R   Q   N   T   R   Y   S   R   I   E   A   I   K   I   Q
181/61                                    211/71
ATC CTC AGT AAA CTC CGC CTG GAA ACA GCG CCT AAC ATC AGC AAA GAT GCT ATA AGA CAA
 I   L   S   K   L   R   L   E   T   A   P   N   I   S   K   D   A   I   R   Q
241/81                                    271/91
CTT CTG CCC AGA GCG CCT CCA CTC CGG GAA CTG ATC GAT CAG TAC GAC GTC CAG ACG GAT
 L   L   P   R   A   P   P   L   R   E   L   I   D   Q   Y   D   V   Q   R   D
301/101                                   331/111
GAC AGC AGT GAC GGC TCT TTG GAA GAT GAC GAT TAT CAC GCT ACC ACG GAA ACA ATC ATT
 D   S   S   D   G   S   L   E   D   D   D   Y   H   A   T   T   E   T   I   I
361/121                                   391/131
ACC ATG CCT ACC GAG TCT GAC TTT CTA ATG CAA GCG GAT GGA AAG CCC AAA TGT TGC TTT
 T   M   P   T   E   S   D   F   L   M   Q   A   D   G   K   P   K   C   C   F
421/141                                   451/151
TTT AAA TTT AGC TCT AAA ATA CAG TAC AAC AAA GTG GTA AAG GCC CAG CTG TGG ATA TAT
 F   K   F   S   S   K   I   Q   Y   N   K   V   V   K   A   Q   L   W   I   Y
481/161                                   511/171
CTG AGA GCC GTC AAG ACT CCT ACA ACA GTG TTT GTG CAA ATC CTG AGA CTC ATC AAA CCC
 L   R   A   V   K   T   P   T   T   V   F   V   Q   I   L   R   L   I   K   P
541/181                                   571/191
ATG AAA GAC GGT ACA AGG TAT ACC GGA ATC CGA TCT CTG AAA CTT GAC ATG AGC CCA GGC
 M   K   D   G   T   R   Y   T   G   I   R   S   L   K   L   D   M   S   P   G
601/201                                   631/211
ACT GGT ATT TGG CAG AGT ATT GAT GTG AAG ACA GTG TTG CAA AAT TGG CTC AAA CAG CCT
 T   G   I   W   Q   S   I   D   V   K   T   V   L   Q   N   W   L   K   Q   P
661/221                                   691/231
GAA TCC AAC TTA GGC ATT GAA ATC AAA GCT TTG GAT GAG AAT GGG CAT GAT CTT GCT GTA
 E   S   N   L   G   I   E   I   K   A   L   D   E   N   G   H   D   L   A   V
721/241                                   751/251
ACC TTC CCA GGA CCA GGA GAA GAT GGG CTG AAT CCC TTT TTA GAA GTC AAA GTA ACA GAC
 T   F   P   G   P   G   E   D   G   L   N   P   F   L   E   V   K   V   T   D
781/261                                   811/271
ACA CCC AAG AGG TCC CGG AGA GAC TTT GGG CTT GAC TGT GAT GAA CAC TCC ACG GAA TCG
 T   P   K   R   S   R   R   D   F   G   L   D   C   D   E   H   S   T   E   S
841/281                                   871/291
CGG TGC TGT CGC TAC CCC CTC ACG GTC GAT TTC GAA GCC TTT GGA TGG GAC TGG ATT ATT
 R   C   C   R   Y   P   L   T   V   D   F   E   A   F   G   W   D   W   I   I
901/301                                   931/311
GCA CCC AAA AGA TAT AAG GCT AAT TAC TGC TCT GGA GAG TGT GAA TTT GTG TTC TTA CAA
 A   P   K   R   Y   K   A   N   Y   C   S   G   E   C   E   F   V   F   L   Q
961/321                                   991/331
AAA TAT CCC CAT ACT CAT CTT GTG CAC CAA GCA AAC CCC AGA GGC TCG GCA GGC CCT TGC
 K   Y   P   H   T   H   L   V   H   Q   A   N   P   R   G   S   A   G   P   C
1021/341                                  1051/351
TGC ACG CCA ACA AAA ATG TCT CCC ATT AAT ATG CTA TAT TTT AAT GGC AAA GAA CAA ATA
 C   T   P   T   K   M   S   P   I   N   M   L   Y   F   N   G   K   E   Q   I
1081/361                                  1111/371
ATA TAT GGC AAA ATT CCA GCC ATG GTA GTA GAC CGG TGT GGG TGC TCG TGA
 I   Y   G   K   I   P   A   M   V   V   D   R   C   G   C   S   *
```

Rat GDF-8

Fig. 2D

```
1/1                                         31/11
ATG CAA AAG CTA GCA GTC TAT GTT TAT ATT TAC CTG TTC ATG CAG ATT TTA GTT CAT CCG
 M   Q   K   L   A   V   Y   V   Y   I   Y   L   F   M   Q   I   L   V   H   P
61/21                                       91/31
CTG GCT CTT GAT GGC ACT AGT CAG CCC ACA GAG AAC GCT GAA AAA GAC GGA CTG TGC AAT
 V   A   L   D   G   S   S   Q   P   T   E   N   A   E   K   D   G   L   C   N
121/41                                      151/51
GCT TGC ACG TGG AGA CAG AAT ACT AAA TCC TCC AGA ATA GAA GCC ATA AAA ATT CAA ATC
 A   C   T   W   R   Q   N   T   K   S   S   R   I   E   A   I   K   I   Q   I
181/61                                      211/71
CTC AGC AAA CTG CGC CTG GAA CAA GCA CCT AAC ATT AGC AGG GAC GTT ATT AAA CAA CTT
 L   S   K   L   R   L   E   Q   A   P   N   I   S   R   D   V   I   K   Q   L
241/81                                      271/91
TTA CCC AAA GCT CCT CCG CTG CAG GAA CTG ATT GAT CAG TAT GAC GTC CAG AGA GAC GAC
 L   P   K   A   P   P   L   Q   E   L   I   D   Q   Y   D   V   Q   R   D   D
301/101                                     331/111
AGT AGC GAT GGC TCT TTC GAA GAC GAT GAC TAT CAT GCC ACA ACC AAA ACG ATT ATC ACA
 S   S   D   G   S   L   E   D   D   D   Y   H   A   T   T   E   T   I   I   T
361/121                                     391/131
ATG CCT ACG GAG TCT GAT TTT CTT GTA CAA ATG GAG GGA AAA CCA AAA TGT TGC TTC TTT
 M   P   T   E   S   D   F   L   V   Q   M   E   G   K   P   K   C   C   F   F
421/141                                     451/151
AAG TTT AGC TCT AAA ATA CAA TAT AAC AAA GTA GTA AAG GCA CAA TTA TGG ATA TAC TTG
 K   F   S   S   K   I   Q   Y   N   K   V   V   K   A   Q   L   W   I   Y   L
481/161                                     511/171
AGG CAA GTC CAA AAA CCT ACA ACG GTG TTT GTC CAG ATC CTC AGA CTC ATT AAA CCC ATG
 R   Q   V   Q   K   P   T   T   V   F   V   Q   I   L   R   L   I   K   P   M
541/181                                     571/191
AAA GAC GGT ACA AGA TAT ACT GGA ATT CGA TCT TTG AAA CTT GAC ATG AAC CCA GGC ACT
 K   D   G   T   R   Y   T   G   I   R   S   L   K   L   D   M   N   P   G   T
601/201                                     631/211
GGT ATC TGG CAG AGT ATT GAT GTC AAC ACA GTG TTG CAA AAT TGG CTC AAA CAG CCT GAA
 G   I   W   Q   S   I   D   V   N   T   V   L   Q   N   W   L   K   Q   P   E
661/221                                     691/231
TCC AAT TTA GGC ATC GAA ATA AAA GCT TTT GAT GAG AAT GGA CGA GAT CTT GCT GTA ACA
 S   N   L   G   I   E   I   K   A   F   D   E   N   G   R   D   L   A   V   T
721/241                                     751/251
TTC CCA GGA CCA GGT GAA GAT GGA CTG AAC CCA TTT TTA GAG GTC AGA GTT ACA GAC ACA
 F   P   G   P   G   E   D   G   L   N   P   F   L   E   V   R   V   T   D   T
781/261                                     811/271
CCA AAA CGG TCC CGC ACA GAT TTT GGC CTT GAC TGC GAC GAG CAC TCA ACG GAA TCT CGA
 P   K   R   S   R   T   D   F   G   L   D   C   D   E   H   S   T   E   S   R
841/281                                     871/291
TGT TGT CGC TAC CCG CTC ACA GTG GAT TTT GAA GCT TTT GGA TGG GAC TGG ATT ATA GCA
 C   C   R   Y   P   L   T   V   D   F   E   A   F   G   W   D   W   I   I   A
901/301                                     931/311
CCT AAA AGA TAC AAA GCC AAT TAC TGC TCT GGA GAA TGT GAA TTC GTA TTT CTA CAG AAA
 P   K   R   Y   K   A   N   Y   C   S   G   E   C   E   F   V   F   L   Q   K
961/321                                     991/331
TAC CCG CAC ACT CAC CTG GTA CAC CAA GCA AAT CCA AGA GGC TCA GCA GGC CCT TGC TGC
 Y   P   H   T   H   L   V   H   Q   A   N   P   R   G   S   A   G   P   C   C
1021/341                                    1051/351
ACA CCC ACC AAG ATG TCC CCT ATA AAC ATG CTC TAT TTC AAT GGA AAA GAA CAA ATA ATA
 T   P   T   K   M   S   P   I   N   M   L   Y   F   N   G   K   E   Q   I   I
1081/361                                    1111/371
TAT GGA AAG ATA CCA GCC ATG GTT GTA GAT CGT TGC GGC TGC TCA TGA
 Y   G   K   I   P   A   M   V   V   D   R   C   G   C   S   *
```

Turkey GDF-8

Fig. 2E

```
   1 CCGCGGGACTCCGGCGTCCCCGCCCCCAGTCCTCCCTCCCCTCCCCTCCAGCATGGTGC    60
                                                         M  V  L
  61 TCGCGGCCCCGCTGCTGCTGGGCTTCCTGCTCCTCGCCCTGGAGCTGCGGCCCCGGGGG   120
      A  A  P  L  L  L  G  F  L  L  L  A  L  E  L  R  P  R  G  E
 121 AGGCGGCCGAGGGCCCCGCGGCGGCGGCGGCGGCGGCGGCGGCGGCAGCGGCGGGGG    180
      A  A  E  G  P  A  A  A  A  A  A  A  A  A  A  A  A  G  V
 181 TCGGGGGGGAGCGCTCCAGCCGGCCAGCCCCGTCCGTGGCGCCCGAGCCGGACGGCTGCC   240
      G  G  E  R  S  S  R  P  A  P  S  V  A  P  E  P  D  G  C  P
 241 CCGTGTGCGTTTGGCGGCAGCACAGCCGCCAGCTGCGCCTAGAGAGCATCAAGTCGCAGA   300
      V  C  V  W  R  Q  H  S  R  E  L  R  L  E  S  I  K  S  Q  I
 301 TCTTGAGCAAACTGCGGCTCAAGGAGGCGCCCAACATCAGCCGCGAGGTGGTGAAGCAGC   360
      L  S  K  L  R  L  K  E  A  P |N  I  S| R  E  V  V  K  Q  L
 361 TGCTGCCCAAGGCGCCGCCGCTGCAGCAGATCCTGGACCTACACGACTTCCAGGGCGACG   420
      L  P  K  A  P  P  L  Q  Q  I  L  D  L  H  D  F  Q  G  D  A
 421 CGCTGCAGCCCGAGGACTTCCTGGAGGAGGACGAGTACCACGCCACCACCGAGACCGTCA   480
      L  Q  P  E  D  F  L  E  E  D  E  Y  H  A  T  T  E  T  V  I
 481 TTAGCATGGCCCAGGAGACGGACCCAGCAGTACAGACAGATGGCAGCCCTCTCTGCTGCC   540
      S  M  A  Q  E  T  D  P  A  V  Q  T  D  G  S  P  L  C  C  H
 541 ATTTTCACTTCAGCCCCAAGGTGATGTTCACAAAGGTACTGAAGGCCCAGCTGTGGGTGT   600
      F  H  F  S  P  K  V  M  F  T  K  V  L  K  A  Q  L  W  V  Y
 601 ACCTACGGCCTGTACCCGCCCAGCCACAGTCTACCTGCAGATCTTGCGACTAAAACCCC    660
      L  R  P  V  P  R  P  A  T  V  Y  L  Q  I  L  R  L  K  P  L
 661 TAACTGGGGAAGGGACCGCAGGGGGAGGGGGCGGAGGCCGGCGTCACATCCGTATCCGCT   720
      T  G  E  G  T  A  G  G  G  G  G  R  R  H  I  R  I  R  S
 721 CACTGAAGATTGAGCTGCACTCACGCTCAGGCCATTGGCAGAGCATCGACTTCAAGCAAG   780
      L  K  I  E  L  H  S  R  S  G  H  W  Q  S  I  D  F  K  Q  V
 781 TGCTACACAGCTGGTTCCGCCAGCCACAGAGCAACTGGGGCATCGAGATCAACGCCTTTG   840
      L  H  S  W  F  R  Q  P  Q  S  N  W  G  I  E  I  N  A  F  D
 841 ATCCCAGTGGCACAGACCTGGCTGTCACCTCCCTGGGGCCGGGAGCCGAGGGGCTGCATC   900
      P  S  G  T  D  L  A  V  T  S  L  G  P  G  A  E  G  L  H  P
 901 CATTCATGGAGCTTCGAGTCCTAGAGAACACAAAACGTTCCCGGCGGAACCTGGGTCTGG   960
      F  M  E  L  R  V  L  E  N  T  K |R  S  R  R| N  L  G  L  D
 961 ACTGCGACGAGCACTCAAGCGAGTCCCGCTGCTGCCGATATCCCCTCACAGTGGACTTTG  1020
      C  D  E  H  S  S  E  S  R  C  C  R  Y  P  L  T  V  D  F  E
1021 AGGCTTTCGGCTGGGACTGGATCATCGCACCTAAGCGCTACAAGGCCAACTACTGCTCCG  1080
      A  F  G  W  D  W  I  I  A  P  K  R  Y  K  A  N  Y  C  S  G
1081 GCCAGTGCGAGTACATGTTCATGCAAAAATATCCGCATACCCATTTGGTGCAGCAGGCCA  1140
      Q  C  E  Y  M  F  M  Q  K  Y  P  H  T  H  L  V  Q  Q  A  N
1141 ATCCAAGAGGCTCTGCTGGGCCCTGTTGTACCCCCACCAAGATGTCCCCAATCAACATGC  1200
      P  R  G  S  A  G  P  C  C  T  P  T  K  M  S  P  I  N  M  L
1201 TCTACTTCAATGACAAGCAGCAGATTATCTACGGCAAGATCCCTGGCATGGTGGTGGATC  1260
      Y  F  N  D  K  Q  Q  I  I  Y  G  K  I  P  G  M  V  V  D  R
1261 GCTGTGGCTGCTCTTAAGTGGGTCACTACAAGCTGCTGGAGCAAAGACTTGGTGGGTGGG  1320
      C  G  C  S  *
1321 TAACTTAACCTCTTCACAGAGGATAAAAAAATGCTTGTGAGTATGACAGAAGGGAATAAAC  1380
1381 AGGCTTAAAGGGT 1393
```

Fig. 4A

| # of normal size kidneys | 2 | 1 | 1 | 0 | 0 | 0 |
|---|---|---|---|---|---|---|
| # of small kidneys | 0 | 1 | 0 | 2 | 1 | 0 |

| | | | | | | |
|---|---|---|---|---|---|---|
| +/+ | 47 | 0 | 0 | 0 | 0 | 0 |
| +/− | 88 | 0 | 5 | 0 | 0 | 0 |
| −/− | 2 | 2 | 9 | 3 | 3 | 28 |

Fig. 13

Fig. 15 Anterior transformations in wild-type, heterozygous and homozygous GDF-11 mice

| | Wild-type | | Heterozygous | | Homozygous | |
|---|---|---|---|---|---|---|
| | Hybrid | 129/SvJ | Hybrid | 129/SvJ | Hybrid | 129/SvJ |
| Presacral vertebrae[a] | | | | | | |
| 25 | 4 | 1 | - | - | - | - |
| 26 | 18 | 6 | 1 | - | - | - |
| 27 | - | - | 58 | 6 | - | - |
| 33 | - | - | - | - | 18 | 2 |
| 34 | - | - | - | - | 5 | - |
| Vertebral pattern[a,b] | | | | | | |
| C7 T13 L5 | 4 | 1 | - | - | - | - |
| C7 T13 L6 | 18 | 6 | - | - | - | - |
| C7 T13 L?[c] | - | 1 | - | - | - | - |
| C7 T14 L5 | - | - | 1 | - | - | - |
| C7 T14 L6 | - | - | 58 | 6 | - | - |
| C7 T17 L9 | - | - | - | - | 1 | 1 |
| C7 T18 L8 | - | - | - | - | 17 | 1 |
| C7 T18 L9 | - | - | - | - | 5 | - |
| C7 T18 L?[c] | - | - | - | - | - | 1 |
| Anterior tuberculus on | | | | | | |
| No vertebrae | - | 1 | - | - | - | - |
| C6 | 22 | 7 | 59 | 5 | 21 | 1 |
| C6 and C7[d] | - | - | - | 1 | 2 | 2 |
| Attached/unattached ribs[e] | | | | | | |
| 7/6 | 22 | 8 | - | - | - | - |
| 8/6 | - | - | 59 | 6 | - | - |
| 10/7 | - | - | - | - | - | 1 |
| 10/8[e] | - | - | - | - | 13 | 2 |
| 11/6 | - | - | - | - | 1 | - |
| 11/7 | - | - | - | - | 4 | - |
| 10 + 11/8 +7[f] | - | - | - | - | 5 | - |
| Longest spinous process on | | | | | | |
| T2 | 22 | 5 | 41 | - | 2 | - |
| T3 | - | - | 6 | 6 | 16 | - |
| T2 + T3 equal | - | 1 | 8 | - | 1 | - |
| T3 + T4 equal | - | - | - | - | - | 2 |
| Transitional spinous process on | | | | | | |
| T10 | 22 | 8 | 3 | - | - | - |
| T11 | - | - | 56 | 6 | - | - |
| T12 | - | - | - | - | 1 | - |
| T13 | - | - | - | - | 22 | 3 |
| Transitional articular process on[g] | | | | | | |
| T10 | 22 | 8 | 1 | - | - | - |
| T11 | - | - | 58 | 6 | - | - |
| T13 | - | - | - | - | 23 | 3 |

[a] Vertebrae that were lumbar on one side and sacral on the other were scored as sacral. These vertebrae were seen in 2 wild-type, 3 heterozygous and 8 homozygous mutants in the hybrid background.
[b] One hybrid heterozygous, 9 hybrid homozygous and 2 129/SvJ homozygous mutants had rudimentary ribs on the most caudal thoracic segment.
[c] The number of lumbar vertebrae could not be counted due to extensive fusion of lumbar segments.
[d] These animals had a unilateral transformation of the anterior tuberculi. One 129/SvJ homozygous mutant retained one tuberculus on C6 but had bilateral tuberculi on C7.
[e] One 129/SvJ homozygous mutant had the first rib attached to the second rather than the sternum on one side only. Ten ribs were attached to the sternum on the other side.
[f] Ribs were asymmetrically attached.
[g] One wild-type 129/SvJ had one transitional articular process on T10 and one on T11 (scored as T10). One hybrid heterozygous mutant mice had one process on T11 and one on T12 (scored as T11).

Fig. 15

METHODS TO IDENTIFY GROWTH DIFFERENTIATION FACTOR (GDF) BINDING PROTEINS

This application claims priority under 35 U.S.C. §119 to International Application No. PCT/US98/15598, filed Jul. 28, 1998, which claims priority to U.S. Ser. No. 60/054,461, filed Aug. 1, 1997.

FIELD OF THE INVENTION

This invention relates generally to ligand-receptor interactions and more specifically to growth differentiation factor receptor proteins and the ligands that bind to such receptors and methods of use therefor.

DESCRIPTION OF RELATED ART

The transforming growth factor β (TGF-β) superfamily encompasses a group of structurally-related proteins which affect a wide range of differentiation processes during embryonic development. The family includes, Mullerian inhibiting substance (MIS), which is required for normal male sex development (Behringer, et al., *Nature*, 345:167, 1990), Drosophila decapentaplegic (DPP) gene product, which is required for dorsal-ventral axis formation and morphogenesis of the imaginal disks (Padgett, et al., *Nature*, 325:81–84, 1987), the Xenopus Vg-1 gene product, which localizes to the vegetal pole of eggs ((Weeks, et al., *Cell*, 51:861–867, 1987), the activins (Mason, et al., *Biochem, Biophys. Res. Commun.*, 135:957–964, 1986), which can induce the formation of mesoderm and anterior structures in Xenopus embryos (Thomsen, et al., *Cell*, 63:485, 1990), and the bone morphogenetic proteins (BMPS, osteogenin, OP-1) which can induce de novo cartilage and bone formation (Sampath, et al., *J. Biol. Chem.*, 265:13198, 1990). The TGF-βs can influence a variety of differentiation processes, including adipogenesis, myogenesis, chondrogenesis, hematopolesis, and epithelial cell differentiation (for review, see Massague, *Cell* 49:437, 1987).

The proteins of the TGF-β family are initially synthesized as a large precursor protein which subsequently undergoes proteolytic cleavage at a cluster of basic residues approximately 110–140 amino acids from the C-terminus. The C-terminal regions, or mature regions, of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. Studies have shown that when the pro-region of a member of the TGF-β family is coexpressed with a mature region of another member of the TGF-β family, intracellular dimerization and secretion of biologically active homodimers occur (Gray, A. et al., *Science*, 247:1328, 1990). Additional studies by Hammonds, et al., (*Molec. Endocrin.* 5:149, 1991) showed that the use of the BMP-2 pro-region combined with the BMP-4 mature region led to dramatically improved expression of mature BMP-4. For most of the family members that have been studied, the homodimeric species has been found to be biologically active, but for other family members, like the inhibins (Ling, et al., *Nature*, 321 :779, 1986) and the TGF-βs (Cheifetz, et al., *Cell*, 48:409, 1987), heterodimers have also been detected, and these appear to have different biological properties than the respective homodimers.

The study of receptor-ligand interactions has revealed a great deal of information about how cells respond to external stimuli. This knowledge has led to the development of therapeutically important compounds, such as erythropoietin, colony stimulating factors and PDGF.

SUMMARY OF THE INVENTION

The present invention provides receptors for the growth differentiation factor (GDF) growth factor family. These receptors are useful for identifying antagonists and agonists for agricultural and human therapeutic purposes.

In a first embodiment, the invention provides a recombinant cell line that expresses growth differentiation factor-8 (GDF-8) or growth differentiation factor-11 (GDF-11) receptor polypeptide. Also included are antibodies that bind to GDF receptors, polynucleotides encoding the receptors and the GDF receptor proteins themselves.

Peptide fragments of GDF receptors, such as the GDF-8 or GDF-11 receptors, are also included. Such peptides may be useful in inhibiting binding of GDF-8 or GDF-11 to either its own receptor or another GDF-receptor (e.g., GDF-8 and -11 may bind the same receptor).

In another embodiment, the invention provides a substantially purified GDF-8-binding agent, wherein the binding agent inhibits GDF-8 binding to GDF-8 receptor. Such agents that inhibit GDF-11 binding are also included.

In yet another embodiment, the invention provides a method for identifying a GDF receptor polypeptide including incubating components such as GDF polypeptide and a cell expressing a receptor or a soluble receptor under conditions sufficient to allow the GDF to bind to the receptor; measuring the binding of the GDF polypeptide to the receptor; and isolating the receptor.

The invention also includes a method for identifying a compound that binds to GDF receptor polypeptide including incubating components comprising the compound and GDF polypeptide under conditions sufficient to allow the components to interact and measuring the binding or effect of binding of the compound to GDF receptor polypeptide.

The invention also provides non-human transgenic animals that have a phenotype characterized by expression of GDF-receptor polypeptide, the phenotype being conferred by a transgene contained in the somatic and germ cells of the animal, the transgene comprising a nucleic acid sequence which encodes GDF-receptor polypeptide. Methods of producing such transgenic animals are also included.

In another embodiment, the invention includes a method for inhibiting the expression of GDF-receptor in a cell including contacting GDF-receptor with an inhibiting effective amount of an antisense oligonucleotide that binds to a segment of an mRNA transcribed from a GDF-receptor gene, whereby the binding of the antisense to the mRNA segment inhibits GDF-receptor expression.

BRIEF DESCRIPTION OF THE FIGURES

FIGS. 1a and 1b are the nucleotide (SEQ ID NO:1) and amino acid (SEQ ID NO:2) sequences of murine GDF-8.

FIGS. 1c and 1d are the nucleotide (SEQ ID NO:3) and amino acid (SEQ ID NO:4) sequences of human GDF-8.

FIGS. 2a–2e are the nucleotide and amino acid sequences of baboon GDF-8 (SEQ ID NOS:5 and 6, respectively), bovine GDF-8 (SEQ ID NOS:7 and 8, respectively), chicken GDF-8 (SEQ ID NOS:9 and 10, respectively), rat GDF-8 (SEQ ID NOS:11 and 12, respectively), and turkey GDF-8 (SEQ ID NOS:13 and 14, respectively).

FIGS. 4a and 4b show the nucleotide (SEQ ID NO:15) and amino acid (SEQ ID NO:16) sequences of murine GDF-11 and expression of GDF-11, respectively.

FIG. 13 shows kidney abnormalities in GDF-11 knockout mice. Kidneys of newborn animals were examined and classified according to the number of normal sized or small kidneys as shown at the top. Numbers in the table indicate number of animals falling into each classification according to genotype.

FIG. 15 is a table summarizing anterior transformations in wild-type, heterozygous and homozygous GDF-11 mice.

DETAILED DESCRIPTION OF THE INVENTION

Figure 3A:
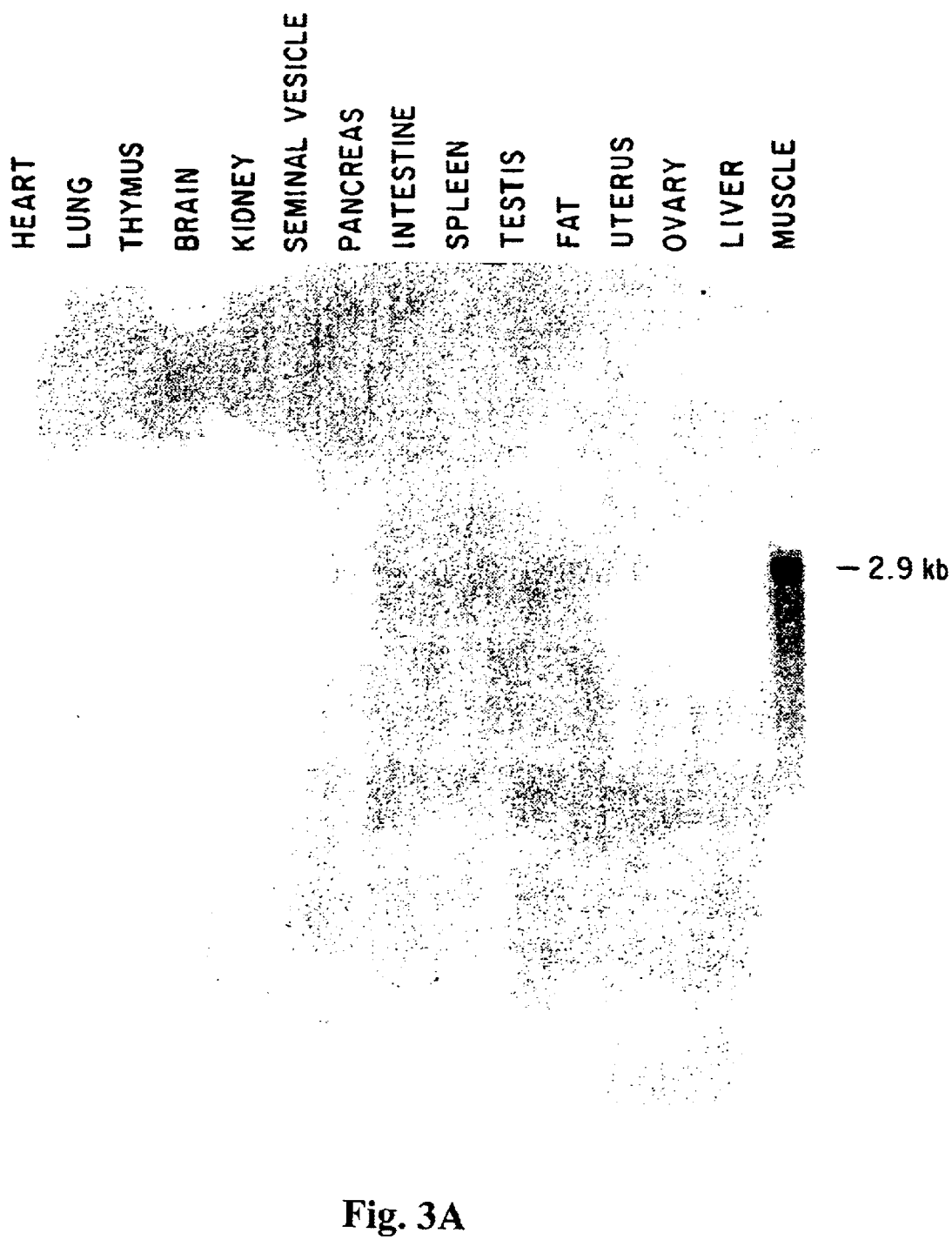
FIGS. 3a and 3b are Northern blots showing expression of GDF-8 in muscle and in various species, respectively.
Figure 3B:
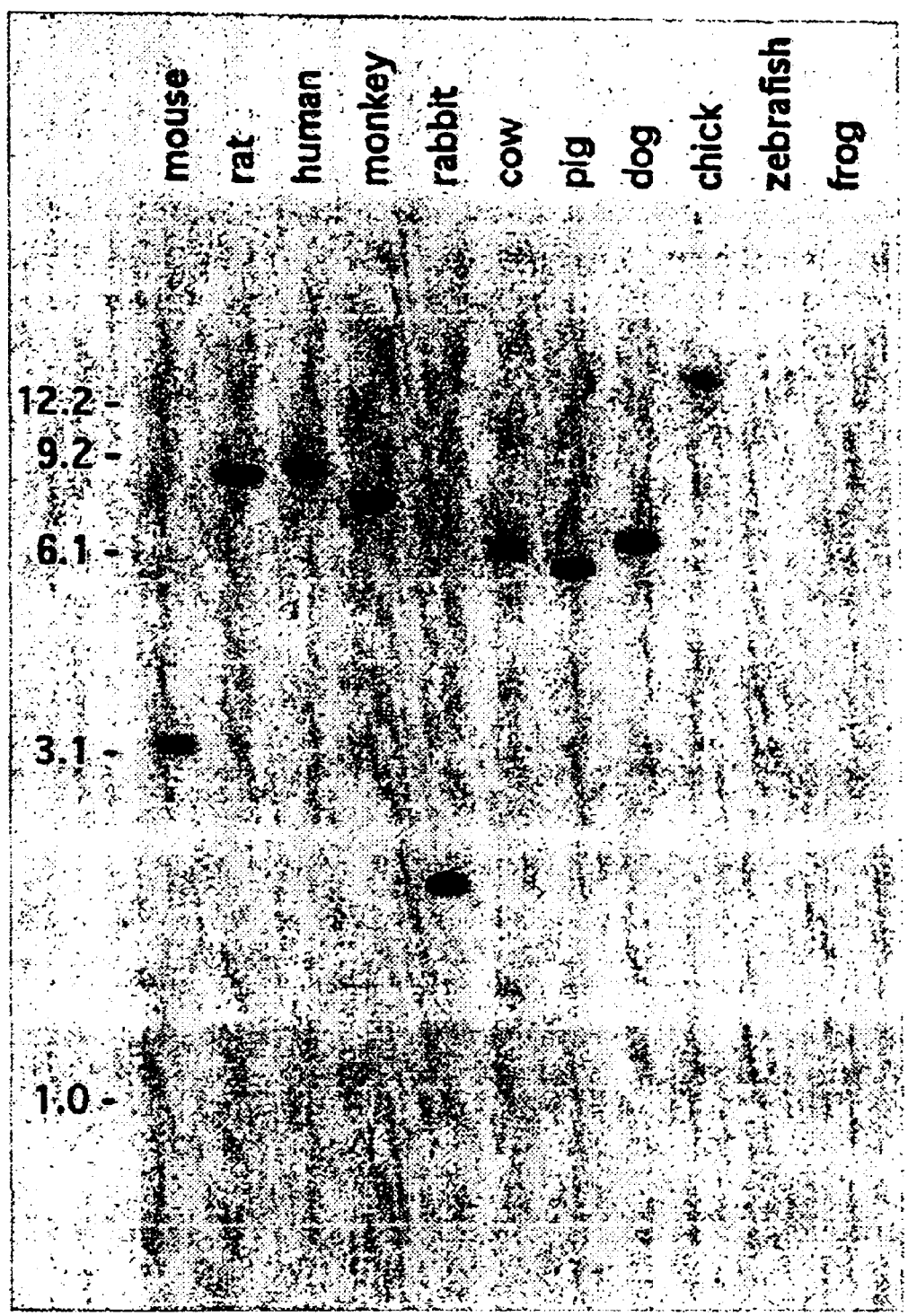
Figure 4B:
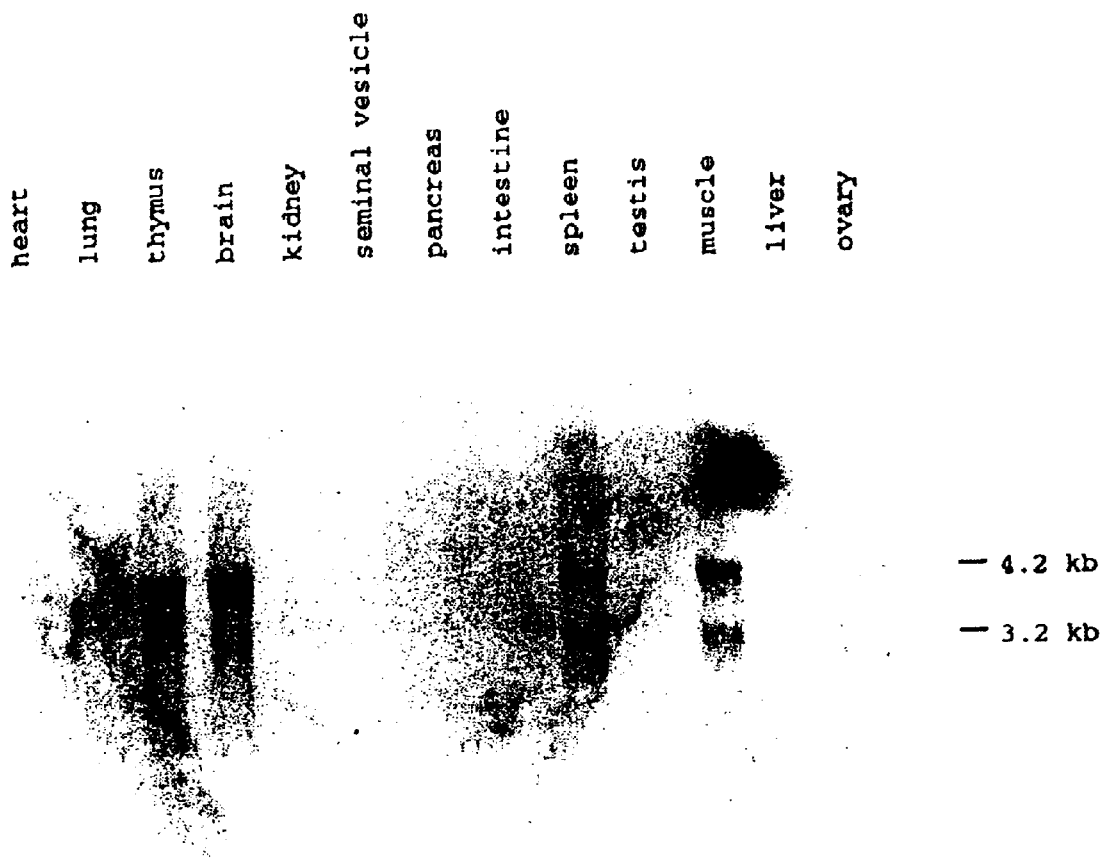

The invention provides an isolated polynucleotide sequence encoding the receptors of the invention. The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences which encode GDF receptors. It is understood that all polynucleotides encoding all or a portion of GDF receptors are also included herein, as long as they encode a polypeptide with GDF receptors activity (e.g., bind to GDF). Such polynucleotides include naturally occurring, synthetic, and intentionally manipulated polynucleotides. For example, portions of the mRNA sequence may be altered due to alternate RNA splicing patterns or the use of alternate promoters for RNA transcription. As another example, GDF receptor polynucleotide may be subjected to site-directed mutagenesis. The polynucleotide sequence for GDF receptors also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of GDF receptors polypeptide encoded by the nucleotide sequence is functionally unchanged. Also included are nucleotide sequences which encode GDF receptors polypeptide.

The polynucleotide encoding GDF receptors for GDFs such as GDF-8 or 11 (shown in the figures). When the sequence is RNA, the deoxyribonucleotides A, G, C, and T are replaced by ribonucleotides A, G, C, and U, respectively. Also included in the invention are fragments (portions) of the above-described nucleic acid sequences that are at least 15 bases in length, which is sufficient to permit the fragment to selectively hybridize to DNA that encodes the GDF receptor. "Selective hybridization" as used herein refers to hybridization under moderately stringent or highly stringent physiological conditions (See, for example, the techniques described in Maniatis et al., 1989 Molecular Cloning A Laboratory Manual, Cold Spring Harbor Laboratory, N.Y., incorporated herein by reference), which distinguishes related from unrelated nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

Specifically disclosed herein are cDNA sequences for GDF-8. SEQ ID NO:3 represents the cDNA sequence encoding human GDF-8 and SEQ ID NO:1 represents a cDNA encoding murine GDF-8.

DNA sequences of the invention can be obtained by several methods. For example, the DNA can be isolated using hybridization or computer-based techniques which are well known in the art. These include, but are not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences; and 5) differential screening of a subtracted DNA library.

Preferably the GDF receptor polynucleotide of the invention is derived from avian, bovine, ovine, piscine, murine, human or porcine. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981). Alternatively, a subtractive library, as illustrated herein is useful for elimination of non-specific cDNA clones.

When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

A cDNA expression library, such as lambda gt11, can be screened indirectly for GDF receptors peptides having at least one epitope, using antibodies specific for GDF receptors. Such antibodies can be either polyclonally or monoclonally derived and used to detect expression product indicative of the presence of GDF receptors cDNA.

Alterations in GDF receptors nucleic acid include intragenic mutations (e.g., point mutation, nonsense (stop), missense, splice site and frameshift) and heterozygous or homozygous deletions. Detection of such alterations can be done by standard methods known to those of skill in the art including sequence analysis, Southern blot analysis, PCR based analyses (e.g., multiplex PCR, sequence tagged sites (STSs)) and in situ hybridization. Such proteins can be analyzed by standard SDS-PAGE and/or immunoprecipitation analysis and/or Western blot analysis, for example.

DNA sequences encoding GDF receptors can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the GDF receptor polynucleotide sequences may be inserted into a recombinant expression vector. The term "recombinant expression vector" refers to a plasmid, virus or other vehicle known in the art that has been manipulated by insertion or incorporation of the GDF receptors genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene*, 56:125, 1987), the pMSXND expression vector for expression in mammalian cells (Lee and Nathans, *J. Biol. Chem.*, 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding GDF receptors can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention. Methods which are well known to those skilled in the art can be used to construct expression vectors containing the GDF receptors coding sequence and appropriate transcriptional/translational control signals. These methods include in vitro recombinant DNA techniques, synthetic techniques, and in vivo recombination/genetic techniques. (See, for example, the techniques described in Maniatis et al., 1989 Molecular Cloning A Laboratory Manual, Cold Spring Harbor Laboratory, N.Y.)

A variety of host-expression vector systems may be utilized to express the GDF receptors coding sequence. These include but are not limited to microorganisms such as bacteria transformed with recombinant bacteriophage DNA, plasmid DNA or cosmid DNA expression vectors containing the GDF receptors coding sequence; yeast transformed with recombinant yeast expression vectors containing the GDF receptors coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the GDF receptors coding sequence; insect cell systems infected with recombinant virus expression vectors (e.g., baculovirus) containing the GDF receptors coding sequence; or animal cell systems infected with recombinant virus expression vectors (e.g., retroviruses, adenovirus, vaccinia virus) containing the GDF receptors coding sequence, or transformed animal cell systems engineered for stable expression. Since GDF receptors has not been confirmed to contain carbohydrates, both bacterial expression systems as well as those that provide for translational and post-translational modifications may be used; e.g., mammalian, insect, yeast or plant expression systems.

Depending on the host/vector system utilized, any of a number of suitable transcription and translation elements, including constitutive and inducible promoters, transcription enhancer elements, transcription terminators, etc. may be used in the expression vector (see e.g., Bitter et al., 1987, Methods in Enzymology 153:516–544). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted GDF receptors coding sequence.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 31987, Acad. Press, N.Y., Vol. 153, pp.516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, 1986, IRL Press, Wash., D.C.). Alternatively, vectors may be used which promote integration of foreign DNA sequences into the yeast chromosome.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and advantageously, plasma membrane insertion of the gene product may be used as host cells for the expression of GDF receptors.

Mammalian cell systems which utilize recombinant viruses or viral elements to direct expression may be engineered. For example, when using adenovirus expression vectors, the GDF receptors coding sequence may be ligated to an adenovirus transcription/-translation control complex, e.g., the late promoter and tripartite leader sequence. Alternatively, the vaccinia virus 7.5K promoter may be used. (e.g., see, Mackett et al., 1982, Proc. Natl. Acad. Sci. USA 79: 7415–7419; Mackett et al., 1984, J. Virol. 49: 857–864; Panicali et al., 1982, Proc. Natl. Acad. Sci. USA 79: 4927–4931). Of particular interest are vectors based on bovine papilloma virus which have the ability to replicate as extrachromosomal elements (Sarver, et al., 1981, Mol. Cell. Biol. 1: 486). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the GDF receptors gene in host cells (Cone & Mulligan, 1984, Proc. Natl. Acad. Sci. USA 81:6349–6353). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the GDF receptors cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., 1977, Cell 11: 223), hypoxanthine-guanine phosphoribosyltransferase (Szybalska & Szybalski, 1962, Proc. Natl. Acad. Sci. USA 48: 2026), and adenine phosphoribosyltransferase (Lowy, et al., 1980, Cell 22: 817) genes can be employed in tk-, hgprt$^-$ or aprt$^-$ cells respectively. Also, antimetabolite resistance can be used as the basis of selection for dhfr, which confers resistance to methotrexate (Wigler, et al., 1980, Natl. Acad. Sci. USA 77: 3567; O'Hare, et al., 1981, Proc. Natl. Acad. Sci. USA 78: 1527); gpt, which confers resistance to mycophenolic acid (Mulligan & Berg, 1981, Proc. Natl. Acad Sci. USA 78: 2072; neo, which confers resistance to the aminoglycoside G-418 (Colberre-Garapin, et al., 1981, J. Mol. Biol. 150: 1); and hygro, which confers resistance to hygromycin (Santerre, et al., 1984, Gene 30: 147) genes. Recently, additional selectable genes have been described, namely trpB, which allows cells to utilize indole in place of tryptophan; hisD, which allows cells to utilize histinol inplace of histidine (Hartman & Mulligan, 1988, Proc. Natl. Acad. Sci. USA 85: 8047); and ODC (ornithine decarboxylase) which confers resistance to the omithine decarboxylase inhibitor, 2-(difluoromethyl)-DL-omithine, DFMO (McConlogue L., 1987, In: Current Communications in Molecular Biology, Cold Spring Harbor Laboratory ed.).

When the host is a eukaryote, such methods of transfection of DNA as calcium phosphate co-precipitates, conventional mechanical procedures such as microinjection, electro-poration, insertion of a plasmid encased in liposomes, or virus vectors may be used. Eukaryotic cells can also be cotransformed with DNA sequences encoding the GDF receptors of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, Eukaryotic Viral Vectors, Cold Spring Harbor Laboratory, Gluzman ed., 1982).

CELL LINES

In one embodiment, the present invention relates to stable recombinant cell lines, the cells of which express GDF receptor polypeptides and contain DNA that encodes GDF receptors. Suitable cell types include but are not limited to cells of the following types: NIH 3T3 (Murine), C2C12, L6, and P19. C2C12 and L6 myoblasts will differentiate spontaneously in culture and form myotubes depending on the particular growth conditions (Yaffe and Saxel, 1977; Yaffe, 1968). P19 is an embryonal carcinoma cell line. Such cells are described, for example, in the Cell Line Catalog of the American Type Culture Collection (ATCC). These cells can be stably transformed by a method known to the skilled artisan. See, for example, Ausubel et al., Introduction of DNA Into Mammalian Cells, in CURRENT PROTOCOLS IN MOLECULAR BIOLOGY, sections 9.5.1–9.5.6 (John Wiley & Sons, Inc. 1995). "Stable" transformation in the context of the invention means that the cells are immortal to the extent of having gone through at least 50 divisions.

GDF receptors can be expressed using inducible or constituitive regulatory elements for such expression. Commonly used constituitive or inducible promoters, for example, are known in the art. The desired protein encoding sequence and an operably linked promoter may be introduced into a recipient cell either as a non-replicating DNA (or RNA) molecule, which may either be a linear molecule or, more preferably, a closed covalent circular molecule. Since such molecules are incapable of autonomous replication, the expression of the desired molecule may occur through the transient expression of the introduced sequence. Alternatively, permanent expression may occur through the integration of the introduced sequence into the host chromosome. Therefore the cells can be transformed stably or transiently.

An example of a vector that may be employed is one which is capable of integrating the desired gene sequences into the host cell chromosome. Cells which have stably integrated the introduced DNA into their chromosomes can be selected by also introducing one or more markers which allow for selection of host cells which contain the expression vector.

The marker may complement an auxotrophy in the host (such as leu2, or ura3, which are common yeast auxotrophic markers), biocide resistance, e.g., antibiotics, or heavy metals, such as copper, or the like. The selectable marker gene can either be directly linked to the DNA gene sequences to be expressed, or introduced into the same cell by co-transfection.

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors include vaccinia virus expression vectors. A third class of vectors relies upon the integration of the desired gene sequences into the host chromosome. Cells which have stably integrated the introduced DNA into their chromosomes may be selected by also introducing one or more markers (e.g., an exogenous gene) which allow selection of host cells which contain the expression vector. The marker may provide for prototropy to an auxotrophic host, biocide resistance, e.g., antibiotics, or heavy metals, such as copper or the like. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, H., Mol. Cell. Biol., 3:280 (1983), and others.

Once the vector or DNA sequence containing the construct has been prepared for expression, the DNA construct may be introduced (transformed) into an appropriate host. Various techniques may be employed, such as protoplast fusion, calcium phosphate precipitation, electroporation or other conventional techniques.

TRANSGENIC ANIMALS

In another embodiment, the present invention relates to transgenic animals having cells that express GDF receptors. Such transgenic animals, for example those containing the GDF-8 receptor, may have decreased fat content and increased muscle mass. The subject invention provides non-human transgenic animals which are useful as a source of food products with high muscle and protein content, and reduced fat and cholesterol content. The animals have been altered chromosomally in their germ cells and somatic cells so that the production of GDF-8 may be at "normal" levels, however, the GDF-8 receptor is produced in reduced amounts, or is completely disrupted, resulting in animals with decreased binding of GDF-8 and higher than normal levels of muscle tissue, preferably without increased fat and/or cholesterol levels. Accordingly, the present invention also includes food products provided by the animals. Such food products have increased nutritional value because of the increase in muscle tissue. The transgenic non-human animals of the invention include bovine, porcine, ovine and avian animals, for example.

The subject invention also provides a method of producing animal food products having increased muscle content. The method includes modifying the genetic makeup of the germ cells of a pronuclear embryo of the animal, implanting the embryo into the oviduct of a pseudopregnant female thereby allowing the embryo to mature to full term progeny, testing the progeny for presence of the transgene to identify transgene-positive progeny, cross-breeding transgene-positive progeny to obtain further transgene-positive progeny and processing the progeny to obtain foodstuff. The modification of the germ cell comprises altering the genetic composition so as to disrupt or reduce the expression of the naturally occurring gene encoding for production of GDF-8 receptor protein. In a particular embodiment, the transgene comprises antisense polynucleotide sequences to the GDF-8 receptor protein. Alternatively, the transgene may comprise a non-functional sequence which replaces or intervenes in the native GDF-8 receptor gene or the transgene may encode a GDF-8 receptor antagonist.

The subject invention also provides a method of producing avian food products having improved muscle content. The method includes modifying the genetic makeup of the germ cells of a pronuclear embryo of the avian animal, implanting the embryo into the oviduct of a pseudopregnant female into an embryo of a chicken, culturing the embryo under conditions whereby progeny are hatched, testing the progeny for presence of the genetic alteration to identify transgene-positive progeny, cross-breeding transgene-positive progeny and processing the progeny to obtain foodstuff.

The term "animal" here denotes all mammalian species except human. It also includes an individual animal in all stages of development, including embryonic and fetal stages. Farm animals (pigs, goats, sheep, cows, horses, rabbits and the like), rodents (such as mice), and domestic pets (for example, cats and dogs) are included within the scope of the present invention.

A "transgenic" animal is any animal containing cells that bear genetic information received, directly or indirectly, by deliberate genetic manipulation at the subcellular level, such as by microinjection or infection with recombinant virus. "Transgenic" in the present context does not encompass classical crossbreeding or in vitro fertilization, but rather denotes animals in which one or more cells receive a recombinant DNA molecule. Although it is highly preferred that this molecule be integrated within the animal's chromosomes, the present invention also contemplates the use of extrachromosomally replicating DNA sequences, such as might be engineered into yeast artificial chromosomes.

The term "transgenic animal" also includes a "germ cell line" transgenic animal. A germ cell line transgenic animal is a transgenic animal in which the genetic information has been taken up and incorporated into a germ line cell, therefore conferring the ability to transfer the information to offspring. If such offspring in fact possess some or all of that information, then they, too, are transgenic animals.

The cDNA that encodes GDF receptors can be fused in proper reading frame under the transcriptional and translational control of a vector to produce a genetic construct that is then amplified, for example, by preparation in a bacterial vector, according to conventional methods. See, for example, the standard work: Sambrook et al., MOLECULAR CLONING: A LABORATORY MANUAL (Cold Spring Harbor Press 1989), the contents of which are incorporated by reference. The amplified construct is thereafter excised from the vector and purified for use in producing transgenic animals.

The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

The transgene to be used in the practice of the subject invention may be a DNA sequence comprising a modified GDF receptors coding sequence. In a preferred embodiment, the GDF receptor gene is disrupted by homologous targeting in embryonic stem cells. For example, the entire mature C-terminal region of the GDF receptors gene may be deleted as described in the examples below. Optionally, the GDF receptors disruption or deletion may be accompanied by insertion of or replacement with other DNA sequences, such as a non-functional GDF receptors sequence. In other embodiments, the transgene comprises DNA antisense to the coding sequence for GDF receptors. In another embodiment, the transgene comprises DNA encoding an antibody or receptor peptide sequence which is able to bind to GDF receptors. Where appropriate, DNA sequences that encode proteins having GDF receptors activity but differ in nucleic acid sequence due to the degeneracy of the genetic code may also be used herein, as may truncated forms, allelic variants and interspecies homologues.

ANTIBODIES WHICH BIND TO GDF RECEPTORS

In another embodiment, the present invention relates to antibodies that bind GDF receptors that block GDF binding to the receptor. For example, such antibodies may be useful for ameliorating disorders associated with muscle tissue.

A monoclonal antibody which binds to GDF-8 receptor may have the effect of increasing the development of skeletal muscles. In preferred embodiments of the claimed methods, the GDF-8 receptor monoclonal antibody, polypeptide, or polynucleotide is administered to a patient suffering from a disorder selected from the group consisting of muscle wasting disease, neuromuscular disorder, muscle atrophy or aging. The GDF-8 receptor antibody may also be administered to a patient suffering from a disorder selected from the group consisting of muscular dystrophy, spinal cord injury, traumatic injury, congestive obstructive pulmonary disease (COPD), AIDS or cachechia. In a preferred embodiment, the GDF-8 antibody is administered to a patient with muscle wasting disease or disorder by intravenous, intramuscular or subcutaneous injection; preferably, a monoclonal antibody is administered within a dose range between about 0.1 mg/kg to about 100 mg/kg; more preferably between about 1 ug/kg to 75 mg/kg; most preferably from about 10 mg/kg to 50 mg/kg. The antibody may be administered, for example, by bolus injunction or by slow infusion. Slow infusion over a period of 30 minutes to 2 hours is preferred. The GDF-8 antibody may be formulated in a formulation suitable for administration to a patient. Such formulations are known in the art. The dosage regimen will be determined by the attending physician considering various factors which modify the action of the GDF-8 receptor protein, e.g. amount of tissue desired to be formed, the site of tissue damage, the condition of the damaged tissue, the size of a wound, type of damaged tissue, the patient's age, sex, and diet, the severity of any infection, time of administration and other clinical factors. The dosage may vary with the type of matrix used in the reconstitution and the types of agent, such as anti-GDF-8 receptor antibodies, to be used in the composition. Generally, systemic or injectable administration, such as intravenous (IV), intramuscular (IM) or subcutaneous (Sub-Q) injection. Administration will generally be initiated at a dose which is minimally effective, and the dose will be increased over a preselected time course until a positive effect is observed. Subsequently, incremental increases in dosage will be made limiting such incremental increases to such levels that produce a corresponding increase in effect, while taking into account any adverse affects that may appear. The addition of other known growth factors, such as IGF I (insulin like growth factor I), human, bovine, or chicken growth hormone which may aid in increasing muscle mass, to the final composition, may also affect the dosage. In the embodiment where an anti-GDF-8 receptor antibody is administered, the anti-GDF-8 antibody is generally administered within a dose range of about 0.1 ug/kg to about 100 mg/kg.; more preferably between about 10 mg/kg to 50 mg/kg.

The preparation of polyclonal antibodies is well-known to those skilled in the art. See, for example, Green et al., PROTOCOLS (Manson, ed.), pages 1–5 (Humana Press 1992); Coligan et al., *Production of Polyclonal Antisera in Rabbits, Rats, Mice and Hamsters*, in CURRENT PROTOCOLS IN IMMUNOLOGY, section 2.4.1 (1992), which are hereby incorporated by reference.

The preparation of monoclonal antibodies likewise is conventional. See, for example, Kohler & Milstein, *Nature* 256:495 (1975); Coligan et al., sections 2.5.1–2.6.7; and Harlow et al., ANTIBODIES: A LABORATORY MANUAL, page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., *Purification of Immunoglobulin G (IgG)*, in METHODS IN MOLECULAR BIOLOGY, VOL. 10, pages 79–104 (Humana Press 1992). Methods of in vitro and in vivo multiplication of monoclonal antibodies is well-known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., osyngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present invention. For example, antibodies of the present invention may also be derived from subhuman primate antibody. General techniques for raising therapeutically useful antibodies in baboons can be found, for example, in Goldenberg et al., International Patent Publication WO 91/11465 (1991) and Losman et al., *Int. J Cancer* 46:310 (1990), which are hereby incorporated by reference.

Alternatively, a therapeutically useful anti-GDF receptors antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad Sci. USA* 86:3833 (1989), which is hereby incorporated in its entirety by reference. Techniques for producing humanized monoclonal antibodies are described, for example, by Jones et al., *Nature* 321: 522 (1986); Riechmann et al., *Nature* 332: 323 (1988); Verhoeyen et al., *Science* 239: 1534 (1988); Carter et al., *Proc. Nat'l Acad Sci. USA* 89: 4285 (1992); Sandhu, *Crit. Rev. Biotech.* 12: 437 (1992); and Singer et al., *J. Immunol.* 150: 2844 (1993), which are hereby incorporated by reference.

Antibodies of the invention also may be derived from human antibody fragments isolated from a combinatorial immunoglobulin library. See, for example, Barbas et al., METHODS: A COMPANION TO METHODS IN ENZYMOLOGY, VOL. 2, page 119 (1991); Winter et al., *Ann. Rev. Immunol.* 12: 433 (1994), which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994); Lonberg et al., *Nature* 368:856 (1994); and Taylor et al., *Int. Immunol.* 6:579 (1994), which are hereby incorporated by reference.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. No. 4,036,945 and U.S. Pat. No. 4,331,647, and references contained therein. These patents are hereby incorporated in their entireties by reference. See also Nisonhoff et al., Arch. Biochem. Biophys. 89:230 (1960); Porter, *Biochem. J.* 73:119 (1959); Edelman et al., METHODS IN ENZYMOLOGY, VOL. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., *Proc. Nat'l Acad. Sci. USA* 69:2659 (1972). Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., METHODS: A COMPANION TO METHODS IN ENZYMOLOGY, VOL. 2, page 97 (1991); Bird et al., *Science* 242:423–426 (1988); Ladner el al., U.S. Pat. No. 4,946,778; Pack et al., *Bio/Technology* 11: 1271–77 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., METHODS: A COMPANION TO METHODS IN ENZYMOLOGY, VOL. 2, page 106 (1991).

IDENTIFICATION OF GDF RECEPTORS

In another embodiment, the invention provides a method for identifying a GDF receptor polypeptide comprising incubating components comprising GDF polypeptide and a cell expressing a receptor or a soluble receptor under conditions sufficient to allow the GDF to bind to the receptor; measuring the binding of the GDF polypeptide to the receptor; and isolating the receptor. The GDF may be any of the known GDFs (e.g., GDF-1–16), and preferably is GDF-8 or GDF-11. Methods of isolating the receptors are described in more detail in the Examples section below.

VARIANTS OF GDF RECEPTORS

The term "GDF receptors variant" as used herein means a molecule that simulates at least part of the structure of GDF receptors. GDF receptor variants may also be useful in preventing GDF binding, thereby ameliorating symptoms of disorders described above.

In one embodiment, the present invention relates to peptides and peptide derivatives that have fewer amino acid residues than GDF receptors. Such peptides and peptide derivatives could represent research and diagnostic tools in the study of muscle wasting diseases and the development of more effective therapeutics.

The invention relates not only to peptides and peptide derivatives of naturally-occurring GDF receptors, but also to GDF receptor mutants and chemically synthesized derivatives of GDF receptors that bind GDFs. For example, changes in the amino acid sequence of GDF receptors are contemplated in the present invention. GDF receptors can be altered by changing the DNA encoding the protein. Preferably, only conservative amino acid alterations are undertaken, using amino acids that have the same or similar properties. Illustrative amino acid substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine.

Variants useful for the present invention comprise analogs, homologs, muteins and mimetics of GDF receptors that retain the ability to bind to their respective GDFs. Peptides of the GDF receptors refer to portions of the amino acid sequence of GDF receptors that also retain this ability. The variants can be generated directly from GDF receptors itself by chemical modification, by proteolytic enzyme digestion, or by combinations thereof. Additionally, genetic engineering techniques, as well as methods of synthesizing polypeptides directly from amino acid residues, can be employed.

Peptides of the invention can be synthesized by such commonly used methods as t-BOC or FMOC protection of alpha-amino groups. Both methods involve stepwise syntheses whereby a single amino acid is added at each step starting from the C terminus of the peptide (See, Coligan, et al., *Current Protocols in Immunology*, Wiley Interscience, 1991, Unit 9). Peptides of the invention can also be synthesized by the well known solid phase peptide synthesis methods described Merrifield, *J. Am. Chem. Soc.*, 85:2149, 1962), and Stewart and Young, Solid Phase Peptides Synthesis, (Freeman, San Francisco, 1969, pp.27–62), using a copoly(styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman egradation.

Alternatively, peptides can be produced by recombinant methods as described below.

The term "substantially purified" as used herein refers to a molecule, such as a peptide that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. One skilled in the art can purify GDF receptors peptides using standard protein purification methods and the purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

Non-peptide compounds that mimic the binding and function of GDF receptors ("mimetics") can be produced by the approach outlined in Saragovi et al., *Science* 253: 792–95 (1991). Mimetics are molecules which mimic elements of protein secondary structure. See, for example, Johnson et al., "Peptide Turn Mimetics," in BIOTECHNOLOGY AND PHARMACY, Pezzuto et al., Eds., (Chapman and Hall, New York 1993). The underlying rationale behind the use of peptide mimetics is that the peptide backbone of proteins exists chiefly to orient amino acid side chains in such a way as to facilitate molecular interactions. For the purposes of the present invention, appropriate mimetics can be considered to be the equivalent of GDF receptors itself.

Longer peptides can be produced by the "native chemical" ligation technique which links together peptides (Dawson, et al., *Science*, 266:776, 1994). Variants can be created by recombinant techniques employing genomic or cDNA cloning methods. Site-specific and region-directed mutagenesis techniques can be employed. See CURRENT PROTOCOLS IN MOLECULAR BIOLOGY vol. 1, ch. 8 (Ausubel et al. eds., J. Wiley & Sons 1989 & Supp. 1990–93); PROTEIN ENGINEERING (Oxender & Fox eds., A. Liss, Inc. 1987). In addition, linker-scanning and PCR-mediated techniques can be employed for mutagenesis. See PCR TECHNOLOGY (Erlich ed., Stockton Press 1989); CURRENT PROTOCOLS IN MOLECULAR BIOLOGY, vols. 1 & 2, supra. Protein sequencing, structure and modeling approaches for use with any of the above techniques are disclosed in PROTEIN ENGINEERING, loc. cit., and CURRENT PROTOCOLS IN MOLECULAR BIOLOGY, vols. 1 & 2, supra.

GDF RECEPTOR-BINDING AND BLOCKING AGENTS

In yet another embodiment, the present invention relates to GDF receptor-binding agents that block binding of GDFs to their receptors. Such agents could represent research and diagnostic tools in the study of muscle wasting disorder as described above and the development of more effective therapeutics. In addition, pharmaceutical compositions comprising GDF receptor-binding agents may represent effective therapeutics. In the context of the invention, the phrase "GDF receptor-binding agent" denotes a naturally occurring ligand of GDF receptors such as, for example: GDF-1–16; a synthetic ligand of GDF receptors, or appropriate derivatives of the natural or synthetic ligands. The determination and isolation of ligands is well described in the art. See, e.g., Lemer, *Trends NeuroSci.* 17:142–146 (1994) which is hereby incorporated in its entirety by reference.

In yet another embodiment, the present invention relates to GDF receptor-binding agents that interfere with binding between GDF receptor and a GDF. Such binding agents may interfere by competitive inhibition, by non-competitive inhibition or by uncompetitive inhibition. Interference with normal binding between GDF receptors and one or more GDF can result in a useful pharmacological effect.

SCREEN FOR BINDING AND BLOCKING COMPOSITIONS

In another embodiment, the invention provides a method for identifying a composition which binds to GDF receptors. The method includes incubating components comprising the composition and GDF receptors under conditions sufficient to allow the components to interact and measuring the binding of the composition to GDF receptors. Compositions that bind to GDF receptors include peptides, peptidomimetics, polypeptides, chemical compounds and biologic agents as described above.

Incubating includes conditions which allow contact between the test composition and GDF receptors. Contacting includes in solution and in solid phase. The test ligand (s)/composition may optionally be a combinatorial library for screening a plurality of compositions. Compositions identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988).

To determine if a composition can functionally complex with the receptor protein, induction of the exogenous gene is monitored by monitoring changes in the protein levels of the protein encoded for by the exogenous gene, for example. When a composition(s) is found that can induce transcription of the exogenous gene, it is concluded that this composition(s) can bind to the receptor protein coded for by the nucleic acid encoding the initial sample test composition (s).

Expression of the exogenous gene can be monitored by a functional assay or assay for a protein product, for example. The exogenous gene is therefore a gene which will provide an assayable/measurable expression product in order to allow detection of expression of the exogenous gene. Such exogenous genes include, but are not limited to, reporter genes such as chloramphenicol acetyltransferase gene, an alkaline phosphatase gene, beta-galactosidase, a luciferase gene, a green fluorescent protein gene, guanine xanthine phosphoribosyltransferase, alkaline phosphatase, and antibiotic resistance genes (e.g., neomycin phosphotransferase).

Expression of the exogenous gene is indicative of composition-receptor binding, thus, the binding or blocking composition can be identified and isolated. The compositions of the present invention can be extracted and purified from the culture media or a cell by using known protein purification techniques commonly employed, such as extraction, precipitation, ion exchange chromatography, affinity chromatography, gel filtration and the like. Compositions can be isolated by affinity chromatography using the modified receptor protein extracellular domain bound to a column matrix or by heparin chromatography.

Also included in the screening method of the invention is combinatorial chemistry methods for identifying chemical compounds that bind to GDF receptors. Thus, the screening method is also useful for identifying variants, binding or blocking agents, etc., which functionally, if not physically (e.g., sterically) act as antagonists or agonists, as desired.

EXAMPLES

Distribution of Receptors for GDF-8 and GDF-11

The purified GDF-8 and GDF-11 proteins will be used primarily to assay for biological activities. In order to identify potential target cells for GDF-8 and GDF-11 action cells expressing their receptors will be searched. For this purpose, the purified protein will be radioiodinated using the chloramine T method, which has been used successfully to label other members of this superfamily, like TFG-β (Cheifetz et al., 1987), activins (Sugino et al., 1988), and BMPs (Paralkar et al., 1991), for receptor-binding studies. The mature processed forms of GDF-8 and GDF-11 each contain multiple tyrosine residues. Two different approaches will then be taken to attempt to identify receptors for these proteins.

One approach will be taken to determine the number, affinity, and distribution of receptors. Either whole cells grown in culture, frozen sections of embryos or adult tissues, or total membrane fractions prepared from tissues or cultured cells will be incubated with the labeled protein, and the amount or distribution of bound protein will be determined. For experiments involving cell lines or membranes, the amount of binding will be determined by measuring either the amount of radioactivity bound to cells on the dish after several washes or, in the case of membranes, the amount of radioactivity sedimented with the membranes after centrifugation or retained with the membranes on a filter. For experiments involving primary cultures, where the number of cells may be more limited, binding sites will be visualized directly by overlaying with photographic emulsion. For experiments involving frozen sections, sites of ligand binding will be visualized by exposing these sections to high resolution Beta-max hyperfilm; if finer localization is required, the sections will be dipped in photographic emulsion. For all of these experiments, specific binding will be determined by adding excess unlabeled protein as competitor (for example, see Lee and Nathans, 1988).

A second approach will also be taken to begin to characterize the receptor biochemically. Membrane preparations or potential target cells grown in culture will be incubated with labeled ligand, and receptor/ligand complexes will be covalently cross-linked using disuccinimidyl suberate, which has been commonly used to identify receptors for a variety of ligands, including members of the TFG-$\beta$ superfamily (for example, see Massague and Like, 1985). Cross-linked complexes will then be electrophoresed on SDS polyacrylamide gels to look for bands labeled in the absence but not in the presence of excess unlabeled protein. The molecular weight of the putative receptor will be estimated by subtracting the molecular weight of the ligand. An important question that these experiments will address is whether GDF-8 and GDF-11 signal through type I and type II receptors like many other members of the TFG-$\beta$ superfamily (for review, see Massague, 1996).

Once a method for detecting receptors for these molecules has been achieved, more detailed analysis will be carried out to determine the binding affinities and specificities. A Scatchard analysis will be used to determine the number of binding sites and dissociation constants. By carrying out cross-competition analyses between GDF-8 and GDF-11 (see FIGS. 1 and 2, respectively for nucleotide and amino acid sequences), it will be possible to determine whether they are capable of binding to the same receptor and their relative affinities. These studies will be critical as they will give an indication as to whether the molecules signal through the same or different receptors. Competition experiments using other TFG-$\beta$ family members will be performed to determine specificity. Some of these ligands are available commercially, and some others are available from Genetics Institute, Inc.

For these experiments, a variety of embryonic and adult tissues and cell lines will be tested. Based on the specific expression of GDF-8 in skeletal muscle and the phenotype of GDF-8 knock-out mice, initial studies focus on embryonic and adult muscle tissue for membrane preparation and for receptor studies using frozen sections. In addition, myoblasts will be isolated and cultured from embryos at various days of gestation or satellite cells from adult muscle as described (Vivarelli and Cossu, 1986; Cossu et al., 1980). The binding studies on these primary cells after various days in culture will be performed and binding sites localized by autoradiography so that the binding sites can be co-localized with various myogenic markers, such as muscle myosin (Vivarelli et al., 1988), and correlate binding with the differentiation state of the cells, such as formation of multinucleated myotubes. In addition to using primary cells, cell lines will be utilized to look for receptors. In particular, the initial focus will be on three cells lines, C2C12, L6, and P19. C2C12 and L6 myoblasts will differentiate spontaneously in culture and form myotubes depending on the particular growth conditions (Yaffe and Saxel, 1977; Yaffe, 1968). P19 embryonal carcinoma cells can be induced to differentiate into various cell types, including skeletal muscle cells in the presence of DMSO (Rudnicki and McBurney, 1987). Receptor binding studies will be carried out on these cell lines under various growth conditions and at various stages of differentiation.

Although the initial studies will focus on muscle cells, other tissues and cell types will be examined for the presence of GDF-8 and GDF-11 receptors.

Figure 5:
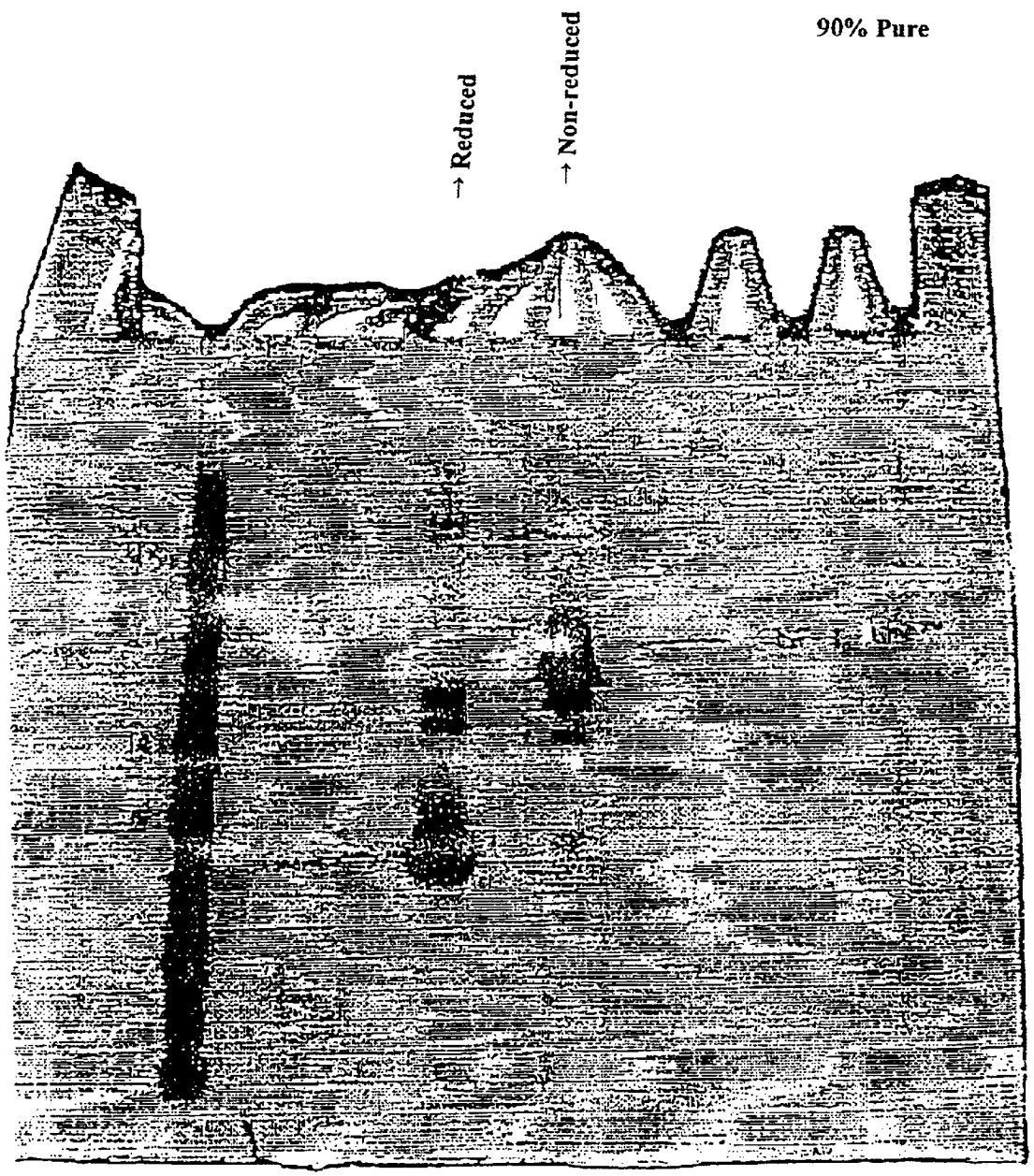
FIG. 5 shows an autoradiogram showing GDF-8.
Figure 6:
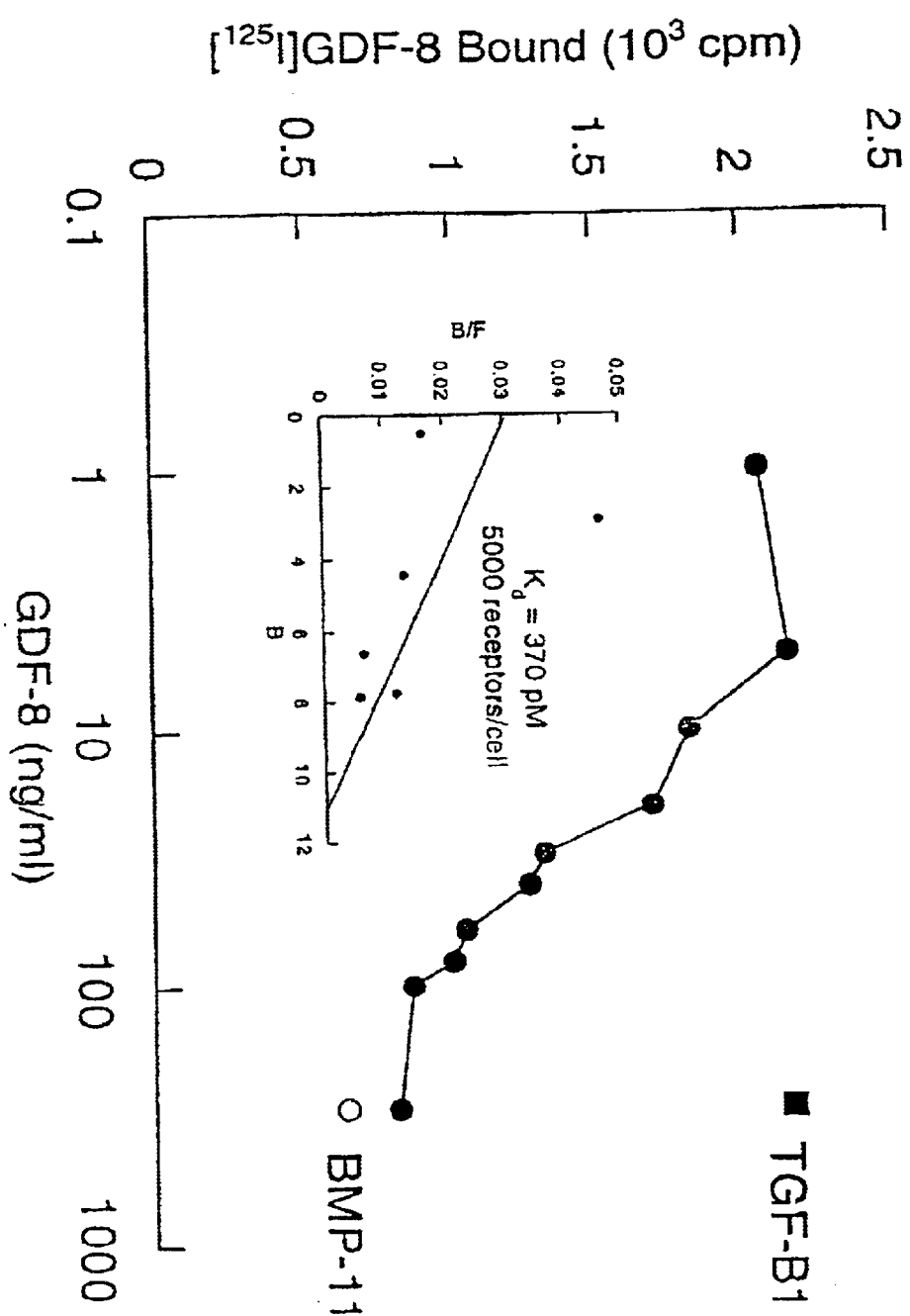
FIGS. 6 and 7 show binding studies for GDF-8.
Figure 7:
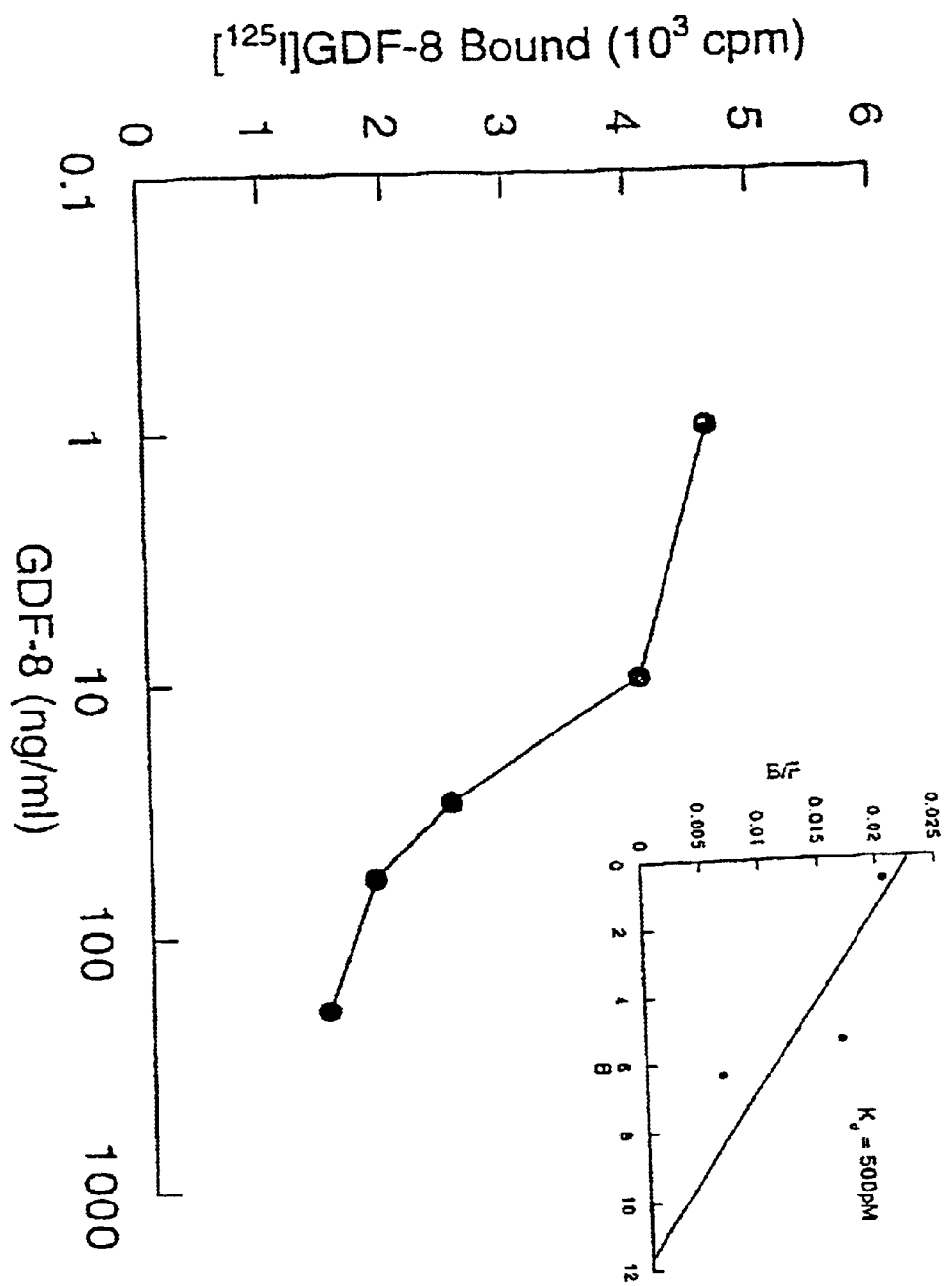
Figure 8:
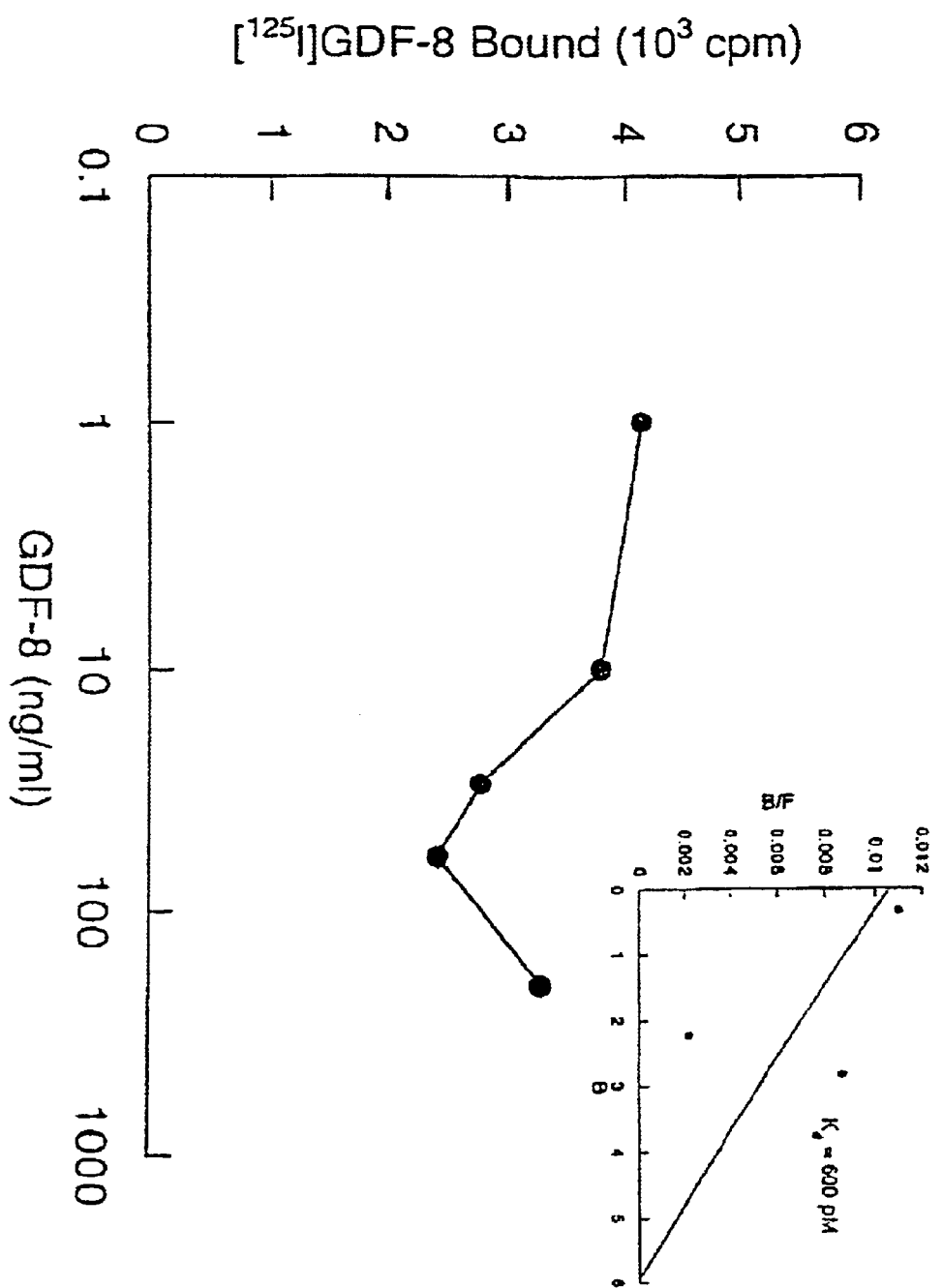
FIGS. 8–11 show 4 myoblast cell lines that do not bind GDF-8.
Figure 9:
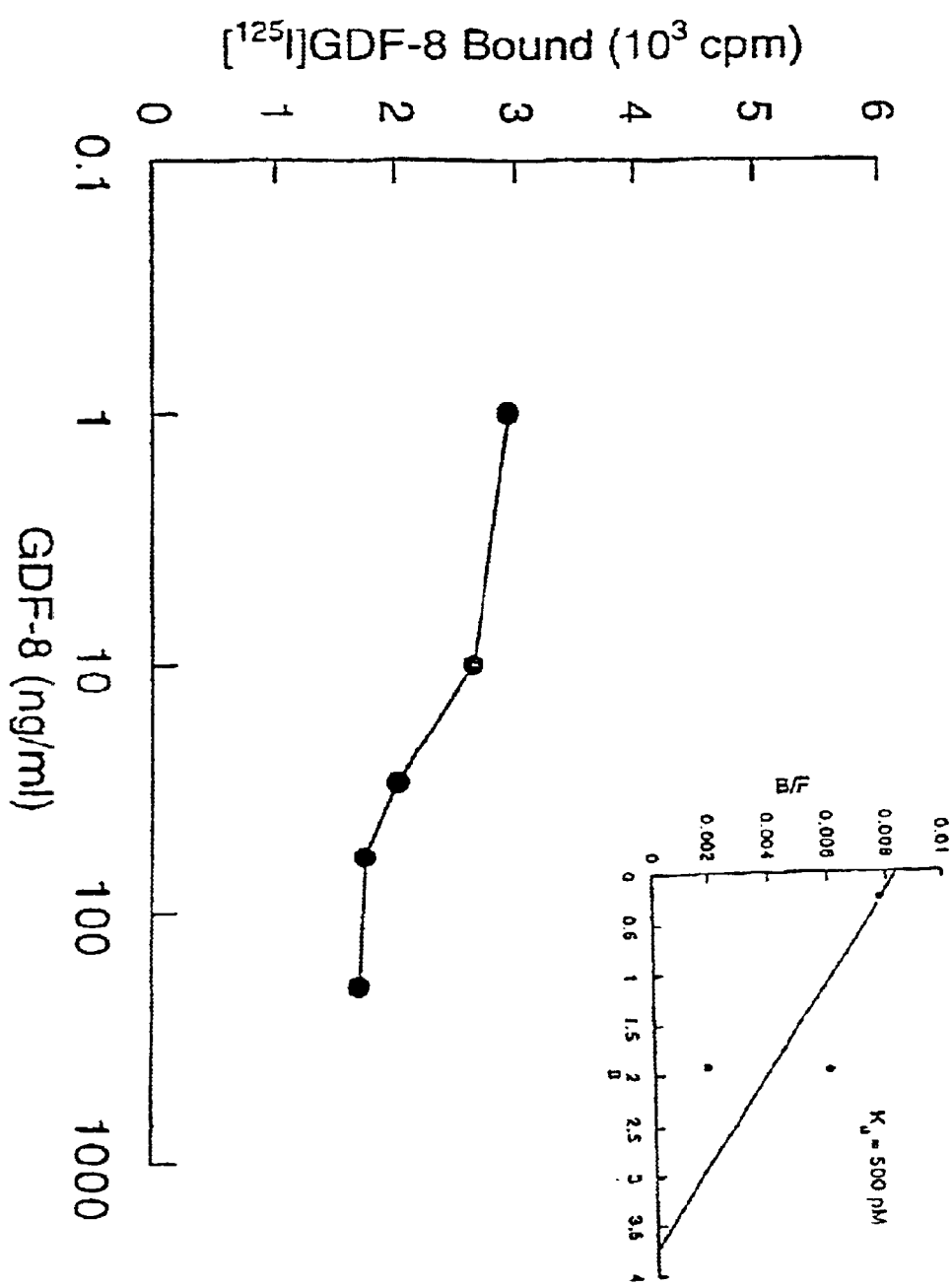
Figure 10:
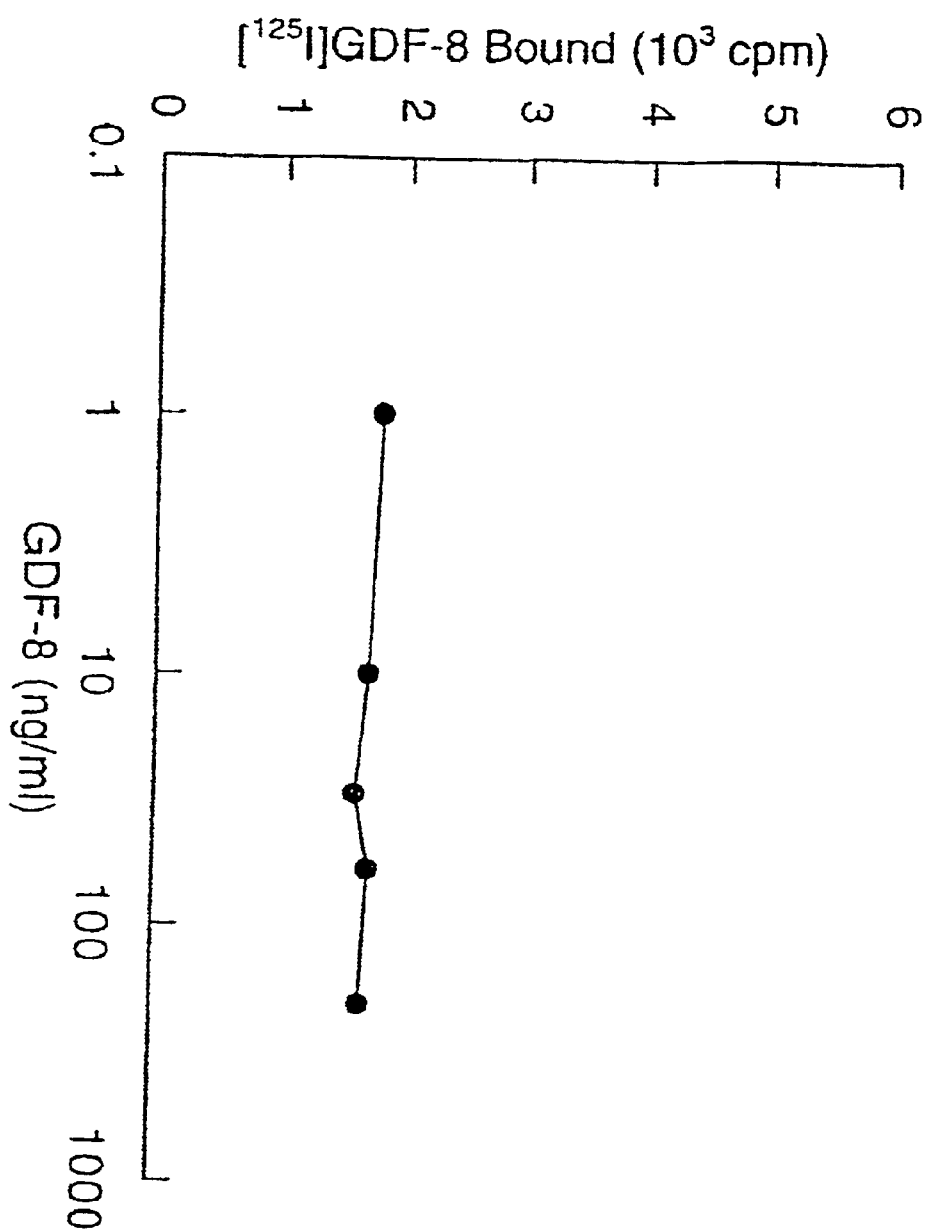
Figure 11:
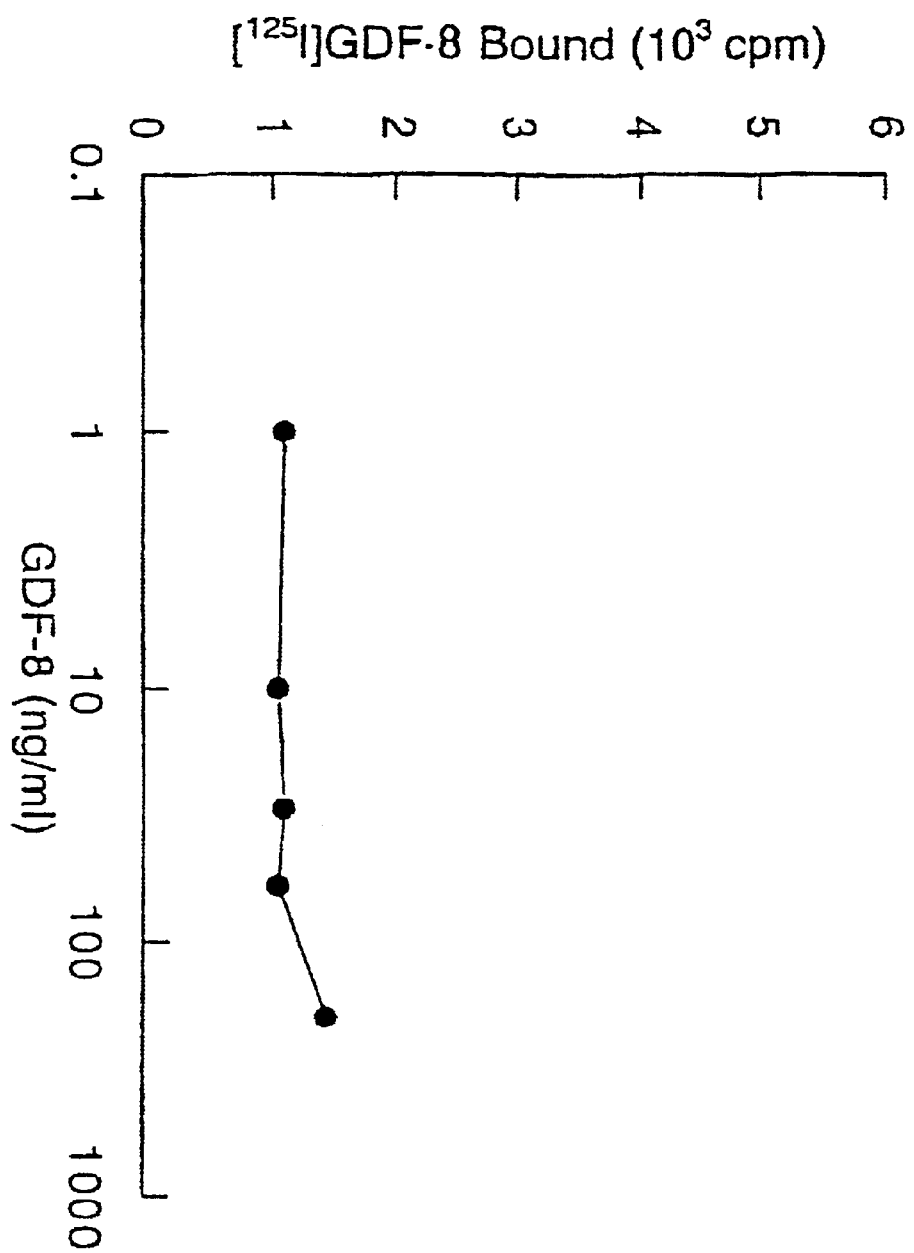

Recombinant human GDF-8 homodimer was used in these binding studies. The rh-GDF-8 was expressed using CHO cells and purified to approximately 90% purity. The autoradiograph (FIG. 5) shows that the GDF-8 has the expected 25–27 KD molecular weight and upon reduction is reduced to the 12 KD monomer. Using I-125 labeled GDF-8 in a receptor-ligand binding assay, two myoblast cell lines, L6 and G-8, were found to bind GDF-8. The binding was specific since non labeled GDF-8 effectively competed the binding of the labeled ligand. These results are illustrated in FIGS. 6 and 7, respectively. The dissociation constant ($K_d$) is 370 pM and L6 myoblasts have a high number (5,000 receptors/cell) of cell surface binding proteins (FIG. 6). GD-11 (also called BMP-11) is highly homologous (>90%) to GDF-8. Receptor binding studies were performed to determine if GDF-11 also binds the GDF-8 receptor. FIG. 6 shows that GDF-8 and GDF-11 do bind to the same binding proteins on L6 myoblasts. It is important to establish whether or not GDF-8 binds to the known TGF-$\beta$ receptor. As shown in FIG. 6, TGF-$\beta$ does not compete the binding of GDF-8, indicating that the GDF-8 receptor is distinct from the TGF-$\beta$ receptor. The GDF-8 receptor is not expressed on all myoblast cell lines. FIGS. 8–11 are examples of four myoblast cell lines (C2C12, G7, MLB13MYC c14 and BC3H1) which do not bind GDF-8.

Cloning the Gene or Genes Encoding Receptors for GDF-8 and GDF-11.

As a first step towards understanding the mechanism by which GDF-8 and GDF-11 exert their biological effects, it is important to clone the genes encoding their receptors. From the experiments above, it will be more clear as to whether GDF-8 and GDF-11 bind to the same receptor or to different receptors. There will also be considerable information regarding the tissue and cell type distribution of these receptors. Using this information, two different approaches will be taken to clone the receptor genes.

The first approach will be to use an expression cloning strategy. In fact, this was the strategy that was orginally used by Mathews and Vale (1991) and Lin et al. (1992) to clone the first activin and TFG-$\beta$ receptors. We will begin by preparing poly A-selected RNA from the tissue or cell type that expresses the highest relative number of high affinity binding sites. We will then use this RNA to prepare a cDNA library in the mammalian expression vector pcDNA-1. This vector contains a CMV promoter and an SV40 origin of replication. The library will be plated, and cells from each plate will be pooled into broth and frozen. Aliquots from each pool will then be grown for preparation of DNA. Each individual pool will be transiently transfected into COS cells in chamber slides, and transfected cells will be incubated with iodinated GDF-8 or GDF-11. After washing away the unbound protein, the sites of ligand binding will be visualized by autoradiography. Once a positive pool is identified, the cells from that pool will be replated at lower density, and the process will be repeated. Positive pools will then be plated, and individual colonies will be picked into grids and re-analyzed as described (Wong et al., 1985).

We will attempt to carry out this screen initially using pool sizes of 1500 colonies. In order to be certain that we will be able to identify a positive clone in a mixture of this complexity, we will carry out a control experiment using TFG-β and a cloned type II receptor. The coding sequence for the TFG-β type 11 receptor will be cloned into the pcDNA-1 vector, and bacteria transformed with this construct will be mixed with bacteria from our library at various ratios, including 1:1500. We will then transfect DNA prepared from this mixture into COS cells, incubate with iodinated TGF-β, and visualize by autoradiography. If we can see positive signals at a ratio of 1:1500, we will begin screening pools of 1500 clones. Otherwise, we will use smaller pool sizes corresponding to ratios at which the procedure is sensitive enough to identify a positive signal in our control experiments. While we have no previous experience in expression cloning per se, we have constructed over 50 cDNA libraries in the past, and many of these have yielded a high frequency of full-length cDNA clones.

We will also use a second parallel strategy to attempt to clone the GDF-8 and GDF-11 receptors. We will take advantage of the fact that most receptors for members of the TFG-β superfamily that have been identified belong to the membrane-spanning serine/threonine kinase family (for review, see Massague, 1996). Because the cytoplasmic domains of these receptors are related in sequence, we will attempt to use degenerate PCR to clone members of this receptor family that are expressed in tissues that contain binding sites for GDF-8 and GDF-11. In fact, this is the approach that has been used to identify most of the members of this receptor family. We have extensive experience using this type of strategy for identifying ligands in this superfamily, and therefore, we are quite confident that we will be able to carry out this approach successfully. The general strategy will be to design degenerate primers corresponding to conserved regions of the known receptors, to use these primers for PCR on cDNA prepared from the appropriate RNA samples (most likely from skeletal muscle), to subclone the PCR products, and finally to sequence individual subclones. As sequences are identified, they will be used as hybridization probes to eliminate duplicate clones from further analysis. We will then test the receptors that we identify for their ability to bind purified GDF-8 and GDF-11. Because this screen will yield only small PCR products, we will obtain full-length cDNA clones for each receptor from cDNA libraries prepared from the appropriate tissue, insert these cDNA clones into the pcDNA-11 vector, transfect these constructs into COS cells, and assay the transfected cells for their ability to bind iodinated GDF-8 or GDF-11. Ideally, we would like to test every receptor that we identify in this screen for their ability to bind these ligands. However, the number of receptors that we identify may be large, and isolating all of the full-length cDNAs and testing them may require considerable effort. Almost certainly some of the receptors that we identify will correspond to known receptors, and for these, either obtaining full-length cDNA clones from other investigators or amplifying the coding seqences by PCR based on the published sequences should be straightforward. For novel sequences, we will determine their tissue distribution by Northern analysis and then give the highest priority to those receptors whose expression pattern most closely resembles the distribution of GDF-8 and/or GDF-11 binding sites as determined above.

In particular, it is known that these receptors fall into two classes, type I and type II, which can be distinguished based on the sequence and which are both required for full activity. Certain ligands cannot bind type I receptors in the absence of type II receptors while others are capable of binding both receptor types (for review, see Massague, 1996). The cross-linking experiments outlined above should give some indication as to whether both type I and type II receptors are also involved in signalling GDF-8 and GDF-11. If so, it will be important to clone both of these receptor subtypes in order to fully understand how GDF-8 and GDF-11 transmit their signals. Because we cannot predict whether the type I receptor is capable of interacting with GDF-8 and GDF-11 in the absence of the type II receptor, we will focus first on cloning the type II receptor(s). Only after we have at least one type II receptor for these ligands in hand will we attempt to identify the type I receptors for GDF-8 and GDF-11. Our general strategy will be to co-transfect the type II receptor with each of the type 1 receptors that we identify in the PCR screen and then assay the transfected cells by crosslinking as described in Specific Aim 4. If the type I receptor is part of the receptor complex for GDF-8 or GDF-11, we should be able to detect two cross-linked receptor species in the transfected cells, one corresponding to the type I receptor and the other corresponding to the type II receptor.

The search for GDF-8 and GDF-11 receptors is further complicated by the fact at least one member of the TFG-β superfamily, namely, GDNF, is capable of signalling through a completely different type of receptor complex involving a GPI-linked component (GDNFR-alpha) and a receptor tyrosine kinase (c-ret) (Trupp et al., 1996; Durbec et al., 1996; Treanor et al., 1996; Jing et al., 1996). Although GDNF is the most distantly-related member of the TFG-β superfamily, it is certainly possible that other TGF-β family members may also signal through an analogous receptor system. If GDF-8 and GDF-11 do signal through a similar receptor complex, our expression screening approach should be able to identify at least the GPI-linked component (indeed GDNFR-alpha was identified using an expression screening approach) of this complex. However, identifying the analogous receptor tyrosine kinase would probably require a substantial amount of additional work, such as biochemical purification of the complex. In the case of GDNF, the similar phenotypes of GDNF- and c-ret-deficient mice suggested c-ret as a potential receptor for GDNF.

GD-11 Transgenic Knockout Mice

Figure 12A:
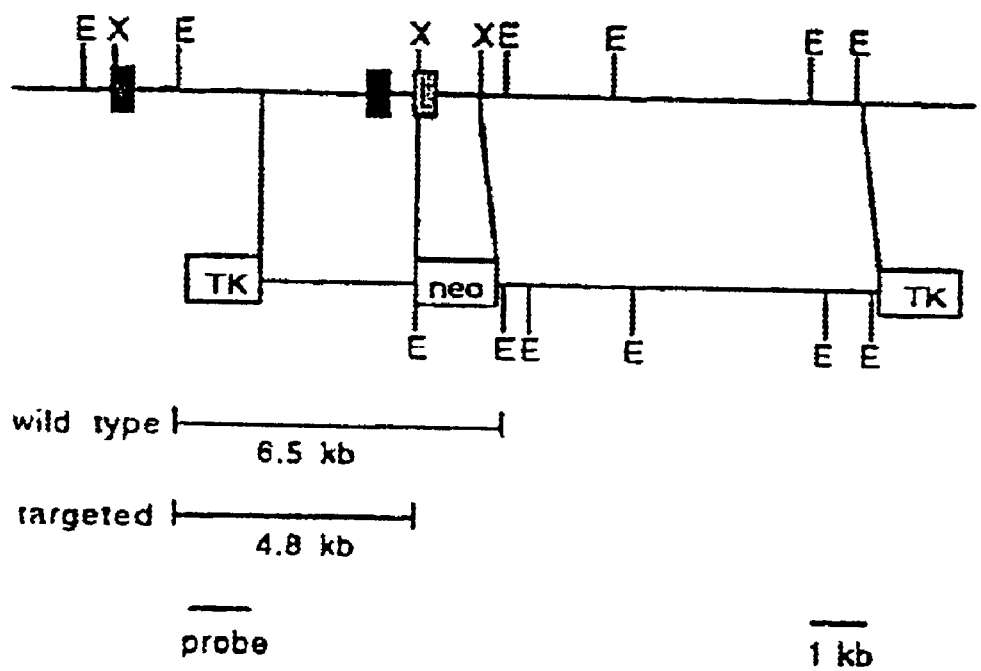
FIG. 12 shows the construction of GDF-11 null mice by homologous targeting. a) is a map of the GDF-11 locus (top line) and targeting construct (second line). The black and stippled boxes represent coding sequences for the pro-and C-terminal regions, respectively. The targeting construct contains a total of 11 kb of homology with the GDF-11 gene. A probe derived from the region upstream of the 3' homology fragment and downstream of the first EcoRI site shown hybridizes to a 6.5 kb EcoRI fragment in the GDF-11 gene and a 4.8 kb fragment in a homologously targeted gene. Abbreviations: X, XbaI; E, EcoRI. b) Geneomic Southern of DNA prepared from F1 heterozygous mutant mice (lanes 1 and 2) and offspring derived from a mating of these mice (lanes 3–12).
Figure 12B:
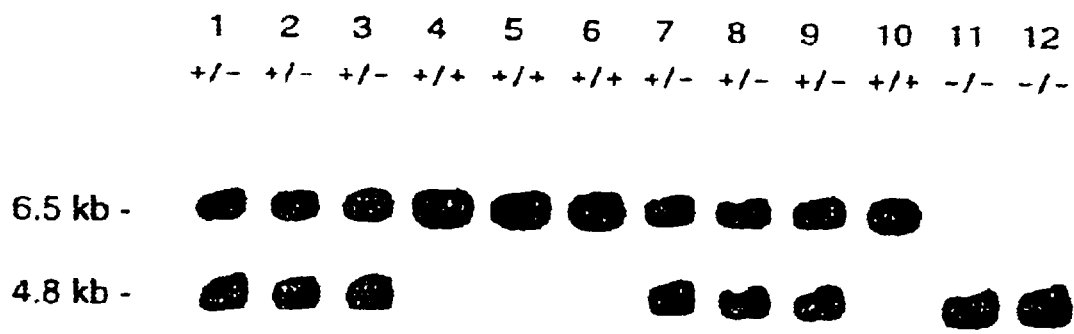

The phenotype of GDF-11 knockout mice in several respects resembles the phenotype of mice carrying a deletion of a receptor for some members of the TGF-β superfamily, the activin type IB receptor (ActRIIB). To determine the biological function of GDF-11, we disrupted the GDF-11 gene by homologous targeting in embryonic stem cells. A murine 129 SV/J genomic library was prepared in lambda FIXII according to the instructions provided by Stratagene (La Jolla, Calif.). The structure of the GDF-11 gene was deduced from restriction mapping and partial sequencing of phage clones isolated from the library. Vectors for preparing the targeting construct were kindly provided by Philip Soriano and Kirk Thomas. To ensure that the resulting mice would be null for GDF-11 function, the entire mature C-terminal region was deleted and replaced by a neo cassette (FIG. 12a,b). R1 ES cells were transfected with the targeting construct, selected with gancyclovir (2 $\mu$M) and G418 (250 $\mu$g/ml), and analyzed by Southern analysis. Homologous targeting of the GDF-11 gene was seen in 8/155 g-ancyclovir/G418 doubly resistant ES cell clones. Following injection of several targeted clones into C57BL/6J blastocysts, we obtained chimeras from one ES clone that produced heterozygous pups when crossed to both C57BL/6J and 129/SvJ females. Crosses of C57BL/6J/129/SvJ hybrid F1 heterozygotes produced 49 wild-type (34%), 94 heterozygous (66%) and no homozygous mutant adult offspring. Similarly, there were no adult homozygous null animals seen in the 129/SvJ background (32 wild-type (36%) and 56 heterozygous mutant (64%) animals).

To deternine the age at which homozygous mutants were dying, we genotyped litters of embryos isolated at various gestational ages from heterozygous females that had been mated to heterozygous males. At all embryonic stages examined, homozygous mutant embryos were present at approximately the predicted frequency of 25%. Among hybrid newborn mice, the different genotypes were also represented at the expected Mendelian ratio of 1:2:1 (34+/+ (28%), 61+/−(50%), and 28−/−(23%)). Homozygous mutant mice were born alive and were able to breath and nurse. All homozygous mutants died, however, within the first 24 hours after birth. The precise cause of death was unknown, but the lethality may have been related to the fact that the kidneys in homozygous mutants were either severely hypoplastic or completely absent. A summary of the kidney abnormalities in these mice is shown in FIG. 13.

Anatomical Differences in Knockout Mice

Figure 14A:
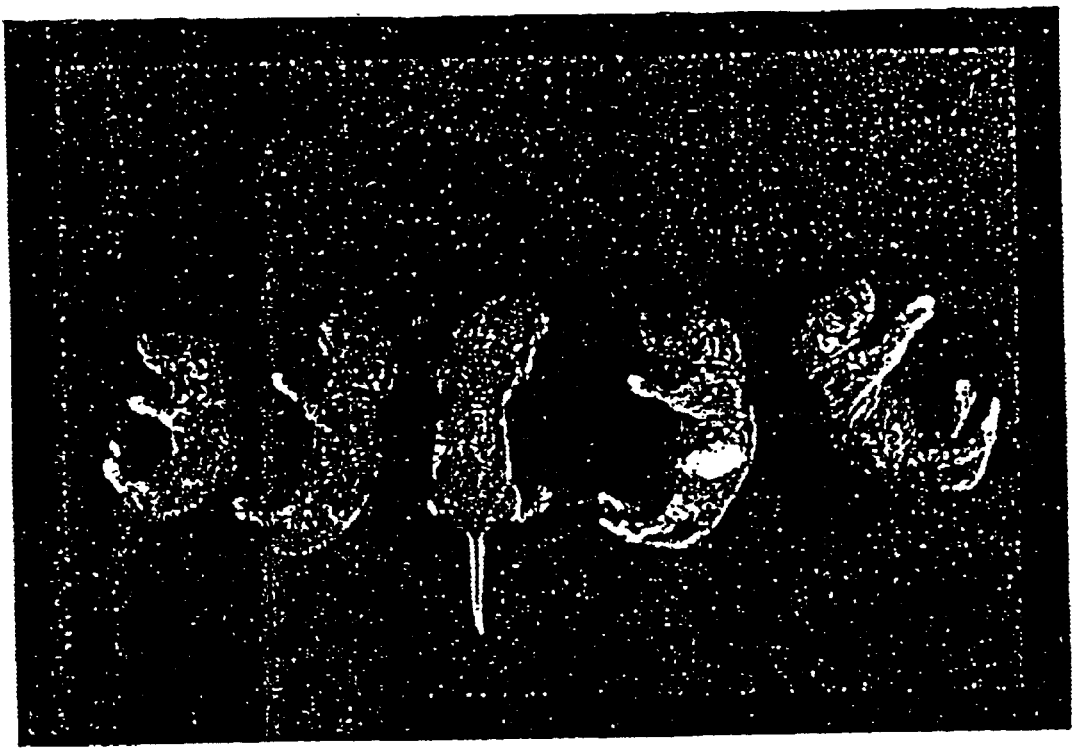
FIG. 14 shows homeotic transformations in GDF-11 mutant mice. a) Newborn pups with missing (first and second from left) and normal looking tails. b–j) Skeleton preparations for newborn wild-type (b, e, h), heterozygous (c, f, I) and homozygous (d, g, j) mutant mice. Whole skeleton preparations (b–d), vertebral columns (e–g), vertebrosternal ribs (h–j) showing transformations and defects in homozygous and heterozygous mutant mice. Numbers indicate thoracic segments.
Figure 14B:
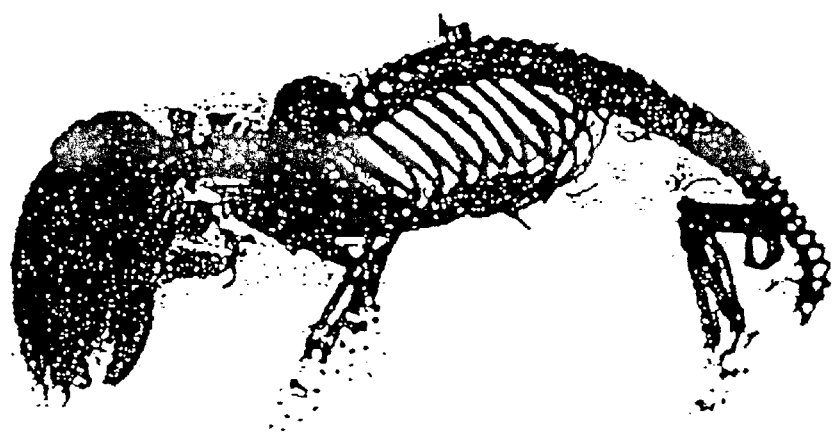
Figure 14C:
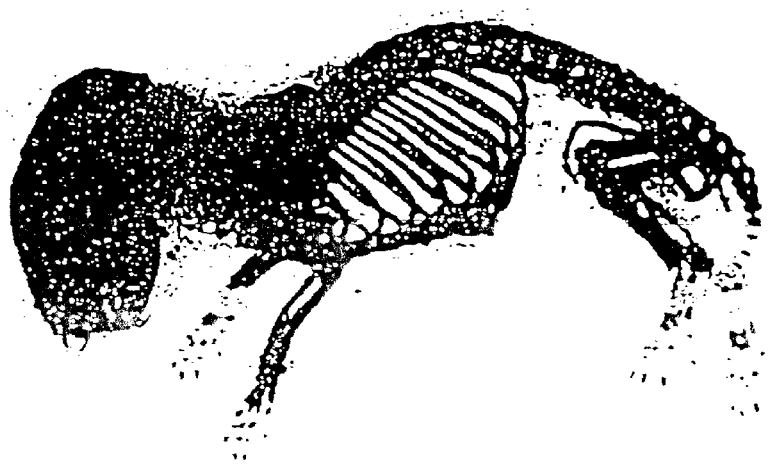
Figure 14D:
Figure 14E:
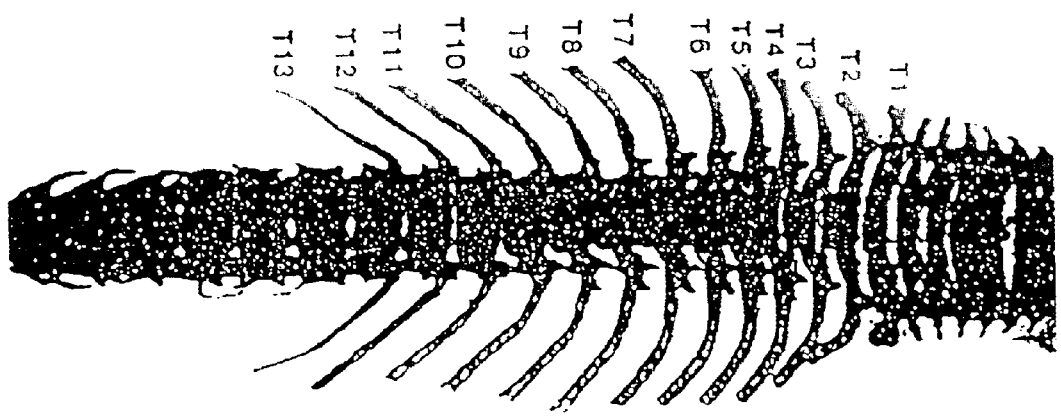
Figure 14F:
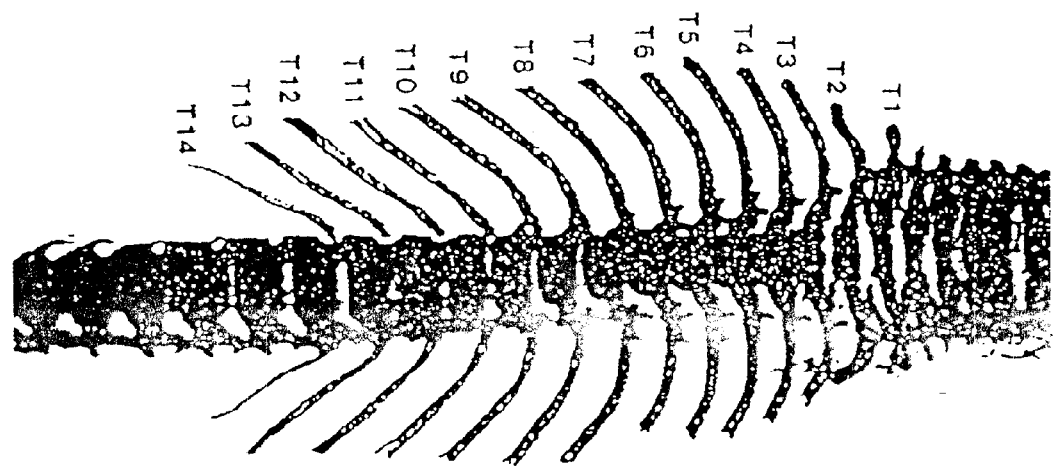
Figure 14G:
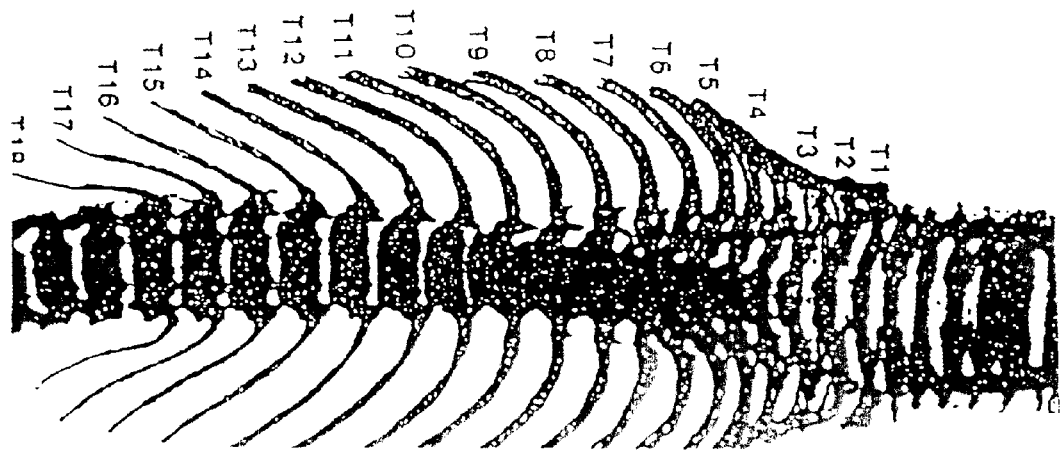
Figure 14H:
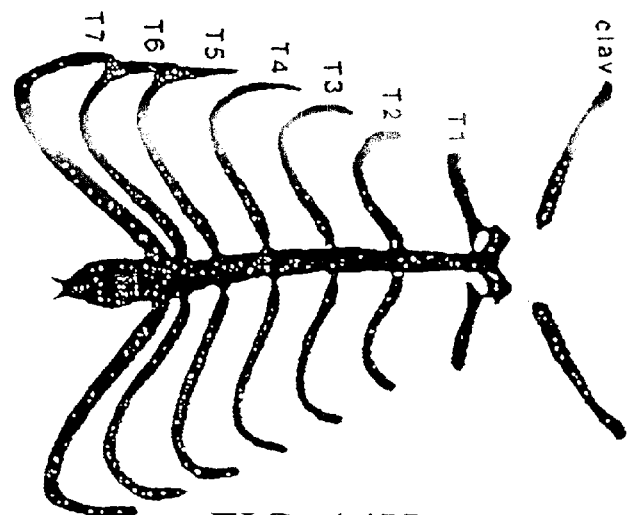
Figure 14I:
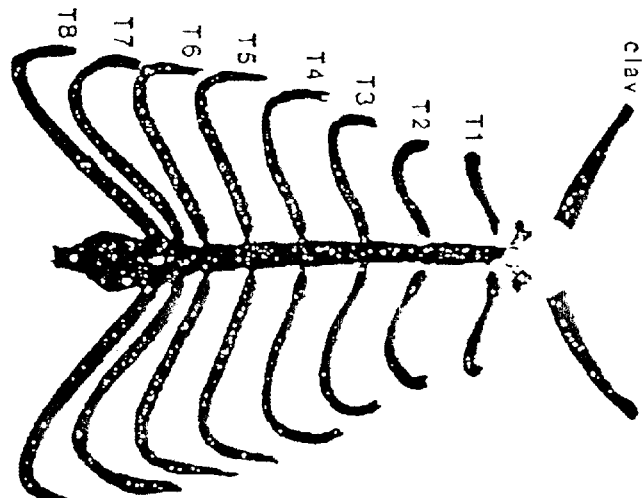
Figure 14J:
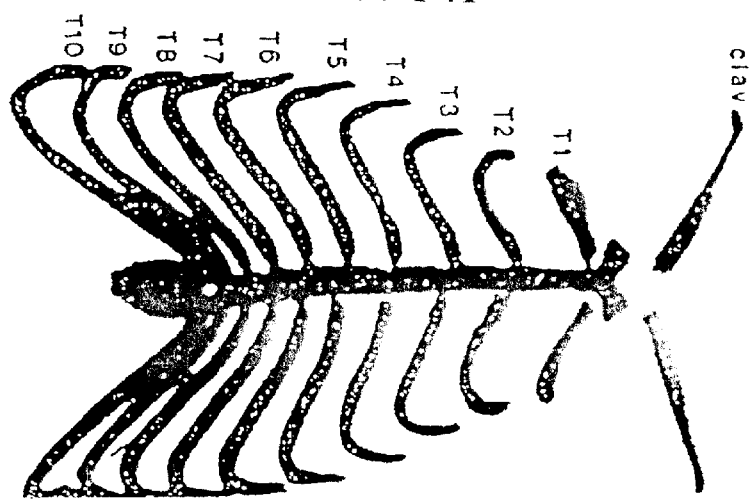

Homozygous mutant animals were easily recognizable by their severely shortened or absent tails (FIG. 14a). To further characterize the tail defects in these homozygous mutant animals, we examined their skeletons to determine the degree of disruption of the caudal vertebrae. A comparison of wild-type and mutant skeleton preparations of late stage embryos and newborn mice, however, revealed differences not only in the caudal region of the animals but in many other regions as well. In nearly every case where differences were noted, the abnormalities appeared to represent homeotic transformations of vertebral segments in which particular segments appeared to have a morphology typical of more anterior segments. These transformations, which are summarized in FIG. 15, were evident throughout the axial skeleton extending from the cervical region to the caudal region. Except for the defects seen in the axial skeleton, the rest of the skeleton, such as the cranium and limb bones, appeared normal.

Anterior transformations of the vertebrae in mutant newborn animals were most readily apparent in the thoracic region, where there was a dramatic increase in the number of thoracic (T) segments. All wild-type mice examined showed the typical pattern of 13 thoracic vertebrae each with its associated pair of ribs (FIG. 14(b,e)). In contrast, homozygous mutant mice showed a striking increase in the number of thoracic vertebrae. All homozygous mutants examined had 4 to 5 extra pairs of ribs for a total of 17 to 18 (FIG. 14(d,g)) although in over ⅓ of these animals, the 18th rib appeared to be rudimentary. Hence, segments that would normally correspond to lumbar (L) segments L1 to L4 or L5 appeared to have been transformed into thoracic segments in mutant animals.

Moreover, transformations within the thoracic region in which one thoracic vertebra had a morphology characteristic of another thoracic vertebra were also evident. For example, in wild-type mice, the first 7 pairs of ribs attach to the sternum, and the remaining 6 are unattached or free (FIG. 14(e,h)). In homozygous mutants, there was an increase in the number of both attached and free pairs of ribs to 10–11 and 7–8, respectively (FIG. 14(g,j)). Therefore, thoracic segments T8, T9, T10, and in some cases even T11, which all have free ribs in wild-type animals, were transformed in mutant animals to have a characteristic typical of more anterior thoracic segments, namely, the presence of ribs attached to the sternum. Consistent with this finding, the transitional spinous process and transitional articular processes which are normally found on T10 in wild-type animals were instead found on T13 in homozygous mutants (data not shown). Additional transformations within the thoracic region were also noted in certain mutant animals. For example, in wild-type mice, the ribs derived from T1 normally touch the top of the sternum. However, in ⅔₂₃ hybrid and ⅔₃₁129/SvJ homozygous mutant mice examined, T2 appeared to have been transformed to have a morphology resembling that of T1; that is, in these animals, the ribs derived from T2 extended to touch the top of the sternum. In these cases, the ribs derived from TI appeared to fuse to the second pair of ribs. Finally, in 82% of homozygous mutants, the long spinous process normally present on T2 was shifted to the position of T3. In certain other homozygous mutants, asymmetric fusion of a pair of vertebrosternal ribs was seen at other thoracic levels.

The anterior transformations were not restricted to the thoracic region. The anterior most transformation that we observed was at the level of the 6th cervical vertebra (C6). In wild-type mice, C6 is readily identifiable by the presence of two anterior tuberculi on the ventral side. In several homozygous mutant mice, although one of these two anterior tuberculi was present on C6, the other was present at the position of C7 instead. Hence, in these mice, C7 appeared to have been partially transformed to have a morphology resembling that of C6. One other homozygous mutant had 2 anterior tuberculi on C7 but retained one on C6 for a complete C7 to C6 transformation but a partial C6 to C5 transformation.

Transformations of the axial skeleton also extended into the lumbar region. Whereas wild-type animals normally have only 6 lumbar vertebrae, homozygous mutants had 8–9. At least 6 of the lumbar vertebrae in the mutants must have derived from segments that would normally have given rise to sacral and caudal vertebrae as the data described above suggest that 4 to 5 lumbar segments were transformed into thoracic segments. Hence, homozygous mutant mice had a total of 33–34 presacral vertebrae compared to 26 presacral vertebrae normally present in wild-type mice. The most common presacral vertebral patterns were C7/T18/L8 and C7/T18/L9 for mutant mice compared to C7/T13/L6 for wild-type mice. The presence of additional presacral vertebrae in mutant animals was obvious even without detailed examination of the skeletons as the position of the hindlimbs relative to the forelimbs was displaced posteriorly by 7–8 segments. Although the sacral and caudal vertebrae were also affected in homozygous mutant mice, the exact nature of each transformation was not as readily identifiable. In wild-type mice, sacral segments S1 and S2 typically have broad transverse processes compared to S3 and S4. In the mutants, there did not appear to be an identifiable S1 or S2 vertebra. Instead, mutant animals had several vertebrae that appeared to have morphology similar to S3. In addition, the transverse processes of all 4 sacral vertebrae are normally fused to each other although in newborns often only fusions of the first 3 vertebrae are seen. In homozygous mutants, however, the transverse processes of the sacral vertebrae were usually unfused. In the caudalmost region, all mutant animals also had severely malformed vertebrae with extensive fusions of cartilage. Although the severity of the fusions made it difficult to count the total number of vertebrae in the caudal region, we were able to count up to 15 transverse processes in several animals. We were unable to determine whether these represented sacral or caudal vertebrae in the mutants because we could not establish morphologic criteria for distinguishing S4 from caudal vertebrae even in wild-type newborn animals. Regardless of their identities, the total number of vertebrae in this region was significantly reduced from the normal number of approximately 30. Hence, although the mutants had significantly more thoracic and lumber vertebrae than wild-type mice, the total number of segments was reduced in the mutants due to the truncation of the tails.

Heterozygous mice also showed abnormalities in the axial skeleton although the phenotype was much milder than in homozygous mice. The most obvious abnormality in heterozygous mice was the presence of an additional thoracic segment with an associated pair of ribs (FIG. 14(c,f)). This transformation was present in every heterozygous animal examined, and in every case, the additional pair of ribs was attached to the sternum (FIG. 14(i)). Hence, T8, whose associated rib normally does not touch the stemrnum, appeared to have been transformed to a morphology characteristic of a more anterior thoracic vertebra, and L1 appeared to have been transformed to a morphology characteristic of a posterior thoracic vertebra. Other abnormalities indicative of anterior transformations were also seen to varying degrees in heterozygous mice. These included a shift of the long spinous process characteristic of T2 by one segment to T3, a shift of the articular and spinous processes from T10 to T11, a shift of the anterior tuberculus on C6 to C7, and transformation of T2 to T1 where the rib associated with T2 touched the top of the sternum.

In order to understand the basis for the abnormalities in axial patterning seen in GDF-11 mutant mice, we examined mutant embryos isolated at various stages of development and compared them to wild-type embryos. By gross morphological examination, homozygous mutant embryos isolated up to day 9.5 of gestation were not readily distinguishable from corresponding wild-type embryos. In particular, the number of somites present at any given developmental age was identical between mutant and wild-type embryos, suggesting that the rate of somite formation was unaltered in the mutants. By day 10.5–11.5 p.c., mutant embryos could be easily distinguished from wild-type embryos by the posterior displacement of the hindlimb by 7–8 somites. The abnormalities in tail development were also readily apparent at this stage. Taken together, these data suggest that the abnormalities observed in the mutant skeletons represented true transformations of segment identities rather than the insertion of additional segments, for example, by an enhanced rate of somitogenesis.

Alterations in expression of homeobox containing genes are known to cause transformations in Drosophila and in vertebrates. To see if the expression patterns of Hox genes (the vertebrate homeobox containing genes) were altered in GDF-11 null mutants we determined the expression pattern of 3 representative Hox genes, Hoxc-6, Hoxc-8 and Hoxc-11, in day 12.5 p.c. wild-type, heterozygous and homozygous mutant embryos by whole mount in situ hybridization. The expression pattern of Hoxc-6 in wild-type embryos spanned prevertebrae 8–15 which correspond to thoracic segments T1–T8. In homozygous mutants, however, the Hoxc-6 expression pattern was shifted posteriorly and expanded to prevertebrae 9–18 (T2–T11). A similar shift was seen with the Hoxc-8 probe. In wild-type embryos, Hoxc-8 was expressed in prevertebrae 13–18 (T6–T11) but, in homozygous mutant embryos, Hoxc-8 was expressed in prevertebrae 14–22 (T7–T15). Finally, Hoxc-11 expression was also shifted posteriorly in that the anterior boundary of expression changed from prevertebrae 28 tin wild-type embryos to prevertebrae 36 in mutant embryos. (Note that because the position of the hindlimb is also shifted posteriorly in mutant embryos, the Hoxc-11 expression patterns in wild-type and mutant appeared similar relative to the hindlimbs). These data provide further evidence that the skeletal abnormalities seen in mutant animals represent homeotic transformations.

The phenotype of GDF-11 mice suggested that GDF-11 acts early during embryogenesis as a global regulator of axial patterning. To begin to examine the mechanism by which GDF-11 exerts its effects, we determined the expression pattern of GDF-11 in early mouse embryos by whole mount in situ hybridization. At these stages the primary sites of GDF-11 expression correlated precisely with the known sites at which mesodermal cells are generated. Expression of GDF-11 was first detected at day 8.25–8.5 p.c. (8–10 somites) in the primitive streak region, which is the site at which ingressing cells form the mesoderm of the developing embryo. Expression was maintained in the primitive streak at day 8.75, but by day 9.5 p.c., when the tail bud replaces the primitive streak as the source of new mesodermal cells, expression of GDF-11 shifted to the tail bud. Hence at these early stages, GDF-11 appears to be synthesized in the region of the developing embryo where new mesodermal cells arise and presumably acquire their positional identity.

The phenotype of GDF-11 knockout mice in several respects resembles the phenotype of mice carrying a deletion of a receptor for some members of the TGF-β superfamily, the activin type IIB receptor (ActRIIB). As in the case of GDF-11 knockout mice, the ActRIIB knockout mice have extra pairs of ribs and a spectrum of kidney defects ranging from hypoplastic kidneys to complete absence of kidneys. The similarity in the phenotypes of these mice raises the possibility that ActRIIB may be a receptor for GDF-11. However, Act RIIB may not be the sole receptor for GDF-11 because the phenotype of GDF-11 knockout mice is more severe than the phenotype of ActRIIB mice. For example, whereas the GDF-11 knockout animals have 4–5 extra pairs of ribs and show homeotic transformations throughout the axial skeleton, the ActRIIB knockout animals have only 3 extra pairs of ribs and do not show transformations at other axial levels. In addition, the data indicate that the kidney defects in the GDF-11 knockout mice are also more severe than those in ActRIIB knockout mice. The ActRIIB knockout mice show defects in left/right axis formation, such as lung isomerism and a range of heart defects that we have not yet observed in GDF-11 knockout mice. ActRIIB can bind the activins and certain BMPs, although none of the knockout mice generated for these ligands show defects in left/right axis formation.

If GDF-11 does act directly on mesodermal cells to establish positional identity, the data presented here would be consistent with either short range or morphogen models for GDF-11 action. That is, GDF-11 may act on mesodermal precursors to establish patterns of Hox gene expression as these cells are being generated at the site of GDF-11 expression, or alternatively, GDF-11 produced at the posterior end of the embryo may diffuse to form a morphogen gradient. Whatever the mechanism of action of GDF-11 may be, the fact that gross anterior/posterior patterning still does occur in GDF-11knockout animals suggests that GDF-11 may not be the sole regulator of anterior/posterior specification. Nevertheless, it is clear that GDF-11 plays an important role as a global regulator of axial patterning and that further study of this molecule will lead to important new insights into how positional identity along the anterior/posterior axis is established in the vertebrate embryo.

Similar phenotypes are expected in GDF-8 knockout animals. For example, GDF-8 knockout animals are expected to have increased number of ribs, kidney defects and anatomical differences when compared to wild-type.

LITERATURE CITED

Baker, J., J. P. Liu, E. J. Robertson and A. Efstratiadis (1993). "Role of insulin-like growth factors in embryonic and postnatal growth." Cell 75: 73–82.

Bladt, F., D. Riethmacher, S. Isenmann, A. Aguzzi and C. Birchmeier (1995). "Essential role for the c-met receptor in the migration of myogenic precursor cells into the limb bud." Nature 376: 768–771.

Bullough, W. S. (1965). "Mitotic and functional homeostasis: A speculative review." Cancer Res 25: 1683–1727.

Cheifetz, S., J. A. Weatherbee, M. L.-S. Tsang, J. K. Anderson, J. E. Mole, R. Lucas and J. Massague (1987). "The transforming growth factor-β system, a complex pattern of cross-reactive ligands and receptors." Cell 48: 409415.

Coleman, M. E., F. DeMayo, K. D. Yin, H. M. Lee, R. Geske, C. Montgomery and R. J. Schwartz (1995). "Myogenic vector expression of insulin-like growth factor I stimulates muscle cell differentiation and myofiber hypertrophy in transgenic mice." J Biol Chem 270: 12109–12116.

Colosi, P., J. J. Swiergiel, E. L. Wilder, A. Oviedo and D. I. H. Linzer (1988). "Characterization of proliferin-related protein." Mol Endocrinol 2: 579–586.

Cossu, G., B. Zani, M. Coletta, M. Bouche, M. Pacifici and M. Molinaro (1980). "In vitro differentiation of satellite cells isolated from normal and dystrophic mammalian muscles. A comparison with embryonic myogenic cells." Cell Differentiation 9: 3-57–368.

Cumming, W. J. K., J. Fulthorpe, P. Hudgson and M. Mahon (1994). Color Atlas of Muscle Pathology, 184–185 (Times Mirror International Publishers Limited, London)

DiMario, J. and R. C. Strohman (1988). "Satellite cells from dystrophic (mdx) mouse muscle are stimulated by fibroblast growth factor in vitro." Differentiation 39: 42–49.

Durbec, P., C. V. Marcos-Gutierrez, C. Kilkenny, M. Grigoriou, K. Wartiowaara, P. Suvanto, D. Smith, B. Ponder, F. Costantini, M. Saarma, H. Sariola and V. Pachnis (1996). "GDNF signalling through the Ret receptor tyrosine kinase." Nature 381: 789–793.

Florini, J. R. (1987). "Hormonal control of muscle growth." Muscle Nerve 10: 577–598.

Florini, J. R., D. Z. Ewton and K. A. Magri (1991). "Hormones, growth factors, and myogenic differentiation." Ann Rev Physiol 53: 201–216.

Friedman, J. M. and R. L. Leibel (1992). "Tackling a weighty problem." Cell 69: 217–220.

Gentry, L. E. and B. W. Nash (1990). "The pro domain of pre-pro-transforming growth factor β1 when independently expressed is a functional binding protein for the mature growth factor." Biochem 29: 6851–6857.

Gentry, L. E., N. R. Webb, G. J. Lim, A. M. Brunner, J. E. Ranchalis, D. R. Twardzik, M. N. Lioubin, H. Marquardt and A. F. Purchio (1987). "Type 1 transforming growth factor beta: Amplified expression and secretion of mature and precursor polypeptides in Chinese hamster ovary cells." Mol Cell Biol 7: 3418–3427.

Hamilton, W. G. and R. G. Ham (1 977). "Clonal growth of Chinese hamster ovary cell lines in protein-free media." In Vitro 13: 537–547.

Jing, S., D. Wen, Y. Yu, P. L. Holst, Y. Luo, M. Fang, R. Tamir, L. Antonio, Z. Hu, R. Cupples, J.-C. Louis, S. Hu, B. W. Altrock and G. M. Fox (1996). "GDNF-induced activation of the Ret protein tyrosine kinase is mediated by GDNF-alpha, a novel receptor for GDNF." Cell 85: 1113–1124.

Lawrence, D. A., R. Pircher and P. Jullien (1985). "Conversion of a high molecular weight latent β-TGF from chicken embryo fibroblasts into a low molecular weight active β-TGF under acidic conditions." Biochem Biophys Res Comm 133: 1026–1034.

Lee, S.-J. and D. Nathans (1988). "Proliferin secreted by cultured cells binds to mannose-6-phosphate receptors." J Biol Chem 263: 3521–3527.

Lin, H. Y., X.-F. Wang, E. Ng-Eaton, R. A. Weinberg and H. F. Lodish (1992). "Expression cloning of the TGF-β type II receptor, a functional transmembrane serine/threonine." Cell 68: 775–785.

Liu, J.-P., J. Baker, A. S. Perkins, E. J. Robertson and A. Efstratiadis (1993). "Mice carrying null mutations of the genes encoding insulin-like growth factor I (Igf-1) and type 1 IGF receptor (Igfl r)." Cell 75:59–72.

Lyons, R. M., J. Keski-Oja and H. L. Moses (1988). "Proteolytic activation of latent transforming growth factor-β from fibroblast-conditioned medium." J Cell Biol 106: 1659–1665.

Massague, J. (1996). "TGFβ signaling: Receptors, transducers, and Mad proteins." Cell 85: 947–950.

Massague, J. and B. Like (1985). "Cellular receptors for type β transforming growth factor." J Biol Chem 260: 2636–2645.

Mathews, L. S., R. E. Hammer, R. R. Behringer, A. J. D'Ercole, G. I. Bell, R. L. Brinster and R. D. Palmiter (1988). "Growth enhancement of transgenic mice expressing human insulin-like growth factor I." Endocrinology 123: 2827–2833.

Mathews, L. S. and W. W. Vale (1991). "Expression cloning of an activin receptor, a predicted transmembrane serine kinase." Cell 65: 973–982.

McPherron, A. C. and S.-J. Lee (1996). The Transforming Growth Factor β Superfamily. Growth Factors and Cytokines in Health and Disease. D. LeRoith and C. Bondy. Greenwich, Conn., JAI Press, Inc. 1B: 357–393.

Miyazono, K., U. Hellman, C. Wernstedt and C.-H. Heldin (1988). "Latent high molecular weight complex of transforming growth factor β1." J Biol Chem 263: 6407–6415.

Paralkar, V. M., R. G. Hammonds and A. H. Reddi (1991). "Identification and characterization of cellular binding proteins (receptors) for recombinant human bone morphogentic protein 2b, an initiator of bone differentiation cascade." Proc Natl Acad Sci, USA 88: 3397–3401.

Powell-Braxton, L., P. Hollingshead, C. Warburton, M. Dowd, S. Pitts-Meek, D. Dalton, N. Gillett and T. A. Stewart (1993). "IFG-I is required for normal embryonic growth in mice." Genes Dev 7: 2609–2617.

Rudnicki, M. A. and M. W. McBumey (1987). Cell culture methods and induction of differentiation of embryonal carcinoma cell lines. Teratocarcinomas and Embryonic Stem Cells: A Practical Approach. E. J. Robertson. Cambridge, United Kingdom, IRL Press: 19–49.

Spiegelman, B. M. and J. S. Flier (1996). "Adipogenesis and obesity: Rounding out the big picture." Cell 87: 377–389.

Sugino, H., T. Nakamura, Y. Hasegawa, K. Miyamoto, M. Igarashi, Y. Eto, H. Shibai and K. Titani (1988). "Identification of a specific receptor for erythroid differentiation factor on follicular granulosa cell." J Biol Chem 263: 15249–15252.

Treanor, J. J. S., L. Goodman, F. de Sauvage, D. M. Stome, K. T. Poulsen, C. D. Beck, C. Gray, M. P. Armanini, R. A. Pollock, F. Hefti, H. S. Phillips, A. Goddard, M. W. Moore, A. Buj-Bello, A. M. Davies, N. Asai, M. Takahashi, R. Vandlen, C. E. Henderson and A. Rosenthal (1996). "Characterization of a multicomponent receptor for GDNF." Nature 382: 80–83.

Trupp, M., E. Arenas, M. Fainzilber, A.-S. Nilsson, B.-A. Sieber, M. Grigoriou, C. Kilkenny, E. Salazar-Grueso, V. Pachnis, U. Arumae, H. Sariola, M. Saarma and C. F. Ibanez (1996). "Functional receptor for GDNF encoded by the c-ret proto-oncogene." Nature 381: 785–789.

Vivarelli, E., W. E. Brown, R. G. Whalen and G. Cossu (1988). "The expression of slow myosin during mammalian somitogenesis and limb bud differentiation." J Cell Biol 107: 2191–2197.

Vivarelli, E. and G. Cossu (1986). "Neural control of early myogenic differentiation in cultures of mouse somites." Dev Biol 117: 319–325.

Wang, E. A., V. Rosen, J. S. D'Alessandro, M. Bauduy, P. Cordes, T. Harada, D. I. Israel, R. M. Hewick, K. M. Kems, P. LaPan, D. P. Luxenberg, D. McQuaid, I. K. Moutsatsos, J. Nove and J. M. Wozney (1990). "Recombinant human bone morphogenetic protein induces bone formation." Proc Natl Acad Sci, USA 87: 2220–2224.

Wilson, C. A., N. di Clemente, C. Ehrenfels, R. B. Pepinsky, N. Josso, B. Vigier and R. L. Cate (1993). "Mullerian inhibiting substance requires its N-terminal domain for maintenance of biological activity, a novel finding within the transforming growth factor-β superfamily." Mol Endocrinol 7: 247–257.

Wong, G. G., J. S. Witek, P. A. Temple, K. M. Wilkens, A. C. Leary, D. P. Luxenberg, S. S. Jones, E. L. Brown, R. M. Kay, E. C. Orr, C. Shoemaker, D. W. Golde, R. J. Kaufman, R. M. Jewick, E. A. Wang and S. C. Clark (1985). "Human GM-CSF: molecular cloning of the complementary DNA and purification of the natural recombinant proteins." Science 228: 810–815.

Yaffe, D. (1968). "Retention of differentiation potentialities during prolonged cultivation of myogenic cells." Proc Natl Acad Sci USA 61: 477–483.

Yaffe, D. and 0. Saxel (1977). "Serial passaging and differentiation of myogenic cells isolated from dystrophic mouse muscle." Nature 270: 725–727.

What is claimed is:

1. A method for identifying a growth differentiation factor-8 (GDF-8) binding protein, which specifically binds to GDF-8, comprising:
   a) incubating components comprising GDF-8 and a cell or fraction of a cell under conditions sufficient to allow GDF-8 to specifically bind to a GDF-8 binding protein; and
   b) measuring specific binding of GDF-8 to a protein of the cell or fraction of a cell, thereby identifying the GDF-8 binding protein.

2. The method of claim 1, wherein the cell contains a recombinant polynucleotide encoding the GDF-8 binding protein.

3. The method of claim 1, wherein the GDF-8 binding protein is expressed on the surface of the cell.

4. The method of claim 1, wherein GDF-8 further comprises a reporter means.

5. The method of claim 4, wherein the reporter means is selected from the group consisting of a radioisotope, a fluorescent compound, a bioluminescent compound, a chemiluminescent compound, a metal chelator, or an enzyme.

6. The method of claim 1, further comprising isolating the GDF-8 binding protein.

7. A method for identifying a cell expressing a recombinant growth differentiation factor-8 (GDF-8) binding protein, comprising:
   a) incubating GDF-8 with a plurality of cells transfected with an expression library under conditions sufficient to allow GDF-8 to specifically bind to a GDF-8 binding protein, wherein the expression library comprises nucleic acid molecules obtained from cells expressing a GDF-8 binding protein; and
   b) identifying a cell from the plurality of cells that specifically binds to GDF-8 through a GDF-8 binding protein encoded by the expression library, thereby identifying a cell expressing a recombinant GDF-8 binding protein.

8. The method of claim 7, wherein the GDF-8 binding protein encoded by the expression library is expressed on the surface of the isolated cell.

9. The method of claim 7, wherein the expression library comprises nucleic acid molecules obtained from myoblast cells.

10. The method of claim 7, wherein the expression library comprises nucleic acid molecules obtained from cells of a myoblast cell line.

11. The method of claim 10, wherein the myoblast cell line is an L6 cell line or a G8 cell line.

12. The method of claim 7, further comprising isolating the cell expressing the recombinant GDF-8 binding protein.

13. The method of claim 12, further comprising isolating the GDF-8 binding protein from the cell expressing the recombinant GDF-8 binding protein.

14. A method for identifying a growth differentiation factor-11 (GDF-11) binding protein, which specifically binds to GDF-11, comprising:
   a) incubating components comprising GDF-8 and a cell or fraction of a cell under conditions sufficient to allow GDF-11 to specifically bind to a GDF-11 binding protein; and
   b) measuring specific binding of GDF-11 to a protein of the cell or fraction of a cell, thereby identifying the GDF-11 binding protein.

15. The method of claim 14, wherein the cell contains a recombinant polynucleotide encoding the GDF-11 binding protein.

16. The method of claim 14, wherein the GDF-11 binding protein is expressed on the surface of the cell.

17. The method of claim 14, wherein GDF-11 further comprises a reporter means.

18. The method of claim 17, wherein the reporter means is selected from the group consisting of a radioisotope, a fluorescent compound, a bioluminescent compound, a chemiluminescent compound, a metal chelator, or an enzyme.

19. The method of claim 14, further comprising isolating the GDF-11 binding protein.

20. A method for identifying a cell expressing a recombinant growth differentiation factor-11 (GDF-11) binding protein, comprising:
   a) incubating GDF-11 with a plurality of cells transfected with an expression library under conditions sufficient to allow GDF-11 to specifically bind to a GDF-11 binding protein, wherein the expression library comprises nucleic acid molecules obtained from cells expressing a GDF-11 binding protein; and
   b) identifying a cell from the plurality of cells that specifically binds to GDF-11 through a GDF-11 binding protein encoded by the expression library, thereby identifying a cell expressing a recombinant GDF-11 binding protein.

21. The method of claim 20, wherein the GDF-11 binding protein encoded by the expression library is expressed on the surface of the isolated cell.

22. The method of claim 20, wherein the expression library comprises nucleic acid molecules obtained from myoblast cells.

23. The method of claim 22, wherein the expression library comprises nucleic acid molecules obtained from cells of a myoblast cell line.

24. The method of claim 23, wherein the myoblast cell line is an L6 cell line or a G8 cell line.

25. The method of claim 17, further comprising isolating the cell expressing the recombinant GDF-11 binding protein.

26. The method of claim 25, further comprising isolating the GDF-11 binding protein from the cell expressing the recombinant GDF-11 binding protein.

* * * * *

SEQUENCE LISTING

```
<160> NUMBER OF SEQ ID NOS: 16

<210> SEQ ID NO 1
<211> LENGTH: 2676
<212> TYPE: DNA
<213> ORGANISM: Mus musculus
<220> FEATURE:
<221> NAME/KEY: CDS
<222> LOCATION: (104)..(1231)

<400> SEQUENCE: 1
gtctctcgga cggtacatgc actaatattt cacttggcat tactcaaaag caaaagaag       60 aaataagaac aagggaaaaa aaaagattgt gctgattttt aaa atg atg caa aaa      115
                                                 Met Met Gln Lys
                                                  1 ctg caa atg tat gtt tat att tac ctg ttc atg ctg att gct gct ggc      163
Leu Gln Met Tyr Val Tyr Ile Tyr Leu Phe Met Leu Ile Ala Ala Gly
 5               10                  15                  20 cca gtg gat cta aat gag ggc agt gag aga gaa gaa aat gtg gaa aaa      211
Pro Val Asp Leu Asn Glu Gly Ser Glu Arg Glu Glu Asn Val Glu Lys
                 25                  30                  35 gag ggg ctg tgt aat gca tgt gcg tgg aga caa aac acg agg tac tcc      259
Glu Gly Leu Cys Asn Ala Cys Ala Trp Arg Gln Asn Thr Arg Tyr Ser
             40                  45                  50 aga ata gaa gcc ata aaa att caa atc ctc agt aag ctg cgc ctg gaa      307
Arg Ile Glu Ala Ile Lys Ile Gln Ile Leu Ser Lys Leu Arg Leu Glu
         55                  60                  65 aca gct cct aac atc agc aaa gat gct ata aga caa ctt ctg cca aga      355
Thr Ala Pro Asn Ile Ser Lys Asp Ala Ile Arg Gln Leu Leu Pro Arg
     70                  75                  80 gcg cct cca ctc cgg gaa ctg atc gat cag tac gac gtc cag agg gat      403
Ala Pro Pro Leu Arg Glu Leu Ile Asp Gln Tyr Asp Val Gln Arg Asp
 85                  90                  95                 100 gac agc agt gat ggc tct ttg gaa gat gac gat tat cac gct acc acg      451
Asp Ser Ser Asp Gly Ser Leu Glu Asp Asp Asp Tyr His Ala Thr Thr
                105                 110                 115 gaa aca atc att acc atg cct aca gag tct gac ttt cta atg caa gcg      499
Glu Thr Ile Ile Thr Met Pro Thr Glu Ser Asp Phe Leu Met Gln Ala
            120                 125                 130 gat ggc aag ccc aaa tgt tgc ttt ttt aaa ttt agc tct aaa ata cag      547
Asp Gly Lys Pro Lys Cys Cys Phe Phe Lys Phe Ser Ser Lys Ile Gln
```

```
                    135              140                  145
tac aac aaa gta gta aaa gcc caa ctg tgg ata tat ctc aga ccc gtc    595
Tyr Asn Lys Val Val Lys Ala Gln Leu Trp Ile Tyr Leu Arg Pro Val
        150                 155             160 aag act cct aca aca gtg ttt gtg caa atc ctg aga ctc atc aaa ccc    643
Lys Thr Pro Thr Thr Val Phe Val Gln Ile Leu Arg Leu Ile Lys Pro
165                 170                 175                 180 atg aaa gac ggt aca agg tat act gga atc cga tct ctg aaa ctt gac    691
Met Lys Asp Gly Thr Arg Tyr Thr Gly Ile Arg Ser Leu Lys Leu Asp
                185                 190                 195 atg agc cca ggc act ggt att tgg cag agt att gat gtg aag aca gtg    739
Met Ser Pro Gly Thr Gly Ile Trp Gln Ser Ile Asp Val Lys Thr Val
            200                 205                 210 ttg caa aat tgg ctc aaa cag cct gaa tcc aac tta ggc att gaa atc    787
Leu Gln Asn Trp Leu Lys Gln Pro Glu Ser Asn Leu Gly Ile Glu Ile
        215                 220                 225 aaa gct ttg gat gag aat ggc cat gat ctt gct gta acc ttc cca gga    835
Lys Ala Leu Asp Glu Asn Gly His Asp Leu Ala Val Thr Phe Pro Gly
230                 235                 240 cca gga gaa gat ggg ctg aat ccc ttt tta gaa gtc aag gtg aca gac    883
Pro Gly Glu Asp Gly Leu Asn Pro Phe Leu Glu Val Lys Val Thr Asp
245                 250                 255                 260 aca ccc aag agg tcc cgg aga gac ttt ggg ctt gac tgc gat gag cac    931
Thr Pro Lys Arg Ser Arg Arg Asp Phe Gly Leu Asp Cys Asp Glu His
                265                 270                 275 tcc acg gaa tcc cgg tgc tgc cgc tac ccc ctc acg gtc gat ttt gaa    979
Ser Thr Glu Ser Arg Cys Cys Arg Tyr Pro Leu Thr Val Asp Phe Glu
            280                 285                 290 gcc ttt gga tgg gac tgg att atc gca ccc aaa aga tat aag gcc aat    1027
Ala Phe Gly Trp Asp Trp Ile Ile Ala Pro Lys Arg Tyr Lys Ala Asn
        295                 300                 305 tac tgc tca gga gag tgt gaa ttt gtg ttt tta caa aaa tat ccg cat    1075
Tyr Cys Ser Gly Glu Cys Glu Phe Val Phe Leu Gln Lys Tyr Pro His
    310                 315                 320 act cat ctt gtg cac caa gca aac ccc aga ggc tca gca ggc cct tgc    1123
Thr His Leu Val His Gln Ala Asn Pro Arg Gly Ser Ala Gly Pro Cys
325                 330                 335                 340 tgc act ccg aca aaa atg tct ccc att aat atg cta tat ttt aat ggc    1171
Cys Thr Pro Thr Lys Met Ser Pro Ile Asn Met Leu Tyr Phe Asn Gly
                345                 350                 355 aaa gaa caa ata ata tat ggg aaa att cca gcc atg gta gta gac cgc    1219
Lys Glu Gln Ile Ile Tyr Gly Lys Ile Pro Ala Met Val Val Asp Arg
            360                 365                 370 tgt ggg tgc tca tgagctttgc attaggttag aaacttccca agtcatggaa        1271
Cys Gly Cys Ser
            375 ggtcttcccc tcaatttcga aactgtgaat tcaagcacca caggctgtag gccttgagta  1331 tgctctagta acgtaagcac aagctacagt gtatgaacta aaagagagaa tagatgcaat  1391 ggttggcatt caaccaccaa aataaaccat actataggat gttgtatgat ttccagagtt  1451 tttgaaatag atggagatca aattacattt atgtccatat atgtatatta caactacaat  1511 ctaggcaagg aagtgagagc acatcttgtg gtctgctgag ttaggagggt atgattaaaa  1571 ggtaaagtct tatttcctaa cagtttcact taatatttac agaagaatct atatgtagcc  1631 tttgtaaagt gtaggattgt tatcatttaa aaacatcatg tacacttata tttgtattgt  1691 atacttggta agataaaatt ccacaaagta ggaatggggc ctcacataca cattgccatt  1751 cctattataa ttggacaatc caccacggtg ctaatgcagt gctgaatggc tcctactgga  1811
```

-continued

```
cctctcgata gaacactcta caaagtacga gtctctctct cccttccagg tgcatctcca    1871
cacacacagc actaagtgtt caatgcattt tctttaagga aagaagaatc ttttttttcta   1931
gaggtcaact ttcagtcaac tctagcacag cgggagtgac tgctgcatct taaaaggcag    1991
ccaaacagta ttcattttt aatctaaatt tcaaaatcac tgtctgcctt tatcacatgg     2051
caattttgtg gtaaaataat ggaaatgact ggttctatca atattgtata aaagactctg    2111
aaacaattac atttatataa tatgtataca atattgtttt gtaaataagt gtctccttt     2171
atatttactt tggtatattt ttacactaat gaaatttcaa atcattaaag tacaaagaca    2231
tgtcatgtat cacaaaaaag gtgactgctt ctatttcaga gtgaattagc agattcaata    2291
gtggtcttaa aactctgtat gttaagatta gaaggttata ttacaatcaa tttatgtatt    2351
ttttacatta tcaacttatg gtttcatggt ggctgtatct atgaatgtgg ctcccagtca    2411
aatttcaatg ccccaccatt ttaaaaatta caagcattac taaacatacc aacatgtatc    2471
taaagaaata caaatatggt atctcaataa cagctacttt tttatttat aatttgacaa     2531
tgaatacatt tcttttattt acttcagttt tataaattgg aactttgttt atcaaatgta    2591
ttgtactcat agctaaatga aattattct tacataaaaa tgtgtagaaa ctataaatta     2651
aagtgttttc acatttttga aaggc                                          2676
```

<210> SEQ ID NO 2
<211> LENGTH: 376
<212> TYPE: PRT
<213> ORGANISM: Mus musculus

<400> SEQUENCE: 2

```
Met Met Gln Lys Leu Gln Met Tyr Val Tyr Ile Tyr Leu Phe Met Leu
1               5                   10                  15

Ile Ala Ala Gly Pro Val Asp Leu Asn Glu Gly Ser Glu Arg Glu Glu
                20                  25                  30

Asn Val Glu Lys Glu Gly Leu Cys Asn Ala Cys Ala Trp Arg Gln Asn
            35                  40                  45

Thr Arg Tyr Ser Arg Ile Glu Ala Ile Lys Ile Gln Ile Leu Ser Lys
        50                  55                  60

Leu Arg Leu Glu Thr Ala Pro Asn Ile Ser Lys Asp Ala Ile Arg Gln
65                  70                  75                  80

Leu Leu Pro Arg Ala Pro Pro Leu Arg Glu Leu Ile Asp Gln Tyr Asp
                85                  90                  95

Val Gln Arg Asp Asp Ser Ser Asp Gly Ser Leu Glu Asp Asp Asp Tyr
            100                 105                 110

His Ala Thr Thr Glu Thr Ile Ile Thr Met Pro Thr Glu Ser Asp Phe
        115                 120                 125

Leu Met Gln Ala Asp Gly Lys Pro Lys Cys Cys Phe Phe Lys Phe Ser
    130                 135                 140

Ser Lys Ile Gln Tyr Asn Lys Val Lys Ala Gln Leu Trp Ile Tyr
145                 150                 155                 160

Leu Arg Pro Val Lys Thr Pro Thr Thr Val Phe Val Gln Ile Leu Arg
                165                 170                 175

Leu Ile Lys Pro Met Lys Asp Gly Thr Arg Tyr Thr Gly Ile Arg Ser
            180                 185                 190

Leu Lys Leu Asp Met Ser Pro Gly Thr Gly Ile Trp Gln Ser Ile Asp
        195                 200                 205

Val Lys Thr Val Leu Gln Asn Trp Leu Lys Gln Pro Glu Ser Asn Leu
```

-continued

```
                    210                 215                 220
Gly Ile Glu Ile Lys Ala Leu Asp Glu Asn Gly His Asp Leu Ala Val
225                 230                 235                 240

Thr Phe Pro Gly Pro Gly Glu Asp Gly Leu Asn Pro Phe Leu Glu Val
                245                 250                 255

Lys Val Thr Asp Thr Pro Lys Arg Ser Arg Arg Asp Phe Gly Leu Asp
                260                 265                 270

Cys Asp Glu His Ser Thr Glu Ser Arg Cys Cys Arg Tyr Pro Leu Thr
                275                 280                 285

Val Asp Phe Glu Ala Phe Gly Trp Asp Trp Ile Ile Ala Pro Lys Arg
                290                 295                 300

Tyr Lys Ala Asn Tyr Cys Ser Gly Glu Cys Glu Phe Val Phe Leu Gln
305                 310                 315                 320

Lys Tyr Pro His Thr His Leu Val His Gln Ala Asn Pro Arg Gly Ser
                325                 330                 335

Ala Gly Pro Cys Cys Thr Pro Thr Lys Met Ser Pro Ile Asn Met Leu
                340                 345                 350

Tyr Phe Asn Gly Lys Glu Gln Ile Ile Tyr Gly Lys Ile Pro Ala Met
                355                 360                 365

Val Val Asp Arg Cys Gly Cys Ser
                370                 375
```

<210> SEQ ID NO 3
<211> LENGTH: 2743
<212> TYPE: DNA
<213> ORGANISM: Homo sapiens
<220> FEATURE:
<221> NAME/KEY: CDS
<222> LOCATION: (59)..(1183)

<400> SEQUENCE: 3

```
aagaaaagta aaggaagaa acaagaacaa gaaaaaagat tatattgatt ttaaaatc        58 atg caa aaa ctg caa ctc tgt gtt tat att tac ctg ttt atg ctg att     106
Met Gln Lys Leu Gln Leu Cys Val Tyr Ile Tyr Leu Phe Met Leu Ile
1               5                   10                  15 gtt gct ggt cca gtg gat cta aat gag aac agt gag caa aaa gaa aat     154
Val Ala Gly Pro Val Asp Leu Asn Glu Asn Ser Glu Gln Lys Glu Asn
            20                  25                  30 gtg gaa aaa gag ggg ctg tgt aat gca tgt act tgg aga caa aac act     202
Val Glu Lys Glu Gly Leu Cys Asn Ala Cys Thr Trp Arg Gln Asn Thr
        35                  40                  45 aaa tct tca aga ata gaa gcc att aag ata caa atc ctc agt aaa ctt     250
Lys Ser Ser Arg Ile Glu Ala Ile Lys Ile Gln Ile Leu Ser Lys Leu
    50                  55                  60 cgt ctg gaa aca gct cct aac atc agc aaa gat gtt ata aga caa ctt     298
Arg Leu Glu Thr Ala Pro Asn Ile Ser Lys Asp Val Ile Arg Gln Leu
65                  70                  75                  80 tta ccc aaa gct cct cca ctc cgg gaa ctg att gat cag tat gat gtc     346
Leu Pro Lys Ala Pro Pro Leu Arg Glu Leu Ile Asp Gln Tyr Asp Val
                85                  90                  95 cag agg gat gac agc agc gat ggc tct ttg gaa gat gac gat tat cac     394
Gln Arg Asp Asp Ser Ser Asp Gly Ser Leu Glu Asp Asp Tyr His
            100                 105                 110 gct aca acg gaa aca atc att acc atg cct aca gag tct gat ttt cta     442
Ala Thr Thr Glu Thr Ile Ile Thr Met Pro Thr Glu Ser Asp Phe Leu
        115                 120                 125 atg caa gtg gat gga aaa ccc aaa tgt tgc ttc ttt aaa ttt agc tct     490
Met Gln Val Asp Gly Lys Pro Lys Cys Cys Phe Phe Lys Phe Ser Ser
```

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 130 |     |     |     |     | 135 |     |     |     |     | 140 |     |     |     |     |     |      |
| aaa | ata | caa | tac | aat | aaa | gta | gta | aag | gcc | caa | cta | tgg | ata | tat | ttg | 538  |
| Lys | Ile | Gln | Tyr | Asn | Lys | Val | Val | Lys | Ala | Gln | Leu | Trp | Ile | Tyr | Leu |      |
| 145 |     |     |     | 150 |     |     |     |     | 155 |     |     |     |     | 160 |     |      |
| aga | ccc | gtc | gag | act | cct | aca | aca | gtg | ttt | gtg | caa | atc | ctg | aga | ctc | 586  |
| Arg | Pro | Val | Glu | Thr | Pro | Thr | Thr | Val | Phe | Val | Gln | Ile | Leu | Arg | Leu |      |
|     |     |     |     | 165 |     |     |     |     | 170 |     |     |     |     | 175 |     |      |
| atc | aaa | cct | atg | aaa | gac | ggt | aca | agg | tat | act | gga | atc | cga | tct | ctg | 634  |
| Ile | Lys | Pro | Met | Lys | Asp | Gly | Thr | Arg | Tyr | Thr | Gly | Ile | Arg | Ser | Leu |      |
|     |     |     | 180 |     |     |     |     | 185 |     |     |     |     | 190 |     |     |      |
| aaa | ctt | gac | atg | aac | cca | ggc | act | ggt | att | tgg | cag | agc | att | gat | gtg | 682  |
| Lys | Leu | Asp | Met | Asn | Pro | Gly | Thr | Gly | Ile | Trp | Gln | Ser | Ile | Asp | Val |      |
|     |     | 195 |     |     |     |     | 200 |     |     |     |     | 205 |     |     |     |      |
| aag | aca | gtg | ttg | caa | aat | tgg | ctc | aaa | caa | cct | gaa | tcc | aac | tta | ggc | 730  |
| Lys | Thr | Val | Leu | Gln | Asn | Trp | Leu | Lys | Gln | Pro | Glu | Ser | Asn | Leu | Gly |      |
|     | 210 |     |     |     |     | 215 |     |     |     |     | 220 |     |     |     |     |      |
| att | gaa | ata | aaa | gct | tta | gat | gag | aat | ggt | cat | gat | ctt | gct | gta | acc | 778  |
| Ile | Glu | Ile | Lys | Ala | Leu | Asp | Glu | Asn | Gly | His | Asp | Leu | Ala | Val | Thr |      |
| 225 |     |     |     |     | 230 |     |     |     |     | 235 |     |     |     |     | 240 |      |
| ttc | cca | gga | cca | gga | gaa | gat | ggg | ctg | aat | ccg | ttt | tta | gag | gtc | aag | 826  |
| Phe | Pro | Gly | Pro | Gly | Glu | Asp | Gly | Leu | Asn | Pro | Phe | Leu | Glu | Val | Lys |      |
|     |     |     |     | 245 |     |     |     |     | 250 |     |     |     |     | 255 |     |      |
| gta | aca | gac | aca | cca | aaa | aga | tcc | aga | agg | gat | ttt | ggt | ctt | gac | tgt | 874  |
| Val | Thr | Asp | Thr | Pro | Lys | Arg | Ser | Arg | Arg | Asp | Phe | Gly | Leu | Asp | Cys |      |
|     |     |     | 260 |     |     |     |     | 265 |     |     |     |     | 270 |     |     |      |
| gat | gag | cac | tca | aca | gaa | tca | cga | tgc | tgt | cgt | tac | cct | cta | act | gtg | 922  |
| Asp | Glu | His | Ser | Thr | Glu | Ser | Arg | Cys | Cys | Arg | Tyr | Pro | Leu | Thr | Val |      |
|     |     | 275 |     |     |     |     | 280 |     |     |     |     | 285 |     |     |     |      |
| gat | ttt | gaa | gct | ttt | gga | tgg | gat | tgg | att | atc | gct | cct | aaa | aga | tat | 970  |
| Asp | Phe | Glu | Ala | Phe | Gly | Trp | Asp | Trp | Ile | Ile | Ala | Pro | Lys | Arg | Tyr |      |
|     | 290 |     |     |     |     | 295 |     |     |     |     | 300 |     |     |     |     |      |
| aag | gcc | aat | tac | tgc | tct | gga | gag | tgt | gaa | ttt | gta | ttt | tta | caa | aaa | 1018 |
| Lys | Ala | Asn | Tyr | Cys | Ser | Gly | Glu | Cys | Glu | Phe | Val | Phe | Leu | Gln | Lys |      |
| 305 |     |     |     |     | 310 |     |     |     |     | 315 |     |     |     |     | 320 |      |
| tat | cct | cat | act | cat | ctg | gta | cac | caa | gca | aac | ccc | aga | ggt | tca | gca | 1066 |
| Tyr | Pro | His | Thr | His | Leu | Val | His | Gln | Ala | Asn | Pro | Arg | Gly | Ser | Ala |      |
|     |     |     |     | 325 |     |     |     |     | 330 |     |     |     |     | 335 |     |      |
| ggc | cct | tgc | tgt | act | ccc | aca | aag | atg | tct | cca | att | aat | atg | cta | tat | 1114 |
| Gly | Pro | Cys | Cys | Thr | Pro | Thr | Lys | Met | Ser | Pro | Ile | Asn | Met | Leu | Tyr |      |
|     |     |     | 340 |     |     |     |     | 345 |     |     |     |     | 350 |     |     |      |
| ttt | aat | ggc | aaa | gaa | caa | ata | ata | tat | ggg | aaa | att | cca | gcg | atg | gta | 1162 |
| Phe | Asn | Gly | Lys | Glu | Gln | Ile | Ile | Tyr | Gly | Lys | Ile | Pro | Ala | Met | Val |      |
|     |     | 355 |     |     |     |     | 360 |     |     |     |     | 365 |     |     |     |      |
| gta | gac | cgc | tgt | ggg | tgc | tca | tgagtttat attaagcgtt cataacttcc           |     |     |     |     |     |     |     | 1213 |
| Val | Asp | Arg | Cys | Gly | Cys | Ser |     |     |     |     |     |     |     |     |     |      |
|     |     | 370 |     |     |     | 375 |     |     |     |     |     |     |     |     |     |      | taaacatgg aaggttttcc cctcaacaat tttgaagctg tgaaattaag taccacaggc    1273 tataggccta gagtatgcta cagtcactta agcataagct acagtatgta aactaaaagg    1333 gggaatatat gcaatggttg gcatttaacc atccaaacaa atcatacaag aaagttttat    1393 gatttccaga gttttgagc tagaaggaga tcaaattaca tttatgttcc tatatattac    1453 aacatcggcg aggaaatgaa agcgattctc cttgagttct gatgaattaa aggagtatgc    1513 tttaaagtct atttctttaa agttttgttt aatatttaca gaaaaatcca catacagtat    1573 tggtaaaatg caggattgtt atataccatc attcgaatca tccttaaaca cttgaattta    1633 tattgtatgg tagtatactt ggtaagataa aattccacaa aaataggat ggtgcagcat    1693 atgcaatttc cattcctatt ataattgaca cagtacatta acaatccatg ccaacggtgc    1753

-continued

```
taatacgata ggctgaatgt ctgaggctac caggtttatc acataaaaaa cattcagtaa    1813
aatagtaagt ttctcttttc ttcaggtgca ttttcctaca cctccaaatg aggaatggat    1873
tttctttaat gtaagaagaa tcattttct agaggttggc tttcaattct gtagcatact     1933
tggagaaact gcattatctt aaaaggcagt caaatggtgt ttgtttttat caaaatgtca    1993
aaataacata cttggagaag tatgtaattt tgtctttgga aaattacaac actgcctttg    2053
caacactgca gttttatgg taaaataata gaaatgatcg actctatcaa tattgtataa     2113
aaagactgaa acaatgcatt tatataatat gtatacaata ttgttttgta aataagtgtc    2173
tcctttttta tttactttgg tatatttta cactaaggac atttcaaatt aagtactaag     2233
gcacaaagac atgtcatgca tcacagaaaa gcaactactt atatttcaga gcaaattagc    2293
agattaaata gtggtcttaa aactccatat gttaatgatt agatggttat attacaatca    2353
ttttatattt ttttacatga ttaacattca cttatggatt catgatggct gtataaagtg    2413
aatttgaaat ttcaatggtt tactgtcatt gtgtttaaat ctcaacgttc cattattta    2473 atacttgcaa aaacattact aagtatacca aaataattga ctctattatc tgaaatgaag    2533
aataaactga tgctatctca acaataactg ttactttat tttataattt gataatgaat     2593
atatttctgc atttatttac ttctgttttg taaattggga ttttgttaat caaatttatt    2653
gtactatgac taaatgaaat tatttcttac atctaatttg tagaaacagt ataagttata    2713
ttaaagtgtt ttcacatttt tttgaaagac                                     2743
```

<210> SEQ ID NO 4
<211> LENGTH: 375
<212> TYPE: PRT
<213> ORGANISM: Homo sapiens

<400> SEQUENCE: 4

```
Met Gln Lys Leu Gln Leu Cys Val Tyr Ile Tyr Leu Phe Met Leu Ile
 1               5                  10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190
```

-continued

```
Lys Leu Asp Met Asn Pro Gly Thr Gly Ile Trp Gln Ser Ile Asp Val
            195                 200                 205

Lys Thr Val Leu Gln Asn Trp Leu Lys Gln Pro Glu Ser Asn Leu Gly
        210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
        355                 360                 365

Val Asp Arg Cys Gly Cys Ser
    370                 375

<210> SEQ ID NO 5
<211> LENGTH: 1128
<212> TYPE: DNA
<213> ORGANISM: Papio hamadryas
<220> FEATURE:
<221> NAME/KEY: CDS
<222> LOCATION: (1)..(1125)

<400> SEQUENCE: 5 atg caa aaa ctg caa ctc tgt gtt tat att tac ctg ttt atg ctg att      48
Met Gln Lys Leu Gln Leu Cys Val Tyr Ile Tyr Leu Phe Met Leu Ile
1               5                   10                  15 gtt gct ggt cca gtg gat cta aat gag aac agt gag caa aaa gaa aat      96
Val Ala Gly Pro Val Asp Leu Asn Glu Asn Ser Glu Gln Lys Glu Asn
            20                  25                  30 gtg gaa aaa gag ggg ctg tgt aat gca tgt act tgg aga caa aac act     144
Val Glu Lys Glu Gly Leu Cys Asn Ala Cys Thr Trp Arg Gln Asn Thr
        35                  40                  45 aaa tct tca aga ata gaa gcc att aaa ata caa atc ctc agt aaa ctt     192
Lys Ser Ser Arg Ile Glu Ala Ile Lys Ile Gln Ile Leu Ser Lys Leu
    50                  55                  60 cgt ctg gaa aca gct cct aac atc agc aaa gat gct ata aga caa ctt     240
Arg Leu Glu Thr Ala Pro Asn Ile Ser Lys Asp Ala Ile Arg Gln Leu
65                  70                  75                  80 tta ccc aaa gcg cct cca ctc cgg gaa ctg att gat cag tat gat gtc     288
Leu Pro Lys Ala Pro Pro Leu Arg Glu Leu Ile Asp Gln Tyr Asp Val
                85                  90                  95 cag agg gat gac agc agc gat ggc tct ttg gaa gat gac gat tat cac     336
Gln Arg Asp Asp Ser Ser Asp Gly Ser Leu Glu Asp Asp Asp Tyr His
            100                 105                 110 gct aca acg gaa aca atc att acc atg cct aca gag tct gat ttt tta     384
Ala Thr Thr Glu Thr Ile Ile Thr Met Pro Thr Glu Ser Asp Phe Leu
        115                 120                 125
```

```
atg caa gtg gat gga aaa ccc aaa tgt tgc ttc ttt aaa ttt agc tct      432
Met Gln Val Asp Gly Lys Pro Lys Cys Cys Phe Phe Lys Phe Ser Ser
    130                 135                 140 aaa ata caa tac aat aaa gtg gta aag gcc caa cta tgg ata tat ttg      480
Lys Ile Gln Tyr Asn Lys Val Val Lys Ala Gln Leu Trp Ile Tyr Leu
145                 150                 155                 160 aga ccc gtc gag act cct aca aca gtg ttt gtg caa atc ctg aga ctc      528
Arg Pro Val Glu Thr Pro Thr Thr Val Phe Val Gln Ile Leu Arg Leu
                165                 170                 175 atc aaa cct atg aaa gac ggt aca agg tat act gga atc cga tct ctg      576
Ile Lys Pro Met Lys Asp Gly Thr Arg Tyr Thr Gly Ile Arg Ser Leu
            180                 185                 190 aaa ctt gac atg aac cca ggc act ggt att tgg cag agc att gat gtg      624
Lys Leu Asp Met Asn Pro Gly Thr Gly Ile Trp Gln Ser Ile Asp Val
        195                 200                 205 aag aca gtg ttg caa aat tgg ctc aaa caa cct gaa tcc aac tta ggc      672
Lys Thr Val Leu Gln Asn Trp Leu Lys Gln Pro Glu Ser Asn Leu Gly
    210                 215                 220 att gaa ata aaa gct tta gat gag aat ggt cat gat ctt gct gta acc      720
Ile Glu Ile Lys Ala Leu Asp Glu Asn Gly His Asp Leu Ala Val Thr
225                 230                 235                 240 ttc cca gga cca gga gaa gat ggg ctg aat ccc ttt tta gag gtc aag      768
Phe Pro Gly Pro Gly Glu Asp Gly Leu Asn Pro Phe Leu Glu Val Lys
                245                 250                 255 gta aca gac aca ccc aaa aga tcc aga agg gat ttt ggt ctt gac tgt      816
Val Thr Asp Thr Pro Lys Arg Ser Arg Arg Asp Phe Gly Leu Asp Cys
            260                 265                 270 gat gag cac tca aca gaa tcg cga tgc tgt cgt tac cct cta act gtg      864
Asp Glu His Ser Thr Glu Ser Arg Cys Cys Arg Tyr Pro Leu Thr Val
        275                 280                 285 gat ttt gaa gct ctt gga tgg gat tgg att atc gct cct aaa aga tat      912
Asp Phe Glu Ala Leu Gly Trp Asp Trp Ile Ile Ala Pro Lys Arg Tyr
    290                 295                 300 aag gcc aat tac tgc tct gga gag tgt gaa ttt gta ttt tta caa aaa      960
Lys Ala Asn Tyr Cys Ser Gly Glu Cys Glu Phe Val Phe Leu Gln Lys
305                 310                 315                 320 tat cct cat act cat ctg gta cac caa gca aac ccc aga ggt tca gca     1008
Tyr Pro His Thr His Leu Val His Gln Ala Asn Pro Arg Gly Ser Ala
                325                 330                 335 ggc cct tgc tgt act ccc aca aag atg tct cca att aat atg cta tat     1056
Gly Pro Cys Cys Thr Pro Thr Lys Met Ser Pro Ile Asn Met Leu Tyr
            340                 345                 350 ttt aat ggc aaa gaa caa ata ata tat ggg aaa att cca gcc atg gta     1104
Phe Asn Gly Lys Glu Gln Ile Ile Tyr Gly Lys Ile Pro Ala Met Val
        355                 360                 365 gta gac cgc tgc ggg tgc tca tga                                     1128
Val Asp Arg Cys Gly Cys Ser
    370                 375

<210> SEQ ID NO 6
<211> LENGTH: 375
<212> TYPE: PRT
<213> ORGANISM: Papio hamadryas

<400> SEQUENCE: 6

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
```

```
                  35                  40                  45
Lys Ser Ser Arg Ile Glu Ala Ile Lys Ile Gln Ile Leu Ser Lys Leu
     50                  55                  60
Arg Leu Glu Thr Ala Pro Asn Ile Ser Lys Asp Ala Ile Arg Gln Leu
 65                  70                  75                  80
Leu Pro Lys Ala Pro Pro Leu Arg Glu Leu Ile Asp Gln Tyr Asp Val
                 85                  90                  95
Gln Arg Asp Asp Ser Asp Gly Ser Leu Glu Asp Asp Tyr His
                100                 105                 110
Ala Thr Thr Glu Thr Ile Ile Thr Met Pro Thr Glu Ser Asp Phe Leu
            115                 120                 125
Met Gln Val Asp Gly Lys Pro Lys Cys Cys Phe Phe Lys Phe Ser Ser
    130                 135                 140
Lys Ile Gln Tyr Asn Lys Val Val Lys Ala Gln Leu Trp Ile Tyr Leu
145                 150                 155                 160
Arg Pro Val Glu Thr Pro Thr Val Phe Val Gln Ile Leu Arg Leu
                165                 170                 175
Ile Lys Pro Met Lys Asp Gly Thr Arg Tyr Thr Gly Ile Arg Ser Leu
            180                 185                 190
Lys Leu Asp Met Asn Pro Gly Thr Gly Ile Trp Gln Ser Ile Asp Val
    195                 200                 205
Lys Thr Val Leu Gln Asn Trp Leu Lys Gln Pro Glu Ser Asn Leu Gly
210                 215                 220
Ile Glu Ile Lys Ala Leu Asp Glu Asn Gly His Asp Leu Ala Val Thr
225                 230                 235                 240
Phe Pro Gly Pro Gly Glu Asp Gly Leu Asn Pro Phe Leu Glu Val Lys
                245                 250                 255
Val Thr Asp Thr Pro Lys Arg Ser Arg Arg Asp Phe Gly Leu Asp Cys
            260                 265                 270
Asp Glu His Ser Thr Glu Ser Arg Cys Cys Arg Tyr Pro Leu Thr Val
    275                 280                 285
Asp Phe Glu Ala Leu Gly Trp Asp Trp Ile Ile Ala Pro Lys Arg Tyr
290                 295                 300
Lys Ala Asn Tyr Cys Ser Gly Glu Cys Glu Phe Val Phe Leu Gln Lys
305                 310                 315                 320
Tyr Pro His Thr His Leu Val His Gln Ala Asn Pro Arg Gly Ser Ala
                325                 330                 335
Gly Pro Cys Cys Thr Pro Thr Lys Met Ser Pro Ile Asn Met Leu Tyr
            340                 345                 350
Phe Asn Gly Lys Glu Gln Ile Ile Tyr Gly Lys Ile Pro Ala Met Val
    355                 360                 365
Val Asp Arg Cys Gly Cys Ser
    370                 375

<210> SEQ ID NO 7
<211> LENGTH: 1128
<212> TYPE: DNA
<213> ORGANISM: Bovine
<220> FEATURE:
<221> NAME/KEY: CDS
<222> LOCATION: (1)..(1125)

<400> SEQUENCE: 7 atg caa aaa ctg caa atc tct gtt tat att tac cta ttt atg ctg att    48
Met Gln Lys Leu Gln Ile Ser Val Tyr Ile Tyr Leu Phe Met Leu Ile
 1               5                  10                  15
```

-continued

| | |
|---|---|
| gtt gct ggc cca gtg gat ctg aat gag aac agc gag cag aag gaa aat<br>Val Ala Gly Pro Val Asp Leu Asn Glu Asn Ser Glu Gln Lys Glu Asn<br>20                       25                       30 | 96 |
| gtg gaa aaa gag ggg ctg tgt aat gca tgt ttg tgg agg gaa aac act<br>Val Glu Lys Glu Gly Leu Cys Asn Ala Cys Leu Trp Arg Glu Asn Thr<br>35                       40                       45 | 144 |
| aca tcg tca aga cta gaa gcc ata aaa atc caa atc ctc agt aaa ctt<br>Thr Ser Ser Arg Leu Glu Ala Ile Lys Ile Gln Ile Leu Ser Lys Leu<br>50                       55                       60 | 192 |
| cgc ctg gaa aca gct cct aac atc agc aaa gat gct atc aga caa ctt<br>Arg Leu Glu Thr Ala Pro Asn Ile Ser Lys Asp Ala Ile Arg Gln Leu<br>65                       70                       75                       80 | 240 |
| ttg ccc aag gct cct cca ctc ctg gaa ctg att gat cag ttc gat gtc<br>Leu Pro Lys Ala Pro Pro Leu Leu Glu Leu Ile Asp Gln Phe Asp Val<br>85                       90                       95 | 288 |
| cag aga gat gcc agc agt gac ggc tcc ttg gaa gac gat gac tac cac<br>Gln Arg Asp Ala Ser Ser Asp Gly Ser Leu Glu Asp Asp Asp Tyr His<br>100                      105                    110 | 336 |
| gcc agg acg gaa acg gtc att acc atg ccc acg gag tct gat ctt cta<br>Ala Arg Thr Glu Thr Val Ile Thr Met Pro Thr Glu Ser Asp Leu Leu<br>115                      120                    125 | 384 |
| acg caa gtg gaa gga aaa ccc aaa tgt tgc ttc ttt aaa ttt agc tct<br>Thr Gln Val Glu Gly Lys Pro Lys Cys Cys Phe Phe Lys Phe Ser Ser<br>130                      135                    140 | 432 |
| aag ata caa tac aat aaa cta gta aag gcc caa ctg tgg ata tat ctg<br>Lys Ile Gln Tyr Asn Lys Leu Val Lys Ala Gln Leu Trp Ile Tyr Leu<br>145                      150                    155                    160 | 480 |
| agg cct gtc aag act cct gcg aca gtg ttt gtg caa atc ctg aga ctc<br>Arg Pro Val Lys Thr Pro Ala Thr Val Phe Val Gln Ile Leu Arg Leu<br>165                      170                    175 | 528 |
| atc aaa ccc atg aaa gac ggt aca agg tat act gga atc cga tct ctg<br>Ile Lys Pro Met Lys Asp Gly Thr Arg Tyr Thr Gly Ile Arg Ser Leu<br>180                      185                    190 | 576 |
| aaa ctt gac atg aac cca ggc act ggt att tgg cag agc att gat gtg<br>Lys Leu Asp Met Asn Pro Gly Thr Gly Ile Trp Gln Ser Ile Asp Val<br>195                      200                    205 | 624 |
| aag aca gtg ttg cag aac tgg ctc aaa caa cct gaa tcc aac tta ggc<br>Lys Thr Val Leu Gln Asn Trp Leu Lys Gln Pro Glu Ser Asn Leu Gly<br>210                      215                    220 | 672 |
| att gaa atc aaa gct tta gat gag aat ggc cat gat ctt gct gta acc<br>Ile Glu Ile Lys Ala Leu Asp Glu Asn Gly His Asp Leu Ala Val Thr<br>225                      230                    235                    240 | 720 |
| ttc cca gaa cca gga gaa gat gga ctg act ccc ttt tta gaa gtc aag<br>Phe Pro Glu Pro Gly Glu Asp Gly Leu Thr Pro Phe Leu Glu Val Lys<br>245                      250                    255 | 768 |
| gta aca gac aca cca aaa aga tct agg aga gat ttt ggg ctt gat tgt<br>Val Thr Asp Thr Pro Lys Arg Ser Arg Arg Asp Phe Gly Leu Asp Cys<br>260                      265                    270 | 816 |
| gat gaa cac tcc aca gaa tct cga tgc tgt cgt tac cct cta act gtg<br>Asp Glu His Ser Thr Glu Ser Arg Cys Cys Arg Tyr Pro Leu Thr Val<br>275                      280                    285 | 864 |
| gat ttt gaa gct ttt gga tgg gat tgg att att gca cct aaa aga tat<br>Asp Phe Glu Ala Phe Gly Trp Asp Trp Ile Ile Ala Pro Lys Arg Tyr<br>290                      295                    300 | 912 |
| aag gcc aat tac tgc tct gga gaa tgt gaa ttt gta ttt ttg caa aag<br>Lys Ala Asn Tyr Cys Ser Gly Glu Cys Glu Phe Val Phe Leu Gln Lys<br>305                      310                    315                    320 | 960 |
| tat cct cat acc cat ctt gtg cac caa gca aac ccc aga ggt tca gcc<br>Tyr Pro His Thr His Leu Val His Gln Ala Asn Pro Arg Gly Ser Ala | 1008 |

-continued

```
                325                 330                 335
ggc ccc tgc tgt act cct aca aag atg tct cca att aat atg cta tat    1056
Gly Pro Cys Cys Thr Pro Thr Lys Met Ser Pro Ile Asn Met Leu Tyr
            340                 345                 350 ttt aat ggc gaa gga caa ata ata tac ggg aag att cca gcc atg gta    1104
Phe Asn Gly Glu Gly Gln Ile Ile Tyr Gly Lys Ile Pro Ala Met Val
        355                 360                 365 gta gat cgc tgt ggg tgt tca tga                                    1128
Val Asp Arg Cys Gly Cys Ser
    370                 375

<210> SEQ ID NO 8
<211> LENGTH: 375
<212> TYPE: PRT
<213> ORGANISM: Bovine

<400> SEQUENCE: 8

Met Gln Lys Leu Gln Ile Ser Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Leu Trp Arg Glu Asn Thr
        35                  40                  45

Thr Ser Ser Arg Leu Glu Ala Ile Lys Ile Gln Ile Leu Ser Lys Leu
    50                  55                  60

Arg Leu Glu Thr Ala Pro Asn Ile Ser Lys Asp Ala Ile Arg Gln Leu
65                  70                  75                  80

Leu Pro Lys Ala Pro Pro Leu Leu Glu Leu Ile Asp Gln Phe Asp Val
                85                  90                  95

Gln Arg Asp Ala Ser Ser Asp Gly Ser Leu Glu Asp Asp Tyr His
            100                 105                 110

Ala Arg Thr Glu Thr Val Ile Thr Met Pro Thr Glu Ser Asp Leu Leu
        115                 120                 125

Thr Gln Val Glu Gly Lys Pro Lys Cys Cys Phe Phe Lys Phe Ser Ser
    130                 135                 140

Lys Ile Gln Tyr Asn Lys Leu Val Lys Ala Gln Leu Trp Ile Tyr Leu
145                 150                 155                 160

Arg Pro Val Lys Thr Pro Ala Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Glu Pro Gly Glu Asp Gly Leu Thr Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
    290                 295                 300
```

-continued

```
Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
                340                 345                 350

Phe Asn Gly Glu Gly Gln Ile Ile Tyr Gly Lys Ile Pro Ala Met Val
            355                 360                 365

Val Asp Arg Cys Gly Cys Ser
    370                 375

<210> SEQ ID NO 9
<211> LENGTH: 1128
<212> TYPE: DNA
<213> ORGANISM: Gallus gallus
<220> FEATURE:
<221> NAME/KEY: CDS
<222> LOCATION: (1)..(1125)

<400> SEQUENCE: 9
```

| | | | | | | | | | | | | | | | | |
|---|---|---|---|---|---|---|---|---|---|---|---|---|---|---|---|---|
| atg | caa | aag | ctg | gca | gtc | tat | gtt | tat | att | tac | ctg | ttc | atg | cag | atc | 48 |
| Met | Gln | Lys | Leu | Ala | Val | Tyr | Val | Tyr | Ile | Tyr | Leu | Phe | Met | Gln | Ile | |
| 1 | | | | 5 | | | | | 10 | | | | | 15 | | |
| gcg | gtt | gat | ccg | gtg | gct | ctg | gat | ggc | agt | agt | cag | ccc | aca | gag | aac | 96 |
| Ala | Val | Asp | Pro | Val | Ala | Leu | Asp | Gly | Ser | Ser | Gln | Pro | Thr | Glu | Asn | |
| | | | 20 | | | | | 25 | | | | | 30 | | | |
| gct | gaa | aaa | gac | gga | ctg | tgc | aat | gct | tgt | acg | tgg | aga | cag | aat | aca | 144 |
| Ala | Glu | Lys | Asp | Gly | Leu | Cys | Asn | Ala | Cys | Thr | Trp | Arg | Gln | Asn | Thr | |
| | | 35 | | | | | 40 | | | | | 45 | | | | |
| aaa | tcc | tcc | aga | ata | gaa | gcc | ata | aaa | att | caa | atc | ctc | agc | aaa | ctg | 192 |
| Lys | Ser | Ser | Arg | Ile | Glu | Ala | Ile | Lys | Ile | Gln | Ile | Leu | Ser | Lys | Leu | |
| | 50 | | | | | 55 | | | | | 60 | | | | | |
| cgc | ctg | gaa | caa | gca | cct | aac | att | agc | agg | gac | gtt | att | aag | cag | ctt | 240 |
| Arg | Leu | Glu | Gln | Ala | Pro | Asn | Ile | Ser | Arg | Asp | Val | Ile | Lys | Gln | Leu | |
| 65 | | | | | 70 | | | | | 75 | | | | | 80 | |
| tta | ccc | aaa | gct | cct | cca | ctg | cag | gaa | ctg | att | gat | cag | tat | gat | gtc | 288 |
| Leu | Pro | Lys | Ala | Pro | Pro | Leu | Gln | Glu | Leu | Ile | Asp | Gln | Tyr | Asp | Val | |
| | | | | 85 | | | | | 90 | | | | | 95 | | |
| cag | agg | gac | gac | agt | agc | gat | ggc | tct | ttg | gaa | gac | gat | gac | tat | cat | 336 |
| Gln | Arg | Asp | Asp | Ser | Ser | Asp | Gly | Ser | Leu | Glu | Asp | Asp | Asp | Tyr | His | |
| | | | 100 | | | | | 105 | | | | | 110 | | | |
| gcc | aca | acc | gag | acg | att | atc | aca | atg | cct | acg | gag | tct | gat | ttt | ctt | 384 |
| Ala | Thr | Thr | Glu | Thr | Ile | Ile | Thr | Met | Pro | Thr | Glu | Ser | Asp | Phe | Leu | |
| | | 115 | | | | | 120 | | | | | 125 | | | | |
| gta | caa | atg | gag | gga | aaa | cca | aaa | tgt | tgc | ttc | ttt | aag | ttt | agc | tct | 432 |
| Val | Gln | Met | Glu | Gly | Lys | Pro | Lys | Cys | Cys | Phe | Phe | Lys | Phe | Ser | Ser | |
| | 130 | | | | | 135 | | | | | 140 | | | | | |
| aaa | ata | caa | tat | aac | aaa | gta | gta | aag | gca | caa | tta | tgg | ata | tac | ttg | 480 |
| Lys | Ile | Gln | Tyr | Asn | Lys | Val | Val | Lys | Ala | Gln | Leu | Trp | Ile | Tyr | Leu | |
| 145 | | | | | 150 | | | | | 155 | | | | | 160 | |
| agg | caa | gtc | caa | aaa | cct | aca | acg | gtg | ttt | gtg | cag | atc | ctg | aga | ctc | 528 |
| Arg | Gln | Val | Gln | Lys | Pro | Thr | Thr | Val | Phe | Val | Gln | Ile | Leu | Arg | Leu | |
| | | | | 165 | | | | | 170 | | | | | 175 | | |
| att | aag | ccc | atg | aaa | gac | ggt | aca | aga | tat | act | gga | att | cga | tct | ttg | 576 |
| Ile | Lys | Pro | Met | Lys | Asp | Gly | Thr | Arg | Tyr | Thr | Gly | Ile | Arg | Ser | Leu | |
| | | | 180 | | | | | 185 | | | | | 190 | | | |
| aaa | ctt | gac | atg | aac | cca | ggc | act | ggt | atc | tgg | cag | agt | att | gat | gtg | 624 |
| Lys | Leu | Asp | Met | Asn | Pro | Gly | Thr | Gly | Ile | Trp | Gln | Ser | Ile | Asp | Val | |
| | | 195 | | | | | 200 | | | | | 205 | | | | |
| aag | aca | gtg | ctg | caa | aat | tgg | ctc | aaa | cag | cct | gaa | tcc | aat | tta | ggc | 672 |

```
Lys Thr Val Leu Gln Asn Trp Leu Lys Gln Pro Glu Ser Asn Leu Gly
            210                 215                 220 atc gaa ata aaa gct ttt gat gag act gga cga gat ctt gct gtc aca        720
Ile Glu Ile Lys Ala Phe Asp Glu Thr Gly Arg Asp Leu Ala Val Thr
225                 230                 235                 240 ttc cca gga cca gga gaa gat gga ttg aac cca ttt tta gag gtc aga        768
Phe Pro Gly Pro Gly Glu Asp Gly Leu Asn Pro Phe Leu Glu Val Arg
                245                 250                 255 gtt aca gac aca ccg aaa cgg tcc cgc aga gat ttt ggc ctt gac tgt        816
Val Thr Asp Thr Pro Lys Arg Ser Arg Arg Asp Phe Gly Leu Asp Cys
            260                 265                 270 gat gag cac tca acg gaa tcc cga tgt tgt cgc tac ccg ctg aca gtg        864
Asp Glu His Ser Thr Glu Ser Arg Cys Cys Arg Tyr Pro Leu Thr Val
        275                 280                 285 gat ttc gaa gct ttt gga tgg gac tgg att ata gca cct aaa aga tac        912
Asp Phe Glu Ala Phe Gly Trp Asp Trp Ile Ile Ala Pro Lys Arg Tyr
290                 295                 300 aaa gcc aat tac tgc tcc gga gaa tgc gaa ttt gtg ttt cta cag aaa        960
Lys Ala Asn Tyr Cys Ser Gly Glu Cys Glu Phe Val Phe Leu Gln Lys
305                 310                 315                 320 tac ccg cac act cac ctg gta cac caa gca aat ccc aga ggc tca gca       1008
Tyr Pro His Thr His Leu Val His Gln Ala Asn Pro Arg Gly Ser Ala
                325                 330                 335 ggc cct tgc tgc aca ccc acc aag atg tcc cct ata aac atg ctg tat       1056
Gly Pro Cys Cys Thr Pro Thr Lys Met Ser Pro Ile Asn Met Leu Tyr
            340                 345                 350 ttc aat gga aaa gaa caa ata ata tat gga aag ata cca gcc atg gtt       1104
Phe Asn Gly Lys Glu Gln Ile Ile Tyr Gly Lys Ile Pro Ala Met Val
        355                 360                 365 gta gat cgt tgc ggg tgc tca tga                                       1128
Val Asp Arg Cys Gly Cys Ser
370                 375

<210> SEQ ID NO 10
<211> LENGTH: 375
<212> TYPE: PRT
<213> ORGANISM: Gallus gallus

<400> SEQUENCE: 10

Met Gln Lys Leu Ala Val Tyr Val Tyr Ile Tyr Leu Phe Met Gln Ile
1               5                   10                  15

Ala Val Asp Pro Val Ala Leu Asp Gly Ser Ser Gln Pro Thr Glu Asn
            20                  25                  30

Ala Glu Lys Asp Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Gln Ala Pro Asn Ile Ser Arg Asp Val Ile Lys Gln Leu
65                  70                  75                  80

Leu Pro Lys Ala Pro Pro Leu Gln Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
        115                 120                 125

Val Gln Met Glu Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
```

```
                145                 150                 155                 160
Arg Gln Val Gln Lys Pro Thr Thr Val Phe Val Gln Ile Leu Arg Leu
                165                 170                 175
Ile Lys Pro Met Lys Asp Gly Thr Arg Tyr Thr Gly Ile Arg Ser Leu
                180                 185                 190
Lys Leu Asp Met Asn Pro Gly Thr Gly Ile Trp Gln Ser Ile Asp Val
                195                 200                 205
Lys Thr Val Leu Gln Asn Trp Leu Lys Gln Pro Glu Ser Asn Leu Gly
                210                 215                 220
Ile Glu Ile Lys Ala Phe Asp Glu Thr Gly Arg Asp Leu Ala Val Thr
225                 230                 235                 240
Phe Pro Gly Pro Gly Glu Asp Gly Leu Asn Pro Phe Leu Glu Val Arg
                245                 250                 255
Val Thr Asp Thr Pro Lys Arg Ser Arg Arg Asp Phe Gly Leu Asp Cys
                260                 265                 270
Asp Glu His Ser Thr Glu Ser Arg Cys Cys Arg Tyr Pro Leu Thr Val
                275                 280                 285
Asp Phe Glu Ala Phe Gly Trp Asp Trp Ile Ile Ala Pro Lys Arg Tyr
                290                 295                 300
Lys Ala Asn Tyr Cys Ser Gly Glu Cys Glu Phe Val Phe Leu Gln Lys
305                 310                 315                 320
Tyr Pro His Thr His Leu Val His Gln Ala Asn Pro Arg Gly Ser Ala
                325                 330                 335
Gly Pro Cys Cys Thr Pro Thr Lys Met Ser Pro Ile Asn Met Leu Tyr
                340                 345                 350
Phe Asn Gly Lys Glu Gln Ile Ile Tyr Gly Lys Ile Pro Ala Met Val
                355                 360                 365
Val Asp Arg Cys Gly Cys Ser
370                 375

<210> SEQ ID NO 11
<211> LENGTH: 1131
<212> TYPE: DNA
<213> ORGANISM: Rattus norvegicus
<220> FEATURE:
<221> NAME/KEY: CDS
<222> LOCATION: (1)..(1128)

<400> SEQUENCE: 11 atg att caa aaa ccg caa atg tat gtt tat att tac ctg ttt gtg ctg      48
Met Ile Gln Lys Pro Gln Met Tyr Val Tyr Ile Tyr Leu Phe Val Leu
1               5                   10                  15 att gct gct ggc cca gtg gat cta aat gag gac agt gag aga gag gcg      96
Ile Ala Ala Gly Pro Val Asp Leu Asn Glu Asp Ser Glu Arg Glu Ala
                20                  25                  30 aat gtg gaa aaa gag ggg ctg tgt aat gcg tgt gcg tgg aga caa aac     144
Asn Val Glu Lys Glu Gly Leu Cys Asn Ala Cys Ala Trp Arg Gln Asn
            35                  40                  45 aca agg tac tcc aga ata gaa gcc ata aaa att caa atc ctc agt aaa     192
Thr Arg Tyr Ser Arg Ile Glu Ala Ile Lys Ile Gln Ile Leu Ser Lys
        50                  55                  60 ctc cgc ctg gaa aca gcg cct aac atc agc aaa gat gct ata aga caa     240
Leu Arg Leu Glu Thr Ala Pro Asn Ile Ser Lys Asp Ala Ile Arg Gln
65                  70                  75                  80 ctt ctg ccc aga gcg cct cca ctc cgg gaa ctg atc gat cag tac gac     288
Leu Leu Pro Arg Ala Pro Pro Leu Arg Glu Leu Ile Asp Gln Tyr Asp
                85                  90                  95
```

| | | |
|---|---|---|
| gtc cag agg gat gac agc agt gac ggc tct ttg gaa gat gac gat tat<br>Val Gln Arg Asp Asp Ser Ser Asp Gly Ser Leu Glu Asp Asp Asp Tyr<br>           100                         105                  110 | 336 |
| cac gct acc acg gaa aca atc att acc atg cct acc gag tct gac ttt<br>His Ala Thr Thr Glu Thr Ile Ile Thr Met Pro Thr Glu Ser Asp Phe<br>115                        120                       125 | 384 |
| cta atg caa gcg gat gga aag ccc aaa tgt tgc ttt ttt aaa ttt agc<br>Leu Met Gln Ala Asp Gly Lys Pro Lys Cys Cys Phe Phe Lys Phe Ser<br>130                        135                     140 | 432 |
| tct aaa ata cag tac aac aaa gtg gta aag gcc cag ctg tgg ata tat<br>Ser Lys Ile Gln Tyr Asn Lys Val Val Lys Ala Gln Leu Trp Ile Tyr<br>145                        150                     155                   160 | 480 |
| ctg aga gcc gtc aag act cct aca aca gtg ttt gtg caa atc ctg aga<br>Leu Arg Ala Val Lys Thr Pro Thr Thr Val Phe Val Gln Ile Leu Arg<br>                  165                     170                     175 | 528 |
| ctc atc aaa ccc atg aaa gac ggt aca agg tat acc gga atc cga tct<br>Leu Ile Lys Pro Met Lys Asp Gly Thr Arg Tyr Thr Gly Ile Arg Ser<br>                  180                     185                   190 | 576 |
| ctg aaa ctt gac atg agc cca ggc act ggt att tgg cag agt att gat<br>Leu Lys Leu Asp Met Ser Pro Gly Thr Gly Ile Trp Gln Ser Ile Asp<br>               195                     200                   205 | 624 |
| gtg aag aca gtg ttg caa aat tgg ctc aaa cag cct gaa tcc aac tta<br>Val Lys Thr Val Leu Gln Asn Trp Leu Lys Gln Pro Glu Ser Asn Leu<br>210                        215                     220 | 672 |
| ggc att gaa atc aaa gct ttg gat gag aat ggg cat gat ctt gct gta<br>Gly Ile Glu Ile Lys Ala Leu Asp Glu Asn Gly His Asp Leu Ala Val<br>225                        230                     235                   240 | 720 |
| acc ttc cca gga cca gga gaa gat ggg ctg aat ccc ttt tta gaa gtc<br>Thr Phe Pro Gly Pro Gly Glu Asp Gly Leu Asn Pro Phe Leu Glu Val<br>                       245                     250                   255 | 768 |
| aaa gta aca gac aca ccc aag agg tcc cgg aga gac ttt ggg ctt gac<br>Lys Val Thr Asp Thr Pro Lys Arg Ser Arg Arg Asp Phe Gly Leu Asp<br>                  260                     265                   270 | 816 |
| tgc gat gaa cac tcc acg gaa tcg cgg tgc tgt cgc tac ccc ctc acg<br>Cys Asp Glu His Ser Thr Glu Ser Arg Cys Cys Arg Tyr Pro Leu Thr<br>275                        280                     285 | 864 |
| gtc gat ttc gaa gcc ttt gga tgg gac tgg att att gca ccc aaa aga<br>Val Asp Phe Glu Ala Phe Gly Trp Asp Trp Ile Ile Ala Pro Lys Arg<br>290                        295                     300 | 912 |
| tat aag gct aat tac tgc tct gga gag tgt gaa ttt gtg ttc tta caa<br>Tyr Lys Ala Asn Tyr Cys Ser Gly Glu Cys Glu Phe Val Phe Leu Gln<br>305                        310                     315                   320 | 960 |
| aaa tat ccg cat act cat ctt gtg cac caa gca aac ccc aga ggc tcg<br>Lys Tyr Pro His Thr His Leu Val His Gln Ala Asn Pro Arg Gly Ser<br>                  325                     330                   335 | 1008 |
| gca ggc cct tgc tgc acg cca aca aaa atg tct ccc att aat atg cta<br>Ala Gly Pro Cys Cys Thr Pro Thr Lys Met Ser Pro Ile Asn Met Leu<br>                  340                     345                   350 | 1056 |
| tat ttt aat ggc aaa gaa caa ata ata tat ggg aaa att cca gcc atg<br>Tyr Phe Asn Gly Lys Glu Gln Ile Ile Tyr Gly Lys Ile Pro Ala Met<br>               355                     360                   365 | 1104 |
| gta gta gac cgg tgt ggg tgc tcg tga<br>Val Val Asp Arg Cys Gly Cys Ser<br>        370                     375 | 1131 |

<210> SEQ ID NO 12
<211> LENGTH: 376
<212> TYPE: PRT
<213> ORGANISM: Rattus norvegicus

<400> SEQUENCE: 12

Met Ile Gln Lys Pro Gln Met Tyr Val Tyr Ile Tyr Leu Phe Val Leu
1               5                   10                  15

Ile Ala Ala Gly Pro Val Asp Leu Asn Glu Asp Ser Glu Arg Glu Ala
            20                  25                  30

Asn Val Glu Lys Glu Gly Leu Cys Asn Ala Cys Ala Trp Arg Gln Asn
        35                  40                  45

Thr Arg Tyr Ser Arg Ile Glu Ala Ile Lys Ile Gln Ile Leu Ser Lys
    50                  55                  60

Leu Arg Leu Glu Thr Ala Pro Asn Ile Ser Lys Asp Ala Ile Arg Gln
65                  70                  75                  80

Leu Leu Pro Arg Ala Pro Pro Leu Arg Glu Leu Ile Asp Gln Tyr Asp
                85                  90                  95

Val Gln Arg Asp Asp Ser Ser Asp Gly Ser Leu Glu Asp Asp Asp Tyr
                100                 105                 110

His Ala Thr Thr Glu Thr Ile Ile Thr Met Pro Thr Glu Ser Asp Phe
            115                 120                 125

Leu Met Gln Ala Asp Gly Lys Pro Lys Cys Cys Phe Phe Lys Phe Ser
        130                 135                 140

Ser Lys Ile Gln Tyr Asn Lys Val Lys Ala Gln Leu Trp Ile Tyr
145                 150                 155                 160

Leu Arg Ala Val Lys Thr Pro Thr Thr Val Phe Val Gln Ile Leu Arg
                165                 170                 175

Leu Ile Lys Pro Met Lys Asp Gly Thr Arg Tyr Thr Gly Ile Arg Ser
            180                 185                 190

Leu Lys Leu Asp Met Ser Pro Gly Thr Gly Ile Trp Gln Ser Ile Asp
        195                 200                 205

Val Lys Thr Val Leu Gln Asn Trp Leu Lys Gln Pro Glu Ser Asn Leu
    210                 215                 220

Gly Ile Glu Ile Lys Ala Leu Asp Glu Asn Gly His Asp Leu Ala Val
225                 230                 235                 240

Thr Phe Pro Gly Pro Gly Glu Asp Gly Leu Asn Pro Phe Leu Glu Val
                245                 250                 255

Lys Val Thr Asp Thr Pro Lys Arg Ser Arg Arg Asp Phe Gly Leu Asp
            260                 265                 270

Cys Asp Glu His Ser Thr Glu Ser Arg Cys Cys Arg Tyr Pro Leu Thr
        275                 280                 285

Val Asp Phe Glu Ala Phe Gly Trp Asp Trp Ile Ile Ala Pro Lys Arg
    290                 295                 300

Tyr Lys Ala Asn Tyr Cys Ser Gly Glu Cys Glu Phe Val Phe Leu Gln
305                 310                 315                 320

Lys Tyr Pro His Thr His Leu Val His Gln Ala Asn Pro Arg Gly Ser
                325                 330                 335

Ala Gly Pro Cys Cys Thr Pro Thr Lys Met Ser Pro Ile Asn Met Leu
            340                 345                 350

Tyr Phe Asn Gly Lys Glu Gln Ile Ile Tyr Gly Lys Ile Pro Ala Met
        355                 360                 365

Val Val Asp Arg Cys Gly Cys Ser
    370                 375

<210> SEQ ID NO 13
<211> LENGTH: 1128
<212> TYPE: DNA
<213> ORGANISM: Meleagris gallopavo
<220> FEATURE:

```
<221> NAME/KEY: CDS
<222> LOCATION: (1)..(1125)

<400> SEQUENCE: 13 atg caa aag cta gca gtc tat gtt tat att tac ctg ttc atg cag att      48
Met Gln Lys Leu Ala Val Tyr Val Tyr Ile Tyr Leu Phe Met Gln Ile
1               5                  10                  15 tta gtt cat ccg gtg gct ctt gat ggc agt agt cag ccc aca gag aac      96
Leu Val His Pro Val Ala Leu Asp Gly Ser Ser Gln Pro Thr Glu Asn
            20                  25                  30 gct gaa aaa gac gga ctg tgc aat gct tgc acg tgg aga cag aat act     144
Ala Glu Lys Asp Gly Leu Cys Asn Ala Cys Thr Trp Arg Gln Asn Thr
        35                  40                  45 aaa tcc tcc aga ata gaa gcc ata aaa att caa atc ctc agc aaa ctg     192
Lys Ser Ser Arg Ile Glu Ala Ile Lys Ile Gln Ile Leu Ser Lys Leu
    50                  55                  60 cgc ctg gaa caa gca cct aac att agc agg gac gtt att aaa caa ctt     240
Arg Leu Glu Gln Ala Pro Asn Ile Ser Arg Asp Val Ile Lys Gln Leu
65                  70                  75                  80 tta ccc aaa gct cct ccg ctg cag gaa ctg att gat cag tat gac gtc     288
Leu Pro Lys Ala Pro Pro Leu Gln Glu Leu Ile Asp Gln Tyr Asp Val
                85                  90                  95 cag aga gac gac agt agc gat ggc tct ttg gaa gac gat gac tat cat     336
Gln Arg Asp Asp Ser Ser Asp Gly Ser Leu Glu Asp Asp Asp Tyr His
            100                 105                 110 gcc aca acc gaa acg att atc aca atg cct acg gag tct gat ttt ctt     384
Ala Thr Thr Glu Thr Ile Ile Thr Met Pro Thr Glu Ser Asp Phe Leu
        115                 120                 125 gta caa atg gag gga aaa cca aaa tgt tgc ttc ttt aag ttt agc tct     432
Val Gln Met Glu Gly Lys Pro Lys Cys Cys Phe Phe Lys Phe Ser Ser
    130                 135                 140 aaa ata caa tat aac aaa gta gta aag gca caa tta tgg ata tac ttg     480
Lys Ile Gln Tyr Asn Lys Val Val Lys Ala Gln Leu Trp Ile Tyr Leu
145                 150                 155                 160 agg caa gtc caa aaa cct aca acg gtg ttt gtg cag atc ctg aga ctc     528
Arg Gln Val Gln Lys Pro Thr Thr Val Phe Val Gln Ile Leu Arg Leu
                165                 170                 175 att aaa ccc atg aaa gac ggt aca aga tat act gga att cga tct ttg     576
Ile Lys Pro Met Lys Asp Gly Thr Arg Tyr Thr Gly Ile Arg Ser Leu
            180                 185                 190 aaa ctt gac atg aac cca ggc act ggt atc tgg cag agt att gat gtg     624
Lys Leu Asp Met Asn Pro Gly Thr Gly Ile Trp Gln Ser Ile Asp Val
        195                 200                 205 aag aca gtg ttg caa aat tgg ctc aaa cag cct gaa tcc aat tta ggc     672
Lys Thr Val Leu Gln Asn Trp Leu Lys Gln Pro Glu Ser Asn Leu Gly
    210                 215                 220 atc gaa ata aaa gct ttt gat gag aat gga cga gat ctt gct gta aca     720
Ile Glu Ile Lys Ala Phe Asp Glu Asn Gly Arg Asp Leu Ala Val Thr
225                 230                 235                 240 ttc cca gga cca ggt gaa gat gga ctg aac cca ttt tta gag gtc aga     768
Phe Pro Gly Pro Gly Glu Asp Gly Leu Asn Pro Phe Leu Glu Val Arg
                245                 250                 255 gtt aca gac aca cca aaa cgg tcc cgc aga gat ttt ggc ctt gac tgc     816
Val Thr Asp Thr Pro Lys Arg Ser Arg Arg Asp Phe Gly Leu Asp Cys
            260                 265                 270 gac gag cac tca acg gaa tct cga tgt tgt cgc tac ccg ctg aca gtg     864
Asp Glu His Ser Thr Glu Ser Arg Cys Cys Arg Tyr Pro Leu Thr Val
        275                 280                 285 gat ttt gaa gct ttt gga tgg gac tgg att ata gca cct aaa aga tac     912
Asp Phe Glu Ala Phe Gly Trp Asp Trp Ile Ile Ala Pro Lys Arg Tyr
```

```
                290                 295                 300
aaa gcc aat tac tgc tct gga gaa tgt gaa ttc gta ttt cta cag aaa      960
Lys Ala Asn Tyr Cys Ser Gly Glu Cys Glu Phe Val Phe Leu Gln Lys
305                 310                 315                 320 tac ccg cac act cac ctg gta cac caa gca aat cca aga ggc tca gca     1008
Tyr Pro His Thr His Leu Val His Gln Ala Asn Pro Arg Gly Ser Ala
                325                 330                 335 ggc cct tgc tgc aca ccc acc aag atg tcc cct ata aac atg ctg tat     1056
Gly Pro Cys Cys Thr Pro Thr Lys Met Ser Pro Ile Asn Met Leu Tyr
                340                 345                 350 ttc aat gga aaa gaa caa ata ata tat gga aag ata cca gcc atg gtt     1104
Phe Asn Gly Lys Glu Gln Ile Ile Tyr Gly Lys Ile Pro Ala Met Val
                355                 360                 365 gta gat cgt tgc ggg tgc tca tga                                      1128
Val Asp Arg Cys Gly Cys Ser
370                 375

<210> SEQ ID NO 14
<211> LENGTH: 375
<212> TYPE: PRT
<213> ORGANISM: Meleagris gallopavo

<400> SEQUENCE: 14

Met Gln Lys Leu Ala Val Tyr Val Tyr Ile Tyr Leu Phe Met Gln Ile
1               5                   10                  15

Leu Val His Pro Val Ala Leu Asp Gly Ser Ser Gln Pro Thr Glu Asn
                20                  25                  30

Ala Glu Lys Asp Gly Leu Cys Asn Ala Cys Thr Trp Arg Gln Asn Thr
            35                  40                  45

Lys Ser Ser Arg Ile Glu Ala Ile Lys Ile Gln Ile Leu Ser Lys Leu
        50                  55                  60

Arg Leu Glu Gln Ala Pro Asn Ile Ser Arg Asp Val Ile Lys Gln Leu
65                  70                  75                  80

Leu Pro Lys Ala Pro Pro Leu Gln Glu Leu Ile Asp Gln Tyr Asp Val
                85                  90                  95

Gln Arg Asp Asp Ser Ser Asp Gly Ser Leu Glu Asp Asp Tyr His
                100                 105                 110

Ala Thr Thr Glu Thr Ile Ile Thr Met Pro Thr Glu Ser Asp Phe Leu
            115                 120                 125

Val Gln Met Glu Gly Lys Pro Lys Cys Cys Phe Phe Lys Phe Ser Ser
        130                 135                 140

Lys Ile Gln Tyr Asn Lys Val Val Lys Ala Gln Leu Trp Ile Tyr Leu
145                 150                 155                 160

Arg Gln Val Gln Lys Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Phe Asp Glu Asn Gly Arg Asp Leu Ala Val Thr
225                 230                 235                 240

Phe Pro Gly Pro Gly Glu Asp Gly Leu Asn Pro Phe Leu Glu Val Arg
                245                 250                 255

Val Thr Asp Thr Pro Lys Arg Ser Arg Arg Asp Phe Gly Leu Asp Cys
```

-continued

```
                    260                 265                 270
Asp Glu His Ser Thr Glu Ser Arg Cys Cys Arg Tyr Pro Leu Thr Val
            275                 280                 285

Asp Phe Glu Ala Phe Gly Trp Asp Trp Ile Ile Ala Pro Lys Arg Tyr
        290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
        355                 360                 365

Val Asp Arg Cys Gly Cys Ser
    370                 375

<210> SEQ ID NO 15
<211> LENGTH: 1393
<212> TYPE: DNA
<213> ORGANISM: Mus musculus
<220> FEATURE:
<221> NAME/KEY: CDS
<222> LOCATION: (54)..(1274)

<400> SEQUENCE: 15
ccgcgggact ccggcgtccc cgccccccag tcctccctcc cctcccctcc agc atg      56
                                                            Met
                                                            1 gtg ctc gcg gcc ccg ctg ctg ctg ggc ttc ctg ctc ctc gcc ctg gag   104
Val Leu Ala Ala Pro Leu Leu Leu Gly Phe Leu Leu Leu Ala Leu Glu
                5                  10                  15 ctg cgg ccc cgg ggg gag gcg gcc gag ggc ccc gcg gcg gcg gcg gcg   152
Leu Arg Pro Arg Gly Glu Ala Ala Glu Gly Pro Ala Ala Ala Ala Ala
            20                  25                  30 gcg gcg gcg gcg gcg gca gcg gcg ggg gtc ggg ggg gag cgc tcc agc   200
Ala Ala Ala Ala Ala Ala Ala Gly Val Gly Gly Glu Arg Ser Ser
        35                  40                  45 cgg cca gcc ccg tcc gtg gcg ccc gag ccg gac ggc tgc ccc gtg tgc   248
Arg Pro Ala Pro Ser Val Ala Pro Glu Pro Asp Gly Cys Pro Val Cys
50                  55                  60                  65 gtt tgg cgg cag cac agc cgc gag ctg cgc cta gag agc atc aag tcg   296
Val Trp Arg Gln His Ser Arg Glu Leu Arg Leu Glu Ser Ile Lys Ser
                70                  75                  80 cag atc ttg agc aaa ctg cgg ctc aag gag gcg ccc aac atc agc cgc   344
Gln Ile Leu Ser Lys Leu Arg Leu Lys Glu Ala Pro Asn Ile Ser Arg
            85                  90                  95 gag gtg gtg aag cag ctg ctg ccc aag gcg ccg ccg ctg cag cag atc   392
Glu Val Val Lys Gln Leu Leu Pro Lys Ala Pro Pro Leu Gln Gln Ile
        100                 105                 110 ctg gac cta cac gac ttc cag ggc gac gcg ctg cag ccc gag gac ttc   440
Leu Asp Leu His Asp Phe Gln Gly Asp Ala Leu Gln Pro Glu Asp Phe
    115                 120                 125 ctg gag gag gac gag tac cac gcc acc acc gag acc gtc att agc atg   488
Leu Glu Glu Asp Glu Tyr His Ala Thr Thr Glu Thr Val Ile Ser Met
130                 135                 140                 145 gcc cag gag acg gac cca gca gta cag aca gat ggc agc cct ctc tgc   536
Ala Gln Glu Thr Asp Pro Ala Val Gln Thr Asp Gly Ser Pro Leu Cys
                150                 155                 160 tgc cat ttt cac ttc agc ccc aag gtg atg ttc aca aag gta ctg aag   584
```

```
Cys His Phe His Phe Ser Pro Lys Val Met Phe Thr Lys Val Leu Lys
        165                 170                 175 gcc cag ctg tgg gtg tac cta cgg cct gta ccc cgc cca gcc aca gtc      632
Ala Gln Leu Trp Val Tyr Leu Arg Pro Val Pro Arg Pro Ala Thr Val
        180                 185                 190 tac ctg cag atc ttg cga cta aaa ccc cta act ggg gaa ggg acc gca      680
Tyr Leu Gln Ile Leu Arg Leu Lys Pro Leu Thr Gly Glu Gly Thr Ala
        195                 200                 205 ggg gga ggg ggc gga ggc cgg cgt cac atc cgt atc cgc tca ctg aag      728
Gly Gly Gly Gly Gly Gly Arg Arg His Ile Arg Ile Arg Ser Leu Lys
210                 215                 220                 225 att gag ctg cac tca cgc tca ggc cat tgg cag agc atc gac ttc aag      776
Ile Glu Leu His Ser Arg Ser Gly His Trp Gln Ser Ile Asp Phe Lys
                230                 235                 240 caa gtg cta cac agc tgg ttc cgc cag cca cag agc aac tgg ggc atc      824
Gln Val Leu His Ser Trp Phe Arg Gln Pro Gln Ser Asn Trp Gly Ile
            245                 250                 255 gag atc aac gcc ttt gat ccc agt ggc aca gac ctg gct gtc acc tcc      872
Glu Ile Asn Ala Phe Asp Pro Ser Gly Thr Asp Leu Ala Val Thr Ser
        260                 265                 270 ctg ggg ccg gga gcc gag ggg ctg cat cca ttc atg gag ctt cga gtc      920
Leu Gly Pro Gly Ala Glu Gly Leu His Pro Phe Met Glu Leu Arg Val
    275                 280                 285 cta gag aac aca aaa cgt tcc cgg cgg aac ctg ggt ctg gac tgc gac      968
Leu Glu Asn Thr Lys Arg Ser Arg Arg Asn Leu Gly Leu Asp Cys Asp
290                 295                 300                 305 gag cac tca agc gag tcc cgc tgc tgc cga tat ccc ctc aca gtg gac     1016
Glu His Ser Ser Glu Ser Arg Cys Cys Arg Tyr Pro Leu Thr Val Asp
                310                 315                 320 ttt gag gct ttc ggc tgg gac tgg atc atc gca cct aag cgc tac aag     1064
Phe Glu Ala Phe Gly Trp Asp Trp Ile Ile Ala Pro Lys Arg Tyr Lys
            325                 330                 335 gcc aac tac tgc tcc ggc cag tgc gag tac atg ttc atg caa aaa tat     1112
Ala Asn Tyr Cys Ser Gly Gln Cys Glu Tyr Met Phe Met Gln Lys Tyr
        340                 345                 350 ccg cat acc cat ttg gtg cag cag gcc aat cca aga ggc tct gct ggg     1160
Pro His Thr His Leu Val Gln Gln Ala Asn Pro Arg Gly Ser Ala Gly
    355                 360                 365 ccc tgt tgt acc ccc acc aag atg tcc cca atc aac atg ctc tac ttc     1208
Pro Cys Cys Thr Pro Thr Lys Met Ser Pro Ile Asn Met Leu Tyr Phe
370                 375                 380                 385 aat gac aag cag cag att atc tac ggc aag atc cct ggc atg gtg gtg     1256
Asn Asp Lys Gln Gln Ile Ile Tyr Gly Lys Ile Pro Gly Met Val Val
                390                 395                 400 gat cgc tgt ggc tgc tct taagtgggtc actacaagct gctggagcaa            1304
Asp Arg Cys Gly Cys Ser
            405 agacttggtg ggtgggtaac ttaacctctt cacagaggat aaaaaatgct tgtgagtatg   1364 acagaaggga ataaacaggc ttaagggt                                      1393

<210> SEQ ID NO 16
<211> LENGTH: 407
<212> TYPE: PRT
<213> ORGANISM: Mus musculus

<400> SEQUENCE: 16

Met Val Leu Ala Ala Pro Leu Leu Leu Gly Phe Leu Leu Leu Ala Leu
1               5                   10                  15

Glu Leu Arg Pro Arg Gly Glu Ala Ala Glu Gly Pro Ala Ala Ala Ala
```

```
                    20                  25                  30
Ala Ala Ala Ala Ala Ala Ala Ala Gly Val Gly Gly Glu Arg Ser
            35                  40                  45
Ser Arg Pro Ala Pro Ser Val Ala Pro Glu Pro Asp Gly Cys Pro Val
 50                  55                  60
Cys Val Trp Arg Gln His Ser Arg Glu Leu Arg Leu Glu Ser Ile Lys
 65                  70                  75                  80
Ser Gln Ile Leu Ser Lys Leu Arg Leu Lys Glu Ala Pro Asn Ile Ser
            85                  90                  95
Arg Glu Val Val Lys Gln Leu Leu Pro Lys Ala Pro Pro Leu Gln Gln
            100                 105                 110
Ile Leu Asp Leu His Asp Phe Gln Gly Asp Ala Leu Gln Pro Glu Asp
            115                 120                 125
Phe Leu Glu Glu Asp Glu Tyr His Ala Thr Thr Glu Thr Val Ile Ser
            130                 135                 140
Met Ala Gln Glu Thr Asp Pro Ala Val Gln Thr Asp Gly Ser Pro Leu
 145                 150                 155                 160
Cys Cys His Phe His Phe Ser Pro Lys Val Met Phe Thr Lys Val Leu
            165                 170                 175
Lys Ala Gln Leu Trp Val Tyr Leu Arg Pro Val Pro Arg Pro Ala Thr
            180                 185                 190
Val Tyr Leu Gln Ile Leu Arg Leu Lys Pro Leu Thr Gly Glu Gly Thr
            195                 200                 205
Ala Gly Gly Gly Gly Gly Arg Arg His Ile Arg Ile Arg Ser Leu
            210                 215                 220
Lys Ile Glu Leu His Ser Arg Ser Gly His Trp Gln Ser Ile Asp Phe
 225                 230                 235                 240
Lys Gln Val Leu His Ser Trp Phe Arg Gln Pro Gln Ser Asn Trp Gly
            245                 250                 255
Ile Glu Ile Asn Ala Phe Asp Pro Ser Gly Thr Asp Leu Ala Val Thr
            260                 265                 270
Ser Leu Gly Pro Gly Ala Glu Gly Leu His Pro Phe Met Glu Leu Arg
            275                 280                 285
Val Leu Glu Asn Thr Lys Arg Ser Arg Arg Asn Leu Gly Leu Asp Cys
 290                 295                 300
Asp Glu His Ser Ser Glu Ser Arg Cys Cys Arg Tyr Pro Leu Thr Val
 305                 310                 315                 320
Asp Phe Glu Ala Phe Gly Trp Asp Trp Ile Ile Ala Pro Lys Arg Tyr
            325                 330                 335
Lys Ala Asn Tyr Cys Ser Gly Gln Cys Glu Tyr Met Phe Met Gln Lys
            340                 345                 350
Tyr Pro His Thr His Leu Val Gln Gln Ala Asn Pro Arg Gly Ser Ala
            355                 360                 365
Gly Pro Cys Cys Thr Pro Thr Lys Met Ser Pro Ile Asn Met Leu Tyr
 370                 375                 380
Phe Asn Asp Lys Gln Gln Ile Ile Tyr Gly Lys Ile Pro Gly Met Val
 385                 390                 395                 400
Val Asp Arg Cys Gly Cys Ser
            405
```